(12) United States Patent
Bruce et al.

(10) Patent No.: US 7,309,816 B1
(45) Date of Patent: Dec. 18, 2007

(54) ZINC FINGER PROTEINS EXPRESSED IN PLANT MERISTEM

(75) Inventors: Wesley B. Bruce, Grimes, IA (US); Suling Zhao, Des Moines, IA (US); Rajeev Gupta, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 11/196,997

(22) Filed: Aug. 4, 2005

Related U.S. Application Data

(60) Provisional application No. 60/598,726, filed on Aug. 4, 2004.

(51) Int. Cl.
*A01H 1/00* (2006.01)
*C07K 14/415* (2006.01)
*C07H 21/04* (2006.01)
*C12N 15/29* (2006.01)

(52) U.S. Cl. .................. 800/290; 435/6; 435/69.1; 435/468; 435/419; 435/320.1; 530/370; 536/23.6; 800/278; 800/295

(58) Field of Classification Search ............ 435/6, 435/69.1, 468, 419, 252.3, 320.1, 183; 530/370; 536/23.6; 800/278, 295
See application file for complete search history.

(56) References Cited

U.S. PATENT DOCUMENTS

| 2003/0018995 A1 | 1/2003 | Dresselhaus et al. |
| 2004/0214272 A1* | 10/2004 | La Rosa et al. ............ 800/278 |

FOREIGN PATENT DOCUMENTS

| WO | 01/12798 A2 | 2/2001 |
| WO | 01/12799 A2 | 2/2001 |
| WO | 01/31017 A2 | 5/2001 |
| WO | 01/64924 A1 | 9/2001 |

* cited by examiner

*Primary Examiner*—Phuong T Bui

(57) ABSTRACT

An isolated polynucleotide encoding a zinc finger protein is provided, as is the isolated zinc finger protein, peptide portions thereof, orthologs of the zinc finger protein, and antibodies that specifically bind the zinc finger protein. Also provided is a transgenic plant, which contains in its genome a transgene containing the polynucleotide encoding the zinc finger protein, or a nucleotide sequence complementary to the encoding polynucleotide. In addition, methods of identifying a nucleotide sequence and/or a heterologous protein that is specifically bound by the zinc finger protein, methods of using the isolated polynucleotide (or encoded polypeptide), for example, to modulate plant cell growth and/or development, are provided.

8 Claims, 5 Drawing Sheets

```
                                 1                                                50
         AAA87298_AtZPF2    (1)  MDYQPNTSLRLSLPSYKNHQLNLELVLEPSSMSSSSSSSTN-----SSSC
   cep7.pk0020.c2:fis_CCHH_pep  (1)  ---------MARQPAGGDDVNLDLRLVHHQSASGGMGRLQHHHLPPVAA
         SCAFFOLD000526_4   (1)  ---------MAVNSREEEGEMNLELTLCYTPPPS------------PPPP
         SCAFFOLD007126_1   (1)  ---------MAVNNREEEGEMNLELTLCYTPPPS------------PEPP
         SCAFFOLD003579_1   (1)  ---------MEVNRGEE-EDVNLELTLCYTSASS------------PEP-
         SCAFFOLD016653_1   (1)  -----MEFGMVEDAAAAAGEEGLTLSLSLQPSP---------------PR
         SCAFFOLD002273_1   (1)  ----MDRYNGGGGGGGEEGDEQLDLNLSLQPSQAN------------EPP
         SCAFFOLD005573_3   (1)  ----MPGAPEFMGEQMDNEELNLSLSLQPSYPSR----------------
         SCAFFOLD002771_1   (1)  ---------MAMDNREE-AEMNLELTLWYTSASP------------PPPP
              Consensus    (1)           M V  E GEMNLELTL YT SSS           P P
                                 51                                               100
         AAA87298_AtZPF2   (46)  LEQPRVFSCNYCQRKFYSSQALGGHQNAHKLERTLAKKSRE------LFR
   cep7.pk0020.c2:fis_CCHH_pep (41) DDPDRSFSCTYCRRKFFSSQALGGHQNAHKLERSLAKRSRE----LSSAV
         SCAFFOLD000526_4  (30)  PPFVGFFFCMYCDRKFHSSQALGGHQNAHKLERSQAKLRRE----AIAAE
         SCAFFOLD007126_1  (30)  --LVGFFLCMYCDRKFDSSQALGGHQNAHKYERSLAKRRRE----IAAAL
         SCAFFOLD003579_1  (28)  ---IGFFLCMYCDRKFYSSQALGGHQNAHKYERSLAKRRRE----IAAAL
         SCAFFOLD016653_1  (31)  --FQALFSGCYCPRKFRSSQALGGHQNAHKLQRNLARRGREAAASIAAAA
         SCAFFOLD002273_1  (35)  ----GYFTCTYCDKKFYSSQALGGHQNAHKFERSVAKRTRE----LAAAR
         SCAFFOLD005573_3  (31)  --FQTEFSCCYCPKRFQSSQALGGHQNAHKLQRNLAKRNRE--AFLSISQ
         SCAFFOLD002771_1  (29)  PFVIGFFLCMYCDRKFDSSQALGGHQNAHKLERSLAKRRRE----AIAAE
              Consensus   (51)      GFFSC YCDRKF SSQALGGHQNAHKLERSLAKR RE    LAAA
                                 101                                              150
         AAA87298_AtZPF2   (90)  ---SSN------------------------TVDSDQPYPFSGRF
   cep7.pk0020.c2:fis_CCHH_pep (87) AVVSAAISSSSAAAAAA---------------PRAAASELCSWYPTAQAG
         SCAFFOLD000526_4  (76)  ILAHRAVVLQAGAAAN----------------HDGGYGAGSDPLPAAQK
         SCAFFOLD007126_1  (74)  RAHGAPPAVDGAGAAG----------------YSSPAAAQKAVSVEAQQ
         SCAFFOLD003579_1  (71)  RAHGAP-------PP-----------------PPAPGGAGAAAAQKAVG
         SCAFFOLD016653_1  (79)  AAAAAAAASSGDQQQQGRTTAAAAAVLAGGESAPPAAARAAADLDGAGVW
         SCAFFOLD002273_1  (77)  RQQAADEEAR----------------------RGAGTTTTREPTGNAS
         SCAFFOLD005573_3  (77)  RKGANAGIKDG---------------------SSALSAESISKISSGK
         SCAFFOLD002771_1  (75)  IREHGRSLRLLAQQDN----------------TDGGSGAGPSVPAAHRV
              Consensus   (101)    AA                              AA   A S        AA
                                 151                                             199
         AAA87298_AtZPF2   (107) ELYGRGYQGFLESGG---SRDFSARRVPESGLDQDQEKSHLDLSLRL--
   cep7.pk0020.c2:fis_CCHH_pep (122) GP-G--DQAAAAAVVSWIADGGRRYAYRVQQAAAASDADDIDLSLRL--
         SCAFFOLD000526_4  (109) VRAEEVQRGAA---ASAPEFGGFARGE-SSPEYGVQQAHGLDLSLRL--
         SCAFFOLD007126_1  (107) HRAAPKVREEAHQGASAPELGGIARGN-SSPEYGVECPHGLDLSLRL--
         SCAFFOLD003579_1  (96)  VEAQQQHQHAP-------VVGGFARGGGKSSPPAEYGDGLDLSLRL--
         SCAFFOLD016653_1  (129) GGAGMRGRPAHHHRLMQGGYSSGGSSAAGGRGNGELADEMIDLSLKL--
         SCAFFOLD002273_1  (103) S-----------------SYQRASPPAEARRRDLLTDDIDLSLKL--
         SCAFFOLD005573_3  (104) KHHKEAWQVMQGSCGSSSSGTVMHKSIEQDVEDEDLSNGTIDLSLKL--
         SCAFFOLD002771_1  (108) RPVEAQQLGDELG-------GGFARGKSASPEYGVEHAHGLDLSLSLRL
              Consensus   (151)                  GG ARG   S   G         LDLSLRL
```

FIGURE 1

A = Active IM, T = Terminated IM

```
              1                                                            60
SEQ ID NO:30  (1)  -MDYQPNTSLRLSLPSYKNHQLNLELVLEPS--------SMSSSSSSSTNSSSCLEQPRVE
SEQ ID NO:31  (1)  -MTESDDASRETPASRGGEASSNQDLSKPESNHVSLDLKLNDTFNDDTKSTKCEANPRVE
SEQ ID NO:32  (1)  ---------MARQPAGGDDVNLDLRLVHHQSASG----GMGRLQHHHLPPVEADDPDRSE
SEQ ID NO:33  (1)  ---------MGGRENYLDLNNLPDDFSKDGNKQALEEGSSSGQRKKKGSKEGKDESGLVE
SEQ ID NO:36  (1)  --------------MERSNSIELRNSFYGRARTSPWSYGDYDNCQQDHDYLLGFSWPPRSY
SEQ ID NO:34  (1)  MMDRGECLMSMKLRPMVTRPSSDGTLFWPFREE-----RAFASAEEYGGGGCMWPPRSY
SEQ ID NO:35  (1)  --------------MEGEDDGAQMKLQQQQQSPCSDNLSLSAASSWLPPQVRSSSSSSSY
Consensus     (1)                L        L              L         G    PRSY
              61                                                          120
SEQ ID NO:30  (53)  SCNYCQRKFYSSQALGGHQNAHRLER--TLAKK-SRELFRSS-------------N-TVD
SEQ ID NO:31  (60)  SCNYCRRKFYSSQALGGHQNAHRRER--TMAKR-RMHMGRMFG------HHHRPYTYTSS
SEQ ID NO:32  (48)  SCTYCRRKFFSSQALGGHQNAHRLER--SLAKR-SRELSSAVA------VVSAAIS--SS
SEQ ID NO:33  (52)  ECRECSLRFCKSQALGGHMNRHQERETETLNQARQLMYRNDTITRPGISPFGYHHTTDP
SEQ ID NO:36  (48)  LCSECKREFRSAQALGGHMNVHRRDR--ARLRL-QQSPSSSSTPSEPYPNPNYSYSTMAN
SEQ ID NO:34  (56)  SCSECGREFKSAQALGGHMNVHRRDR--ARLKQQSLSPSSTDQATEPECDRQQQVLDVGS
SEQ ID NO:35  (47)  LCGYCKREFRSAQGLGGHMNIHRLDR--ARLIHQQYTSHRIAAPHE------------NP
Consensus     (61)  SC YCKRKF SSQALGGHMN HR ER  A LK  S L R     P
              121                                                         180
SEQ ID NO:30  (96)  S------------------------DQLYEFSGRFELYG-------------RGYQG
SEQ ID NO:31  (111) SLGMQAHSGL----------LHHTL---SQHQLLVSRFHHQGYFGNTVPLFFDYDDGGSD
SEQ ID NO:32  (97)  S----------------------AA---LAAAERAAASELCS-------------WYP
SEQ ID NO:33  (112) LIYRSVYSSPMIYPGSSSTNLVPQPPMPPPEPEYPYSSNQYSPHNHFNDYYLNPSFRGSR
SEQ ID NO:36  (105) SPPPHHSPLT----------LFPTLSPPSSRRYAGLIRSLSPKSKHTPENACKTKKSSL
SEQ ID NO:34  (114) KVLVQEETRKPNG-------TKREISDVCNNNVLESSMKRYEHDNGEVKTDLSVGLLSLE
SEQ ID NO:35  (93)  N---------P--------------SCTSVLDLELSLSSLLAHG-----AASSDGGL
Consensus     (121) S                           S    P P        S              S
              181                                                         240
SEQ ID NO:30  (116) FLESGG---------------SRDFSARRVP--------ESGLDQ----------LQ
SEQ ID NO:31  (158) FFWPGS---------------FRQVVEELEAPVVVVASTESGLDLNSVAANGGV---LN
SEQ ID NO:32  (117) TAQAGG---------------PGDQAAAAVVS---WLADGGRRYAYRQQAAA---AS
SEQ ID NO:33  (172) SLSPSPNLPTTTTVDYMADSPVEPGYTCVGAPIGPTGFPIRGPSIVRAPLEPPQGRGDGA
SEQ ID NO:36  (155) LVEAGE---------------ATRFTSKDACK-----LLRNDEILSLELEIGLI---NE
SEQ ID NO:34  (167) FDPRKK--------------QLINGSSSWKRAKTDMSRFPMMLGLVLGISEI---NG
SEQ ID NO:35  (122) SLPVLK--------------LAGNRFSSASPPTTKDLEGKNLELRIG-ACSHG---LG
Consensus     (181)  V G                 A AA        I    L L    L          D
              241            262
SEQ ID NO:30  (140) EKSHLDLSLRL----------
SEQ ID NO:31  (199) NSSKPDLSLRL----------
SEQ ID NO:32  (155) DADDLDLSLRL----------
SEQ ID NO:33  (232) SRQRLDHSLRFPINRFQDHHSL
SEQ ID NO:36  (191) SEQDLDLELRLGFA-------
SEQ ID NO:34  (208) HHEELDLELRLGADPPKVN---
SEQ ID NO:35  (162) AEERLDLQLRLGYY-------
Consensus     (241)     LDLSLRL
```

FIGURE 5

SEQUENCE LISTING

<160> NUMBER OF SEQ ID NOS: 36

<210> SEQ ID NO 1
<211> LENGTH: 672
<212> TYPE: DNA
<213> ORGANISM: Zea mays

<400> SEQUENCE: 1

```
gcacgagctc cgatcctata gagatagaga gctcatggcg aggcagccgg ccggcggcga      60
cgacgtcaac ctggacctgc gcctcgtcca ccaccagtcg gcgtccggcg gtatgggcag     120
gctgcagcac caccacctac cgccggtggc cgccgacgac cctgaccgca gcttctcgtg     180
cacctactgc cgccgcaagt tcttcagctc gcaggcgctg ggcggccacc agaacgcgca     240
caagctggag cgcagcctcg ccaagcgcag ccgcgagctc tccagcgctg tggcggtcgt     300
cagtgcggcc atctcctcct cctctgccgc ggcggcagca gcgccgcggg cggcggcttc     360
agagctctgt agctggtacc cgaccgcgca agcgggaggc ccaggggacc aggcagccgc     420
ggcggccgtc gtgagctgga tcgcagacgg cgggcgccgg tacgcatacc gcgtacaaca     480
agccgcggcg gccagcgacg ccgacgacat cgacctgtcg ctcaggctgt aagctagcta     540
agcgctacgc atgcgcatcg tatgtacgta cgtatgtgta cgcgtgttga agctgcgaaa     600
tttatgagac tactggatcc cattatttat tccaaaaaaa aaaaaaaaaa aaaaaaaaaa     660
aaaaaaaaaa aa                                                         672
```

<210> SEQ ID NO 2
<211> LENGTH: 165
<212> TYPE: PRT
<213> ORGANISM: Zea mays

<400> SEQUENCE: 2

```
Met Ala Arg Gln Pro Ala Gly Gly Asp Asp Val Asn Leu Asp Leu Arg
 1               5                  10                  15

Leu Val His His Gln Ser Ala Ser Gly Gly Met Gly Arg Leu Gln His
            20                  25                  30

His His Leu Pro Pro Val Ala Ala Asp Asp Pro Asp Arg Ser Phe Ser
        35                  40                  45

Cys Thr Tyr Cys Arg Arg Lys Phe Phe Ser Ser Gln Ala Leu Gly Gly
    50                  55                  60

His Gln Asn Ala His Lys Leu Glu Arg Ser Leu Ala Lys Arg Ser Arg
65                  70                  75                  80

Glu Leu Ser Ser Ala Val Ala Val Ser Ala Ala Ile Ser Ser Ser
                85                  90                  95

Ser Ala Ala Ala Ala Ala Ala Pro Arg Ala Ala Ala Ser Glu Leu Cys
               100                 105                 110
```

```
Ser Trp Tyr Pro Thr Ala Gln Ala Gly Gly Pro Gly Asp Gln Ala Ala
        115                 120                 125

Ala Ala Ala Val Val Ser Trp Ile Ala Asp Gly Gly Arg Arg Tyr Ala
    130                 135                 140

Tyr Arg Val Gln Gln Ala Ala Ala Ala Ser Asp Ala Asp Asp Ile Asp
145                 150                 155                 160

Leu Ser Leu Arg Leu
            165

<210> SEQ ID NO 3
<211> LENGTH: 1400
<212> TYPE: DNA
<213> ORGANISM: Zea mays

<400> SEQUENCE: 3
tattacctct caagggagac caaaccagta taaatctttg tgtctttctg ccttactttc      60
tgatctagat cccgcaatac tcctatatca aacccactgt caagaaatcc tcgacaacaa     120
acatgtgcaa tcaatagcat gcacataaca aggtagggtg gttgttagat tatatagcta     180
aaagtaggaa tgtttaacgt gtggccatta tgagggcccg gggtgagtgg caattataca     240
catgaagtcc aataattcct cgataatcct gactcctgcg cggtggtagc tagctcatgg     300
attctctgct cctctcatta ccatcacaac acatatcatt actttcccct gaatcctgat     360
gtcagatata gctaggtcgt ccttcaaaaa cttgaataat gcatgatata ttggaattgg     420
ttatctaata tacatggacc ttggtgctgc atgatgcaca gaatgttctt aaaaattaaa     480
ttacatagca tcaaggcatt tcattattag cacaaatcaa atatatggcc gatctttaaa     540
aaaacaagac cttgaattaa ttaaaaaatg cggcctttga caattaaaga gaatatgaaa     600
tggctttttag cacagccgac atgactcatc acgagagaaa agccaaacca aaggacgtga     660
gacatgcagg cagctgacat cacattcacg gatcatcgct tatatttata caccacgtat     720
tagtgcagtg gatcctcctc ctcaagaggt tcacccactc gatcatatca ccacctccga     780
tcctatagag atagagagct catggcgagg cagccggccg gcggcgacga cgtcaacctg     840
gacctgcgcc tcgtccacca ccagtcggcg tccggcggta tgggcaggct gcagcaccac     900
cacctaccgc cggtggccgc cgacgaccct gaccgcagct tctcgtgcac ctactgccgc     960
cgcaagttct tcagctcgca ggcgctgggc ggccaccaga acgcgcacaa gctggagcgc    1020
agcctcgcca agcgcagccg cgagctctcc agcgctgtgg cggtcgtcag tgcggccatc    1080
tcctcctcct ctgccgcggc ggcagcagcg ccgcgggcgg cggcttcaga gctctgtagc    1140
tggtacccga ccgcgcaagc gggaggccca ggggaccagg cagccgcggc ggccgtcgtg    1200
agctggatcg cagacggcgg gcgccggtac gcataccgcg tacaacaagc cgcggcggcc    1260
agcgacgccg acgacatcga cctgtcgctc aggctgtaag ctagctaagc gctacgcatg    1320
cgcatcgtat gtacgtacgt atgtgtacgc gtgttgaagc tgcgaaattt atgagactac    1380
tggatcccat tatttattcc                                                1400

<210> SEQ ID NO 4
<211> LENGTH: 165
<212> TYPE: PRT
<213> ORGANISM: Zea mays

<400> SEQUENCE: 4

Met Ala Arg Gln Pro Ala Gly Gly Asp Asp Val Asn Leu Asp Leu Arg
1               5                   10                  15
```

| Leu | Val | His | His | Gln | Ser | Ala | Ser | Gly | Gly | Met | Gly | Arg | Leu | Gln | His |
|---|---|---|---|---|---|---|---|---|---|---|---|---|---|---|---|
|  |  |  | 20 |  |  |  | 25 |  |  |  |  | 30 |  |  |  |

| His | His | Leu | Pro | Pro | Val | Ala | Ala | Asp | Asp | Pro | Asp | Arg | Ser | Phe | Ser |
|---|---|---|---|---|---|---|---|---|---|---|---|---|---|---|---|
| 35 |  |  |  |  |  | 40 |  |  |  |  | 45 |  |  |  |  |

| Cys | Thr | Tyr | Cys | Arg | Arg | Lys | Phe | Phe | Ser | Ser | Gln | Ala | Leu | Gly | Gly |
|---|---|---|---|---|---|---|---|---|---|---|---|---|---|---|---|
| 50 |  |  |  |  | 55 |  |  |  |  | 60 |  |  |  |  |  |

His Gln Asn Ala His Lys Leu Glu Arg Ser Leu Ala Lys Arg Ser Arg
65                  70                  75                  80

Glu Leu Ser Ser Ala Val Ala Val Ser Ala Ala Ile Ser Ser
                85                  90                  95

Ser Ala Ala Ala Ala Ala Pro Arg Ala Ala Ser Glu Leu Cys
            100                 105                 110

Ser Trp Tyr Pro Thr Ala Gln Ala Gly Gly Pro Gly Asp Gln Ala Ala
            115                 120                 125

Ala Ala Ala Val Val Ser Trp Ile Ala Asp Gly Gly Arg Arg Tyr Ala
            130                 135                 140

Tyr Arg Val Gln Gln Ala Ala Ala Ser Asp Ala Asp Asp Ile Asp
145                 150                 155                 160

Leu Ser Leu Arg Leu
            165

<210> SEQ ID NO 5
<211> LENGTH: 1405
<212> TYPE: DNA
<213> ORGANISM: Zea mays

<400> SEQUENCE: 5

```
tattacctct caagggagac caaaccagta taaatctttg tgtctttatg ctttactttc      60
tgatctagat cccgcaatac tcctatatca aatccactgt caagaaatcc tcgacaacaa     120
acatgtgcaa tcaatagcat gcacataaca aggtagggtg gttgttagat tatatagcta     180
aaaataggaa tgtttaacgt gtggccatta tgagggcccg gggtgcatga atggcaatta     240
tacacatgaa gtccaataat tcctcgataa tcctgactcc tgagcggtgg tagctagctc     300
atggattctc tgctcctctc attaccatca caacacatat cattactttc ccctgaatcc     360
tgatgtcagg tagctaggtc gtccttcaaa aacttgaata atgcatgata tattggaatt     420
ggttatctaa tatacatgga ccttggtgct gcatgatgca cagaatgttc ttaaaaatta     480
aattacatag catcaaggcg tttcattatt agcacaaatc aaatatatgg ccgatcttta     540
aaaaaacaag accttgaatt aattaaaaaa atgcggcctt tgacaattga agagaatagg     600
aaatggcttt tagcacagcc gacatgactc atcacgagag aaaagccaaa ccgaggacgt     660
gagacatgca ggcagctgac atcacattca cggatcatcg cttatattta tacaccacgt     720
attagtgcag tggatcctcc tcctcaagag gttcacccac tcgatcatat caccacctcc     780
gatcctatag agatagagag ctcatggcga ggcagccggc cggcggcgac gacgtcaacc     840
tggacctgcg cctcgtccac caccagtcgg cgtccggcgg tatgggcagg ccgcagcagc     900
accaccacct accgccggtg gccgccgacg accctgaccg cagcttctcg tgcacctact     960
gccgccgcaa gttcttcagc tcgcaggcgc tgggcggcca ccagaacgcg cacaagctgg    1020
agcgcagcct cgccaagcgc agccgcgagc tctccgcgc tgtggcggtc gtcagtgcgg    1080
ccatctcctc ctcctctgcc gcggcggcag cagcgccgcg ggcggcggct tcagagctct    1140
gtagctggta cccgaccgcg caagcgggag gcccagggga ccaggcagcc gcggcggccg    1200
tcgtgagctg gatcgcagac ggcgggcgcc ggtacgcata ccgcgtacaa caagccgcgg    1260
```

-continued

```
cggccagcga cgccgacgac atcgacctgt cgctcaggct gtaagctagc taagcgctac    1320
gcatgcgcat cgtatgtacg tacgtatgtg tacgcgtgtt gaagctgcga aatttatgag    1380
actactggat cccattattt attcc                                          1405
```

<210> SEQ ID NO 6
<211> LENGTH: 166
<212> TYPE: PRT
<213> ORGANISM: Zea mays

<400> SEQUENCE: 6

```
Met Ala Arg Gln Pro Ala Gly Gly Asp Asp Val Asn Leu Asp Leu Arg
 1               5                  10                  15

Leu Val His His Gln Ser Ala Ser Gly Gly Met Gly Arg Pro Gln Gln
            20                  25                  30

His His His Leu Pro Pro Val Ala Ala Asp Asp Pro Asp Arg Ser Phe
        35                  40                  45

Ser Cys Thr Tyr Cys Arg Arg Lys Phe Phe Ser Ser Gln Ala Leu Gly
    50                  55                  60

Gly His Gln Asn Ala His Lys Leu Glu Arg Ser Leu Ala Lys Arg Ser
65                  70                  75                  80

Arg Glu Leu Ser Ser Ala Val Ala Val Val Ser Ala Ala Ile Ser Ser
                85                  90                  95

Ser Ser Ala Ala Ala Ala Ala Pro Arg Ala Ala Ala Ser Glu Leu
            100                 105                 110

Cys Ser Trp Tyr Pro Thr Ala Gln Ala Gly Gly Pro Gly Asp Gln Ala
        115                 120                 125

Ala Ala Ala Val Val Ser Trp Ile Ala Asp Gly Gly Arg Arg Tyr
    130                 135                 140

Ala Tyr Arg Val Gln Gln Ala Ala Ala Ser Asp Ala Asp Asp Ile
145                 150                 155                 160

Asp Leu Ser Leu Arg Leu
                165
```

<210> SEQ ID NO 7
<211> LENGTH: 1397
<212> TYPE: DNA
<213> ORGANISM: Zea mays

<400> SEQUENCE: 7

```
tacctctcaa gggagaccaa accagtataa atctttgtgt ctttctgcct tactttctga     60
tctagatccc gcaatactcc tatatcaaac ccactgtcaa gaaatcctcg acaacaaaca    120
tgtgcaatca atagcatgca cataacaagg tagggtggtt gttagattat atagctaaaa    180
gtaggaatgt ttaacgtgtg gccattatga gggcccgggg tgagtggcaa ttatacacat    240
gaagtccaat aattcctcga taatcctgac tcctgcgcgg tggtagctag ctcatggatt    300
ctctgctcct ctcattacca tcacaacaca tatcattact ttcccctgaa tcctgatgtc    360
agatatagct aggtcgtcct tcaaaaactt gaataatgca tgatatattg gaattggtta    420
tctaatatac atggaccttg gtgctgcatg atgcacagaa tgttcttaaa aattaaatta    480
catagcatca aggcatttca ttattagcac aaatcaaata tatggccgat ctttaaaaaa    540
acaagacctt ggattaatta aaaaatgcgg cctttgacaa ttaaagagaa tatgaaatgg    600
cttttagcac agccgacatg actcatcacg agagaaaagc caaaccaaag gacgtgagac    660
atgcaggcag ctgacatcac gctcacggat catcgcttat atttatacac cacgtattag    720
```

```
tgcagtggat cctcctcctc aagaggttca cccactcgat catatcacca cctccgatcc    780
tatagagata gagagctcat ggcgaggcag ccggccggcg gcgacgacgt caacctggac    840
ctgcgcctcg tccaccacca gtcggcgtcc ggcggtatgg gcaggctgca gcaccaccac    900
ctaccgccgg tggccgccga cgaccctgac cgcagcttct cgtgcaccta ctgccgccgc    960
aagttcttca gctcgcaggc gctgggcggc caccagaacg cgcacaagct ggagcgcagc   1020
ctcgccaagc gcagccgcga gctctccagc gctgtggcgg tcgtcagtgc ggccatctcc   1080
tcctcctctg ccgcggcggc agcagcgccg cgggcggcgg cttcagagct ctgtagctgg   1140
tacccgaccg cgcaagcggg aggcccaggg gaccaggcag ccgcggcggc cgtcgtgagc   1200
tggatcgcag acggcgggcg ccggtacgca taccgcgtac aacaagccgc ggcggccagc   1260
gacgccgacg acatcgacct gtcgctcagg ctgtaagcta gctaagcgct acgcatgcgc   1320
atcgtatgta cgtacgtatg tgtacgcgtg ttgaagctgc gaaatttatg agactactgg   1380
atcccattat ttattcc                                                  1397
```

<210> SEQ ID NO 8
<211> LENGTH: 164
<212> TYPE: PRT
<213> ORGANISM: Zea mays

<400> SEQUENCE: 8

```
Met Ala Arg Gln Pro Ala Gly Gly Asp Asp Val Asn Leu Asp Leu Arg
1               5                   10                  15
Leu Val His His Gln Ser Ala Ser Gly Gly Met Gly Arg Leu Gln His
                20                  25                  30
His His Leu Pro Pro Val Ala Ala Asp Asp Pro Asp Arg Ser Phe Ser
            35                  40                  45
Cys Thr Tyr Cys Arg Arg Lys Phe Phe Ser Ser Gln Ala Leu Gly Gly
        50                  55                  60
His Gln Asn Ala His Lys Leu Glu Arg Ser Leu Ala Lys Arg Ser Arg
65                  70                  75                  80
Glu Leu Ser Ser Ala Val Ala Val Val Ser Ala Ala Ile Ser Ser Ser
                85                  90                  95
Ser Ala Ala Ala Ala Ala Pro Arg Ala Ala Ala Ser Glu Leu Cys
                100                 105                 110
Ser Trp Tyr Pro Thr Ala Gln Ala Gly Gly Pro Gly Asp Gln Ala Ala
            115                 120                 125
Ala Ala Ala Val Val Ser Trp Ile Ala Asp Gly Gly Arg Arg Tyr Ala
        130                 135                 140
Tyr Arg Val Gln Gln Ala Ala Ala Ser Asp Ala Asp Asp Ile Asp
145                 150                 155                 160
Leu Ser Leu Arg
```

<210> SEQ ID NO 9
<211> LENGTH: 1400
<212> TYPE: DNA
<213> ORGANISM: Zea mays

<400> SEQUENCE: 9

```
tattacctct caagggagac caaaccagta taaatctttg tgtctttctg ccttactttc     60
tgatctagat cccgcaatac tcctatatca aacccactgt caagaaatcc tcgacaacaa    120
acatgtgcaa tcaatagcat gcacataaca aggtaggggtg gttgttagat tatatagcta   180
```

-continued

```
aaagtaggaa tgtttaacgt gtggccatta tgagggcccg gggtgagtgg caattataca    240
catgaagtcc aataattcct cgataatcct gactcctgcg cggtggtagc tagctcatgg    300
attctctgct cctctcatta ccatcacaac acatatcatt actttcccct gaatcctgat    360
gtcagatata gctaggccgt ccttcaaaaa cttgaataat gcatgatata ttggaattgg    420
ttatctaata tacatggacc ttggtgctgc atgatgcaca gaatgttctt aaaaattaaa    480
ttacatagca tcaaggcatt tcattattag cacaaatcaa atatatggcc gatctttaaa    540
aaaacaagac cttgaattaa ttaaaaaatg cggcctttga caattaaaga gaatatgaaa    600
tggcttttag cacagccgac atgactcatc acgagagaaa agccaaacca aaggacgtga    660
gacatgcagg cagctgacat cacattcacg gatcatcgct tatatttata caccacgtat    720
tagtgcagtg gatcctcctc ctcaagaggt tcacccactc gatcatatca ccacctccga    780
tcctatagag atagagagct catggcgagg cagccggccg gcggcgacga cgtcaacctg    840
gacctgcgcc tcgtccacca ccagtcggcg tccggcggta tgggcaggct gcagcaccac    900
cacctaccgc cggtggccgc cgacgaccct gaccgcagct tctcgtgcac ctactgccgc    960
cgcaagttct tcagctcgca ggcgctgggc ggccaccaga cgcgcacaa gctggagcgc   1020
agcctcgcca agcgcagccg cgagctctcc agcgctgtgg cggtcgtcag tgcggccatc   1080
tcctcctcct ctgccgcggc ggcagcagcc cgcgggcgg cggcttcaga gctctgtagc   1140
tggtacccga ccgcgcaagc gggaggccca ggggaccagg cagccgcggc ggccgtcgtg   1200
agctggatcg cagacggcgg gcgccggtac gcataccgcg tacaacaagc cgcggcggcc   1260
agcgacgccg acgacatcga cctgtcgctc aggctgtaag ctagctaagc gctacgcatg   1320
cgcatcgtat gtacgtacgt atgtgtacgc gtgttgaagc tgcgaaattt atgagactac   1380
tggatcccat tatttattcc                                              1400
```

<210> SEQ ID NO 10
<211> LENGTH: 165
<212> TYPE: PRT
<213> ORGANISM: Zea mays

<400> SEQUENCE: 10

```
Met Ala Arg Gln Pro Ala Gly Gly Asp Asp Val Asn Leu Asp Leu Arg
  1               5                  10                  15

Leu Val His His Gln Ser Ala Ser Gly Gly Met Gly Arg Leu Gln His
             20                  25                  30

His His Leu Pro Pro Val Ala Ala Asp Asp Pro Asp Arg Ser Phe Ser
         35                  40                  45

Cys Thr Tyr Cys Arg Arg Lys Phe Phe Ser Ser Gln Ala Leu Gly Gly
     50                  55                  60

His Gln Asn Ala His Lys Leu Glu Arg Ser Leu Ala Lys Arg Ser Arg
 65                  70                  75                  80

Glu Leu Ser Ser Ala Val Ala Val Val Ser Ala Ile Ser Ser Ser Ser
                 85                  90                  95

Ser Ala Ala Ala Ala Ala Pro Arg Ala Ala Ser Glu Leu Cys
            100                 105                 110

Ser Trp Tyr Pro Thr Ala Gln Ala Gly Gly Pro Gly Asp Gln Ala Ala
            115                 120                 125

Ala Ala Ala Val Val Ser Trp Ile Ala Asp Gly Gly Arg Arg Tyr Ala
        130                 135                 140

Tyr Arg Val Gln Gln Ala Ala Ala Ser Asp Ala Asp Asp Ile Asp
145                 150                 155                 160
```

Leu Ser Leu Arg Leu
            165

<210> SEQ ID NO 11
<211> LENGTH: 1405
<212> TYPE: DNA
<213> ORGANISM: Zea mays

<400> SEQUENCE: 11

| | | | | | |
|---|---|---|---|---|---|
| tattacctct | caagggagac | caaaccagta | taaatctttg | tgtctttatg | ctttactttc | 60 |
| tgatctagat | cccgcaatac | tcctatatca | aatccactgt | caagaaatcc | ttgacaacaa | 120 |
| acatgtgcaa | tcaatagcat | gcacataaca | aggtagggtg | gttgttagat | tatatagcta | 180 |
| aaaataggaa | tgtttaacgt | gtggccatta | tgagggcccg | gggtgcatga | atggcaatta | 240 |
| tacacatgaa | gtccaataat | tcctcgataa | tcctgactcc | tgagcggtgg | tagctagctc | 300 |
| atggattctc | tgctcctctc | attaccatca | caacacatat | cattactttc | ccctgaatcc | 360 |
| tgatgtcagg | tagctaggtc | gtccttcaaa | aacttgaata | atgcatgata | tattggaatt | 420 |
| ggttatctaa | tatacatgga | ccttggtgct | gcatgatgca | cagaatgttc | ttaaaaatta | 480 |
| aattacatag | catcaaggca | tttcattatt | agcacaaatc | aaatatatgg | ccgatcttta | 540 |
| aaaaacaag | accttgaatt | aattaaaaaa | atgcggcctt | tgacaattaa | agagaatagg | 600 |
| aaatggcttt | tagcacagcc | gacatgactc | atcacgagag | aaaagccaaa | ccgaggacgt | 660 |
| gagacatgca | ggcagctgac | atcacattca | cggatcatcg | cttatattta | tacaccacgt | 720 |
| attagtgcag | tggatcctcc | tcctcaagag | gttcacccac | tcgatcatat | caccacctcc | 780 |
| gatcctatag | agatagagag | ctcatggcga | ggcagccggc | cggcggcgac | gacgtcaacc | 840 |
| tggacctgcg | cctcgtccac | caccagtcgg | cgtccggcgg | tatgggcagg | ccgcagcagc | 900 |
| accaccacct | accgccggtg | gccgccgacg | accctgaccg | cagcttctcg | tgcacctact | 960 |
| gccgccgcaa | gttcttcagc | tcgcaggcgc | tgggcggcca | ccagaacgcg | cacaagctgg | 1020 |
| agcgcagcct | cgccaagcgc | agccgcgagc | tctccagcgc | tgtggcggtc | gtcagtgcgg | 1080 |
| ccatctcctc | ctcctctgcc | gcggcggcag | cagcgccgcg | ggcggcggct | tcagagctct | 1140 |
| gtagctggta | cccgaccgcg | caagcggag | gcccagggga | ccaggcagcc | gcggcggccg | 1200 |
| tcgtgagctg | gatcgcagac | ggcgggcgcc | ggtacgcata | ccgcgtacaa | caagccgcgg | 1260 |
| cggccagcga | cgccgacgac | atcgacctgt | cgctcaggct | gtaagctagc | taagcgctac | 1320 |
| gcatgcgcat | cgtatgtacg | tacgtatgtg | tacgcgtgtt | gaagctgcga | aatttatgag | 1380 |
| actactggat | cccattattt | attcc | | | | 1405 |

<210> SEQ ID NO 12
<211> LENGTH: 166
<212> TYPE: PRT
<213> ORGANISM: Zea mays

<400> SEQUENCE: 12

Met Ala Arg Gln Pro Ala Gly Gly Asp Asp Val Asn Leu Asp Leu Arg
 1               5                  10                  15

Leu Val His His Gln Ser Ala Ser Gly Gly Met Gly Arg Pro Gln Gln
            20                  25                  30

His His His Leu Pro Pro Val Ala Ala Asp Asp Pro Asp Arg Ser Phe
        35                  40                  45

Ser Cys Thr Tyr Cys Arg Arg Lys Phe Phe Ser Ser Gln Ala Leu Gly
    50                  55                  60

```
Gly His Gln Asn Ala His Lys Leu Glu Arg Ser Leu Ala Lys Arg Ser
 65                  70                  75                  80

Arg Glu Leu Ser Ser Ala Val Ala Val Val Ser Ala Ala Ile Ser Ser
                 85                  90                  95

Ser Ser Ala Ala Ala Ala Ala Ala Pro Arg Ala Ala Ala Ser Glu Leu
            100                 105                 110

Cys Ser Trp Tyr Pro Thr Ala Gln Ala Gly Gly Pro Gly Asp Gln Ala
            115                 120                 125

Ala Ala Ala Val Val Ser Trp Ile Ala Asp Gly Gly Arg Arg Tyr
        130                 135                 140

Ala Tyr Arg Val Gln Gln Ala Ala Ala Ala Ser Asp Ala Asp Ile
145                 150                 155                 160

Asp Leu Ser Leu Arg Leu
                165

<210> SEQ ID NO 13
<211> LENGTH: 1400
<212> TYPE: DNA
<213> ORGANISM: Zea mays

<400> SEQUENCE: 13
tattacctct caagggagac caaaccagta taaatctttg tgtctttctg ccttactttc      60
tgatctagat cccgcaatac tcctatatca aacccactgt caagaaatcc tcgacaacaa     120
acatgtgcaa tcaatagcat gcacataaca aggtagggtg gttgttagat tatatagcta     180
aaagtaggaa tgtttaacgt gtggccatta tgagggcccg gggtgagtgg caattataca     240
catgaagtcc ataattcct cgataatcct gactcctgcg cggtggtagc tagctcatgg      300
attctctgct cctctcatta ccatcacaac acatatcatt actttcccct gaatcctgat     360
gtcagatata gctaggtcgt ccttcaaaaa cttgaataat gcatgatata ttggaattgg     420
ttatctaata tacatggacc ttggtgctgc atgatgcaca gaatgttctt aaaaattaaa     480
ttacatagca tcaaggcatt tcattattag cacaaatcaa atatatgccc gatctttaaa     540
aaaacaagac cttgaattaa ttaaaaaatg cggcctttga caattaaaga gaatatgaaa     600
tggcttttag cacagccgac atgactcatc acgagagaaa agccaaacca aggacgtga     660
gacatgcagg cagctgacat cacattcacg gatcatcgct tatatttata caccacgtat     720
tagtgcagtg gatcctcctc ctcaagaggt tcacccactc gatcatatca ccacctccga     780
tcctatagag atagagagct catggcgagg cagccggccg gcggcgacga cgtcaacctg     840
gacctgcgcc tcgtccacca ccagtcggcg tccggcggta tgggcaggct gcagcaccac     900
cacctaccgc cggtggccgc cgacgaccct gaccgcagct tctcgtgcac ctactgccgc     960
cgcaagttct tcagctcgca ggcgctgggc ggccaccaga acgcgcacaa gctggagcgc    1020
agcctcgcca agcgcagccg cgagctctcc agcgctgtgg cggtcgtcag tgcggccatc    1080
tcctcctcct ctgccgcggc ggcagcagcg ccgcgggcgg cggcttcaga gctctgtagc    1140
tggtacccga ccgcgcaagc gggagggccca ggggaccagg cagccgcggc ggccgtcgtg    1200
agctggatcg cagacggcgg gcgccggtac gcataccgcg tacaacaagc gcggcggcc    1260
agcgacgccg acgacatcga cctgtcgctc aggctgtaag ctagctaagc gctacgcatg    1320
cgcatcgtat gtacgtacgt atgtgtacgc gtgttgaagc tgcgaaattt atgagactac    1380
tggatcccat tatttattcc                                                 1400
```

<210> SEQ ID NO 14
<211> LENGTH: 165
<212> TYPE: PRT
<213> ORGANISM: Zea mays

<400> SEQUENCE: 14

```
Met Ala Arg Gln Pro Ala Gly Gly Asp Asp Val Asn Leu Asp Leu Arg
 1               5                  10                  15

Leu Val His His Gln Ser Ala Ser Gly Gly Met Gly Arg Leu Gln His
             20                  25                  30

His His Leu Pro Pro Val Ala Ala Asp Asp Pro Asp Arg Ser Phe Ser
         35                  40                  45

Cys Thr Tyr Cys Arg Arg Lys Phe Phe Ser Ser Gln Ala Leu Gly Gly
     50                  55                  60

His Gln Asn Ala His Lys Leu Glu Arg Ser Leu Ala Lys Arg Ser Arg
 65                  70                  75                  80

Glu Leu Ser Ser Ala Val Ala Val Val Ser Ala Ala Ile Ser Ser Ser
                 85                  90                  95

Ser Ala Ala Ala Ala Ala Pro Arg Ala Ala Ala Ser Glu Leu Cys
            100                 105                 110

Ser Trp Tyr Pro Thr Ala Gln Ala Gly Gly Pro Gly Asp Gln Ala Ala
            115                 120                 125

Ala Ala Ala Val Val Ser Trp Ile Ala Asp Gly Gly Arg Arg Tyr Ala
        130                 135                 140

Tyr Arg Val Gln Gln Ala Ala Ala Ser Asp Ala Asp Ile Asp
145                 150                 155                 160

Leu Ser Leu Arg Leu
            165
```

<210> SEQ ID NO 15
<211> LENGTH: 720
<212> TYPE: DNA
<213> ORGANISM: Oryza sativa

<400> SEQUENCE: 15

```
atggagaagg agatcatcag cgcgaggtcg acgacgacga cgacgaccac cgccgccgcc      60
ggcgacgtca acctcgacct gcggctggtc cactccacgg cggccggcag cagcacacc     120
gcggccacca ggaacccggc gccgcctctc gccgccgccg cgacgaccg cgccttctcg     180
tgcacctact gccggcgcag gttctacagc tcgcaggcgc tgggcggcca ccagaacgcg     240
cacaagctcg agcgcagcct cgccaagcgc agccgcgagc tctccgccgg cgtcacgacg     300
gcggcggcgc cgccgccgcc gcatcctgag ctcggctggc cctacccgcc gcagggcggc     360
gccgccgcgg ccgtcgtcag ctggatcgcc gacggcgggc gccgctacgg gtaccgcgtg     420
cacgccgcgg cagccggcgg cgacgccgag gacatcgacc tttctctcaa gttctctatg     480
gcttcatggg gcctcagata tctcatggac acatggtgt gccgtcccta tgaggcaaat     540
ggacaaatgg ggcttgtcac catcatatca gcttatcatg acatatgcca gatgctggat     600
ggtattggcc tacctgaaaa ggaccttgca ttgatcaagc atacaggtct tgtcaatggg     660
atgaagagat cagttgagct taaccaagat aaaaactcgg aagatcctgg gattggttaa     720
```

<210> SEQ ID NO 16
<211> LENGTH: 239
<212> TYPE: PRT
<213> ORGANISM: Oryza sativa

<400> SEQUENCE: 16

| Met | Glu | Lys | Glu | Ile | Ile | Ser | Ala | Arg | Ser | Thr | Thr | Thr | Thr | Thr |
|1| | | |5| | | | |10| | | | |15|

Thr Ala Ala Ala Gly Asp Val Asn Leu Asp Leu Arg Leu Val His Ser
                20                25             30

Thr Ala Ala Gly Arg Gln His Thr Ala Ala Thr Arg Asn Pro Ala Pro
        35              40              45

Pro Leu Ala Ala Ala Gly Asp Asp Arg Ala Phe Ser Cys Thr Tyr Cys
 50                 55              60

Arg Arg Arg Phe Tyr Ser Ser Gln Ala Leu Gly Gly His Gln Asn Ala
65             70              75              80

His Lys Leu Glu Arg Ser Leu Ala Lys Arg Ser Arg Glu Leu Ser Ala
                85              90           95

Gly Val Thr Thr Ala Ala Pro Pro Pro His Pro Glu Leu Gly
           100            105          110

Trp Pro Tyr Pro Pro Gln Gly Gly Ala Ala Ala Val Val Ser Trp
     115            120             125

Ile Ala Asp Gly Gly Arg Arg Tyr Gly Tyr Arg Val His Ala Ala Ala
 130                135             140

Ala Gly Gly Asp Ala Glu Asp Ile Asp Leu Ser Leu Lys Phe Ser Met
145           150              155           160

Ala Ser Trp Gly Leu Arg Tyr Leu Met Asp His Met Val Leu Pro Ser
            165           170            175

Tyr Glu Ala Asn Gly Gln Met Gly Leu Val Thr Ile Ile Ser Ala Tyr
        180             185             190

His Asp Ile Cys Gln Met Leu Asp Gly Ile Gly Leu Pro Glu Lys Asp
        195            200            205

Leu Ala Leu Ile Lys His Thr Gly Leu Val Asn Gly Met Lys Arg Ser
 210               215            220

Val Glu Leu Asn Gln Asp Lys Asn Ser Glu Asp Pro Gly Ile Gly
225           230              235

<210> SEQ ID NO 17
<211> LENGTH: 728
<212> TYPE: DNA
<213> ORGANISM: Arabidopsis thaliana

<400> SEQUENCE: 17

```
aagcttgata tcgcctctct ctaatctctc tttctctctc tatctctaag aatatataaa      60
ggtatggact accagccaaa cacatcccta cgtctaagcc taccaagtta caagaaccac     120
caactaaacc tagaacttgt tctcgagcct tcttccatgt cttcttcttc atcttcttcc     180
acgaactcat catcatgttt ggagcagcct agggtattct catgtaacta ttgtcaaaga     240
aagttttaca gctctcaagc tcttggtggt catcaaaacg ctcataagct tgagagaacc     300
ttagccaaga gagtcgaga actctttaga tcctcaaaca ctgttgattc tgatcagcct     360
tacccgttct ccggtcgctt tgagctttac ggccgtggct accaaggatt tctcgaaagt     420
ggcggctcga gggacttctc cgcccgccgt gtgccggaga gtggtcttga tcaggatcag     480
gagaagagtc accttgactt atccttaagg ctctaaaaga atcttatatt tgttagtct      540
atatattatc atatcaattg ttaatcttaa aattgattgt tttacttatt agtcatttcc     600
tattatctga agttttcttt tgtaagttgt aactatggtc ctaaattcaa atccaaattt     660
gattttggaa gatggtacct aatgcagtag ttaaataagt taaaaaaatg aaggatctat     720
aattctct                                                              728
```

<210> SEQ ID NO 18
<211> LENGTH: 150
<212> TYPE: PRT
<213> ORGANISM: Arabidopsis thaliana

<400> SEQUENCE: 18

```
Met Asp Tyr Gln Pro Asn Thr Ser Leu Arg Leu Ser Leu Pro Ser Tyr
 1               5                  10                  15

Lys Asn His Gln Leu Asn Leu Glu Leu Val Leu Glu Pro Ser Ser Met
            20                  25                  30

Ser Ser Ser Ser Ser Ser Ser Thr Asn Ser Ser Ser Cys Leu Glu Gln
        35                  40                  45

Pro Arg Val Phe Ser Cys Asn Tyr Cys Gln Arg Lys Phe Tyr Ser Ser
 50                  55                  60

Gln Ala Leu Gly Gly His Gln Asn Ala His Lys Leu Glu Arg Thr Leu
 65                  70                  75                  80

Ala Lys Lys Ser Arg Glu Leu Phe Arg Ser Ser Asn Thr Val Asp Ser
                85                  90                  95

Asp Gln Pro Tyr Pro Phe Ser Gly Arg Phe Glu Leu Tyr Gly Arg Gly
            100                 105                 110

Tyr Gln Gly Phe Leu Glu Ser Gly Gly Ser Arg Asp Phe Ser Ala Arg
        115                 120                 125

Arg Val Pro Glu Ser Gly Leu Asp Gln Asp Gln Glu Lys Ser His Leu
    130                 135                 140

Asp Leu Ser Leu Arg Leu
145                 150
```

<210> SEQ ID NO 19
<211> LENGTH: 28
<212> TYPE: DNA
<213> ORGANISM: oligonucleotide

<400> SEQUENCE: 19
ggaataaata atgggatcca gtagtctc                                        28

<210> SEQ ID NO 20
<211> LENGTH: 24
<212> TYPE: DNA
<213> ORGANISM: oligonucleotide

<400> SEQUENCE: 20
gcacgagctc cgatcctata gaga                                            24

<210> SEQ ID NO 21
<211> LENGTH: 25
<212> TYPE: DNA
<213> ORGANISM: oligonucleotide

<400> SEQUENCE: 21
tattacctct caagggagac caaac                                           25

<210> SEQ ID NO 22
<211> LENGTH: 25
<212> TYPE: DNA
<213> ORGANISM: oligonucleotide

<400> SEQUENCE: 22
ccatgagctc tctatctcta tagga                                           25

```
<210> SEQ ID NO 23
<211> LENGTH: 26
<212> TYPE: DNA
<213> ORGANISM: oligonucleotide

<400> SEQUENCE: 23
gctccgatcc tatagagata gagagc                                          26

<210> SEQ ID NO 24
<211> LENGTH: 25
<212> TYPE: DNA
<213> ORGANISM: oligonucleotide

<400> SEQUENCE: 24
ttagctagct tacagcctga gcgac                                           25

<210> SEQ ID NO 25
<211> LENGTH: 30
<212> TYPE: DNA
<213> ORGANISM: Oligonucleotide

<400> SEQUENCE: 25
agcccgatgg caccatgccc agtgatacct                                      30

<210> SEQ ID NO 26
<211> LENGTH: 28
<212> TYPE: DNA
<213> ORGANISM: oligonucleotide

<400> SEQUENCE: 26
aacaccaaga atccctgcag cccagtgc                                        28

<210> SEQ ID NO 27
<211> LENGTH: 21
<212> TYPE: PRT
<213> ORGANISM: Zea mays
<220> FEATURE:
<221> NAME/KEY: UNSURE
<222> LOCATION: (2)...(3)
<223> OTHER INFORMATION: Xaa = any amino acid
<220> FEATURE:
<221> NAME/KEY: UNSURE
<222> LOCATION: (5)...(16)
<223> OTHER INFORMATION: Xaa = any amino acid
<220> FEATURE:
<221> NAME/KEY: UNSURE
<222> LOCATION: (18)...(20)
<223> OTHER INFORMATION: Xaa = any amino acid

<400> SEQUENCE: 27

Cys Xaa Xaa Cys Xaa Xaa Xaa Xaa Xaa Xaa Xaa Xaa Xaa Xaa Xaa
 1               5                  10                  15

His Xaa Xaa Xaa His
             20

<210> SEQ ID NO 28
<211> LENGTH: 21
<212> TYPE: PRT
<213> ORGANISM: Zea mays

<400> SEQUENCE: 28

Cys Thr Tyr Cys Arg Arg Lys Phe Phe Ser Ser Gln Ala Leu Gly Gly
 1               5                  10                  15

His Gln Asn Ala His
             20
```

```
<210> SEQ ID NO 29
<211> LENGTH: 21
<212> TYPE: PRT
<213> ORGANISM: Zea mays
<220> FEATURE:
<221> NAME/KEY: UNSURE
<222> LOCATION: 2,5,7,9
<223> OTHER INFORMATION: Xaa = any amino acid

<400> SEQUENCE: 29

Cys Xaa Tyr Cys Xaa Arg Xaa Phe Xaa Ser Ser Gln Ala Leu Gly Gly
 1               5                  10                  15

His Gln Asn Ala His
            20

<210> SEQ ID NO 30
<211> LENGTH: 150
<212> TYPE: PRT
<213> ORGANISM: Arabidopsis thaliana

<400> SEQUENCE: 30

Met Asp Tyr Gln Pro Asn Thr Ser Leu Arg Leu Ser Leu Pro Ser Tyr
 1               5                  10                  15

Lys Asn His Gln Leu Asn Leu Glu Leu Val Leu Glu Pro Ser Ser Met
            20                  25                  30

Ser Ser Ser Ser Ser Ser Ser Thr Asn Ser Ser Ser Cys Leu Glu Gln
        35                  40                  45

Pro Arg Val Phe Ser Cys Asn Tyr Cys Gln Arg Lys Phe Tyr Ser Ser
    50                  55                  60

Gln Ala Leu Gly Gly His Gln Asn Ala His Lys Leu Glu Arg Thr Leu
65                  70                  75                  80

Ala Lys Lys Ser Arg Glu Leu Phe Arg Ser Ser Asn Thr Val Asp Ser
                85                  90                  95

Asp Gln Pro Tyr Pro Phe Ser Gly Arg Phe Glu Leu Tyr Gly Arg Gly
            100                 105                 110

Tyr Gln Gly Phe Leu Glu Ser Gly Gly Ser Arg Asp Phe Ser Ala Arg
        115                 120                 125

Arg Val Pro Glu Ser Gly Leu Asp Gln Asp Gln Glu Lys Ser His Leu
    130                 135                 140

Asp Leu Ser Leu Arg Leu
145                 150

<210> SEQ ID NO 31
<211> LENGTH: 209
<212> TYPE: PRT
<213> ORGANISM: Arabidopsis thaliana

<400> SEQUENCE: 31

Met Thr Glu Ser Asp Asp Ala Ser Arg Glu Thr Pro Ala Ser Arg Gly
 1               5                  10                  15

Gly Glu Ala Ser Ser Asn Gln Asp Leu Ser Lys Pro Glu Ser Asn His
            20                  25                  30

Val Ser Leu Asp Leu Lys Leu Asn Asp Thr Phe Asn Asp Asp Thr Lys
        35                  40                  45

Ser Thr Lys Cys Glu Ala Asn Pro Arg Val Phe Ser Cys Asn Tyr Cys
    50                  55                  60

Arg Arg Lys Phe Tyr Ser Ser Gln Ala Leu Gly Gly His Gln Asn Ala
65                  70                  75                  80
```

His Lys Arg Glu Arg Thr Met Ala Lys Arg Ala Met His Met Gly Arg
                85                  90                  95

Met Phe Gly His His His Arg Pro Tyr Thr Tyr Thr Ser Ser Ser Leu
            100                 105                 110

Gly Met Gln Ala His Ser Gly Leu Leu His His Thr Leu Ser Gln Pro
        115                 120                 125

Gln Pro Leu Val Ser Arg Phe His His Gln Gly Tyr Phe Gly Asn Thr
    130                 135                 140

Val Pro Leu Phe Phe Asp Tyr Asp Asp Gly Ser Asp Phe Phe Trp
145                 150                 155                 160

Pro Gly Ser Phe Arg Gln Val Val Glu Glu Ala Glu Ala Pro Val Val
                165                 170                 175

Val Val Ala Ser Thr Glu Ser Gly Leu Asp Leu Asn Ser Val Ala Ala
            180                 185                 190

Asn Gly Gly Val Asp Asn Asn Ser Ser Lys Pro Asp Leu Thr Leu Arg
        195                 200                 205

Leu

<210> SEQ ID NO 32
<211> LENGTH: 165
<212> TYPE: PRT
<213> ORGANISM: Zea mays

<400> SEQUENCE: 32

Met Ala Arg Gln Pro Ala Gly Gly Asp Asp Val Asn Leu Asp Leu Arg
1               5                   10                  15

Leu Val His His Gln Ser Ala Ser Gly Gly Met Gly Arg Leu Gln His
            20                  25                  30

His His Leu Pro Pro Val Ala Ala Asp Asp Pro Asp Arg Ser Phe Ser
        35                  40                  45

Cys Thr Tyr Cys Arg Arg Lys Phe Phe Ser Ser Gln Ala Leu Gly Gly
    50                  55                  60

His Gln Asn Ala His Lys Leu Glu Arg Ser Leu Ala Lys Arg Ser Arg
65                  70                  75                  80

Glu Leu Ser Ser Ala Val Ala Val Val Ser Ala Ala Ile Ser Ser Ser
                85                  90                  95

Ser Ala Ala Ala Ala Ala Pro Arg Ala Ala Ala Ser Glu Leu Cys
            100                 105                 110

Ser Trp Tyr Pro Thr Ala Gln Ala Gly Gly Pro Gly Asp Gln Ala Ala
        115                 120                 125

Ala Ala Ala Val Val Ser Trp Ile Ala Asp Gly Gly Arg Arg Tyr Ala
    130                 135                 140

Tyr Arg Val Gln Gln Ala Ala Ala Ser Asp Ala Asp Ile Asp
145                 150                 155                 160

Leu Ser Leu Arg Leu
                165

<210> SEQ ID NO 33
<211> LENGTH: 253
<212> TYPE: PRT
<213> ORGANISM: Arabidopsis thaliana

<400> SEQUENCE: 33

Met Gly Gly Arg Glu Asn Tyr Leu Asp Leu Asn Asn Leu Pro Asp Asp
1               5                   10                  15

-continued

```
Phe Ser Lys Asp Gly Asn Lys Gln Ala Leu Glu Glu Gly Ser Ser Ser
                20                  25                  30

Gly Gln Arg Lys Lys Gly Ser Lys Glu Gly Lys Asp Glu Ser Gly
            35                  40                  45

Lys Val Tyr Glu Cys Arg Phe Cys Ser Leu Lys Phe Cys Lys Ser Gln
 50                  55                  60

Ala Leu Gly Gly His Met Asn Arg His Arg Gln Glu Arg Glu Thr Glu
 65                  70                  75                  80

Thr Leu Asn Gln Ala Arg Gln Leu Val Tyr Arg Asn Asp Thr Ile Thr
                 85                  90                  95

Pro Pro Gly Ile Ser Pro Phe Gly Tyr His His Thr Thr Asp Pro Thr
            100                 105                 110

Ile Tyr Arg Ser Val Tyr Ser Ser Pro Met Ile Tyr Pro Gly Ser Ser
            115                 120                 125

Ser Thr Asn Leu Val Pro Gln Pro Pro Met Pro Pro Pro Pro Pro
130                 135                 140

Tyr Pro Tyr Ser Ser Asn Gln Tyr Ser Pro His Asn His Phe Asn Asp
145                 150                 155                 160

Tyr Tyr Leu Asn Pro Ser Phe Arg Gly Ser Arg Ser Ile Ser Pro Ser
                165                 170                 175

Pro Asn Leu Pro Thr Thr Thr Val Asp Tyr Met Ala Asp Ser Pro
            180                 185                 190

Val Glu Pro Gly Tyr Thr Cys Val Gly Ala Pro Ile Gly Pro Thr Gly
            195                 200                 205

Phe Pro Ile Arg Gly Pro Ser Ile Val Arg Ala Pro Leu Glu Pro Pro
210                 215                 220

Gln Gly Arg Asp Gly Asp Ala Ser Arg Gln Arg Leu Asp His Ser Leu
225                 230                 235                 240

Arg Phe Pro Ile Asn Arg Phe Gln Asp His His Ser Leu
                245                 250
```

<210> SEQ ID NO 34
<211> LENGTH: 226
<212> TYPE: PRT
<213> ORGANISM: Arabidopsis thaliana

<400> SEQUENCE: 34

```
Met Met Asp Arg Gly Glu Cys Leu Met Ser Met Lys Leu Arg Pro Met
  1               5                  10                  15

Val Thr Arg Pro Ser Ser Asp Gly Thr Leu Phe Trp Pro Phe Arg Glu
                 20                  25                  30

Glu Arg Ala Phe Ala Ser Ala Glu Glu Tyr Gly Gly Gly Gly Gly Cys
            35                  40                  45

Met Trp Pro Pro Arg Ser Tyr Ser Cys Ser Phe Cys Gly Arg Glu Phe
 50                  55                  60

Lys Ser Ala Gln Ala Leu Gly Gly His Met Asn Val His Arg Arg Asp
 65                  70                  75                  80

Arg Ala Arg Leu Lys Gln Gln Ser Leu Ser Pro Ser Ser Thr Asp Gln
                 85                  90                  95

Ala Thr Pro Pro Glu Cys Asp Arg Gln Gln Val Leu Asp Val Gly
            100                 105                 110

Ser Lys Val Leu Val Gln Glu Glu Thr Arg Lys Pro Asn Gly Thr Lys
            115                 120                 125

Arg Glu Ile Ser Asp Val Cys Asn Asn Asn Val Leu Glu Ser Ser Met
130                 135                 140
```

-continued

Lys Arg Tyr Glu His Asp Asn Gly Glu Val Lys Thr Asp Leu Ser Val
145                 150                 155                 160

Gly Leu Leu Ser Thr Glu Phe Asp Pro Arg Lys Lys Gln Leu Ile Asn
            165                 170                 175

Gly Ser Ser Ser Trp Lys Arg Ala Lys Thr Asp Val Ser Arg Phe
        180                 185                 190

Pro Met Met Leu Gly Leu Val Ile Gly Ile Ser Glu Ile Asn Gly His
            195                 200                 205

His Glu Glu Leu Asp Leu Glu Leu Arg Leu Gly Ala Asp Pro Pro Lys
210                 215                 220

Val Asn
225

<210> SEQ ID NO 35
<211> LENGTH: 175
<212> TYPE: PRT
<213> ORGANISM: Zea mays

<400> SEQUENCE: 35

Met Glu Gly Glu Asp Asp Gly Ala Gln Met Lys Leu Gln Gln Gln Gln
1               5                   10                  15

Gln Ser Pro Cys Ser Asp Asn Leu Ser Leu Ser Ala Ala Ser Ser Trp
            20                  25                  30

Leu Pro Pro Gln Val Arg Ser Ser Ser Ser Ser Tyr Thr Cys
        35                  40                  45

Gly Tyr Cys Lys Lys Glu Phe Arg Ser Ala Gln Gly Leu Gly Gly His
    50                  55                  60

Met Asn Ile His Arg Leu Asp Arg Ala Arg Leu Ile His Gln Gln Tyr
65                  70                  75                  80

Thr Ser His Arg Ile Ala Ala Pro His Pro Asn Pro Asn Pro Ser Cys
                85                  90                  95

Thr Ser Val Leu Asp Leu Glu Leu Ser Leu Ser Ser Leu Leu Ala His
            100                 105                 110

Gly Ala Ala Ser Ser Asp Gly Gly Leu Ser Val Pro Val Ala Lys Leu
        115                 120                 125

Ala Gly Asn Arg Phe Ser Ser Ala Ser Pro Thr Thr Lys Asp Val
130                 135                 140

Glu Gly Lys Asn Leu Glu Leu Arg Ile Gly Ala Cys Ser His Gly Asp
145                 150                 155                 160

Gly Ala Glu Glu Arg Leu Asp Leu Gln Leu Arg Leu Gly Tyr Tyr
            165                 170                 175

<210> SEQ ID NO 36
<211> LENGTH: 204
<212> TYPE: PRT
<213> ORGANISM: Arabidopsis thaliana

<400> SEQUENCE: 36

Met Glu Arg Ser Asn Ser Ile Glu Leu Arg Asn Ser Phe Tyr Gly Arg
1               5                   10                  15

Ala Arg Thr Ser Pro Trp Ser Tyr Gly Asp Tyr Asp Asn Cys Gln Gln
            20                  25                  30

Asp His Asp Tyr Leu Leu Gly Phe Ser Trp Pro Pro Arg Ser Tyr Thr
        35                  40                  45

Cys Ser Phe Cys Lys Arg Glu Phe Arg Ser Ala Gln Ala Leu Gly Gly
    50                  55                  60

```
His Met Asn Val His Arg Arg Asp Arg Ala Arg Leu Arg Leu Gln Gln
 65                  70                  75                  80

Ser Pro Ser Ser Ser Ser Thr Pro Ser Pro Pro Tyr Pro Asn Pro Asn
                 85                  90                  95

Tyr Ser Tyr Ser Thr Met Ala Asn Ser Pro Pro Pro His His Ser Pro
            100                 105                 110

Leu Thr Leu Phe Pro Thr Leu Ser Pro Pro Ser Ser Pro Arg Tyr Arg
            115                 120                 125

Ala Gly Leu Ile Arg Ser Leu Ser Pro Lys Ser Lys His Thr Pro Glu
            130                 135                 140

Asn Ala Cys Lys Thr Lys Lys Ser Ser Leu Leu Val Glu Ala Gly Glu
145                 150                 155                 160

Ala Thr Arg Phe Thr Ser Lys Asp Ala Cys Lys Ile Leu Arg Asn Asp
                165                 170                 175

Glu Ile Ile Ser Leu Glu Leu Glu Ile Gly Leu Ile Asn Glu Ser Glu
                180                 185                 190

Gln Asp Leu Asp Leu Glu Leu Arg Leu Gly Phe Ala
            195                 200
```

ZINC FINGER PROTEINS EXPRESSED IN PLANT MERISTEM

CROSS-REFERENCE TO RELATED APPLICATIONS

This application claims the benefit of, and hereby incorporates by reference U.S. Provisional Application No. 60/598,726, filed Aug. 4, 2004.

BACKGROUND OF THE INVENTION

1. Field of the Invention

The invention relates generally to zinc binding proteins, and more specifically to a zinc finger protein that is expressed in plant meristem and has the characteristics of a meristem specific transcription factor, to methods of using the zinc finger protein to regulate gene expression and to modulate plant growth and development, and to a transgenic plant containing in its genome a transgene, which includes a polynucleotide encoding the zinc finger protein, or a nucleotide sequence complementary to the encoding polynucleotide.

2. Background Information

Technologic developments continually advance in an effort to address the need to increase plant yield in order to feed the expanding world population. Biotechnology is playing an increasingly important role in this effort by providing, for example, plants having increased resistance to drought and insect infestation. For many plants such as corn, rice, and soybean, seed provides the source of food products, including grain, and can be eaten directly or processed into flour, milk products, and the like. For other plants, edible seeds, roots, stems, leaves, bulbs and tubers provide a source of vegetables. Fruits, which are the ripened reproductive body of plants, also are an important food source.

Because many foods are derived, either directly or indirectly, as a result of plant flowering, methods for increasing flowering efficiency and numbers of flowers produced of plants can result in increased yield. An important aspect of plant flowering relates to the regulation of meristem activity in the production of florets. As such, an understanding of the factors that influence the activity of apical, inflorescence, and floral meristems can provide tools for manipulating the flowering characteristics of a plant. Further, while providing a means to increase yield of crop plants, such tools also can be useful in the ornamental plant industry, providing, for example, a means to increase the number and/or size of flowers produced by a plant.

Genes that regulate floral organ formation have been identified, including, for example, genes that control the establishment of floral organ identity, and the products of many of these genes have been identified as transcription factors, or as putative transcription factors based on their structural features. Evidence indicates that gene expression leading to the floral organ formation is regulated, at least in part, at the transcriptional level by a hierarchical expression of homeotic genes, including transcription factors. As such, many of the target genes of the homeotic genes can encode transcription factors that, in turn, regulate downstream events, thus providing specialized roles in flower development.

Zinc finger proteins containing two conserved cysteine residues and two conserved histidine residues (C2H2 zinc finger proteins) comprise a family of transcription factors that have homeotic functions, including, for example, Kruppel and Hunchback, which are involved in transcriptional control of development in *Drosophila*. In plants, the ZFP-2 family of transcription factors may represent a class of transcription factors that control developmental processes.

Zinc finger domains comprise a portion of zinc finger proteins that specifically bind target DNA sequences (e.g., gene promoters). Since the initial description of zinc finger domains in the *Xenopus* transcription factor TFIIIA, the domains have been identified as a common feature of many nucleic acid binding proteins. Zinc finger domains generally are about 25 to 30 amino acid residues in length, and contain the conserved C2H2 motif (C—X2-C—X12-H—X3-H (SEQ ID NO:27), where X is any amino acid residue and the number indicates the number of X residues). Further, the X residues generally are not random; for example, the 12 residues between the second Cys and the first H is generally are polar and basic, and implicate this region as directly involved in nucleic acid binding. Zinc ion is a crucial component of the zinc finger domain tertiary structure. All zinc finger domains bind 1 atom of zinc in a tetrahedral array, yielding a finger like projection that can interact with nucleotides in the major groove of a nucleic acid molecule.

The identification of transcription factors involved in floral organ identity provides a means to manipulate whether a plant flowers or does not flower. However, such factors do not allow one to manipulate the number of flowers or other organs on a plant and, therefore, are limited in their use for increasing plant yield. Thus, a need exists for compositions and methods that can affect plant tissue determination such as the zinc finger protein of the present invention that is expressed in plant meristem.

Nearly all crops may be benefited by the manipulation of growth and development characteristics. As such, mutations in the reception and signal transduction of gibberellins leading to dwarf-like plants have been described as advantageous in many crop plants (U.S. Pat. No. 6,307,126; U.S. Pat. No. 6,762,348; U.S. Pat. No. 6,830,930; U.S. Pat. No. 6,794,560). This was especially true in high-yielding, semi-dwarf wheat varieties where the reduced plant stature was most advantageous in increasing grain production per plant and superior straw strength. The shorter, stronger straw greatly reduces the losses resulting from lodging or flattening of the standing wheat plants by rain and high winds. In addition a concomitant increase in harvest index was evident shifting more photoassimilates from vegetative growth components to the grain.

Specific genes that regulate the expression of GA biosynthetic pathway genes are the subject of continued research. Much work has been published on the genes involved in sensing GA or transducing the GA signal downstream to affect plant growth and development. One known direct effect on controlling the expression of a biosynthetic enzyme in the GA pathway involves a KNOX-like homeodomain containing a transcription factor. In tobacco, the KNOX-like NTH15, was shown to repress the GA-20 oxidase gene, Ntc12, in shoot apical meristems as a mechanism to repress aspects of cellular differentiation in the meristem (Sakamoto, T., et al., KNOX homeodomain protein directly suppresses the expression of a gibberellin biosynthetic gene in the tobacco shoot apical meristem. Genes Dev, 2001. 15: 581-90). Evidence gathered indicates that the ZmZFP2 gene affects plant growth and development in a similar manner. Ectopic expression of ZmZFP2 in maize reduces plant stature (markedly in more strongly expressed lines) while inhibition of ZmZFP2 gene by RNAi enhances plant height in a statistically significant manner.

SUMMARY OF THE INVENTION

The present invention is based, in part, on the identification of proteins, referred to herein as *Zea mays* zinc finger protein-2 ("ZmZFP2") polypeptides, that are expressed in meristem in *Zea mays* (maize; corn) and share homology with the ZFP2 zinc finger transcription factor family of proteins, and of orthologs of the ZmZFP2 proteins (collectively, "ZFP2-like" proteins). As disclosed herein, ZmZFP2 gene expression is active in maize meristems at very low levels. As such, ectopic expression of a ZmZFP2-like transcription factor could negatively regulate, inhibit, suppress or reduce the phytohormone gibberellic acid (GA) synthesis and lead to a decrease in plant stature or dwarf phenotype. By gibberellic acid or GA is meant a diterpenoid molecule acting as an active phytohormone as shown in the U.S. Pat. No. 6,307,126. Examples of biological activity may include, but are not limited to, stimulation of cell elongation, leaf senescence, elicitation of the cereal aleurone alpha-amylase response or repression of maize ear elongation.

As mentioned above, the ZmZFP2 gene is active in meristem tissue, especially maize ear tip meristems, while florets are being produced, and is down-regulated as the meristem begins to terminate. As such, ectopic expression of a ZFP2-like protein, when it would otherwise be down-regulated, provides a means to increase the number of florets in a plant by delaying termination, thus providing a means to increase yield. Conversely, inhibition of ZFP2-like gene expression in meristem giving rise to developing male organs or female organs, when the gene (e.g., a ZmZFP2 gene) otherwise would be expressed, can ablate the respective floral structure, thus providing a means to generate "supermale" and "superfemale" plants, which produce only male structures or only female structures, respectively.

Accordingly, the present invention relates to isolated nucleic acid molecules encoding ZFP2-like zinc-finger polypeptides, including ZmZFP2 haplotypes and ZMZFP2 orthologs, and to peptide portions of a ZFP2-like peptide. Such nucleic acid molecules can be single stranded or double stranded, and can be DNA or RNA or a hybrid thereof. As such, the nucleic acid molecules of the invention include, for example, a nucleotide sequence that, when expressed, can encode a ZmZFP2 polypeptide, or can comprise the sequence complementary to the coding strand (e.g., an antisense molecule). Further, the invention provides nucleic acid molecules containing two or more nucleotide sequences comprising all or a portion of a nucleic acid molecule encoding a ZmZFP2 polypeptide. For example, the nucleic acid molecule can include a portion of a coding sequence and, in reverse orientation, the corresponding complementary sequence, such that the construct comprises an inverted repeat. Where such a nucleic acid molecule comprises a single stranded RNA molecule, or where the nucleic acid molecule is a DNA molecule from which a single stranded RNA molecule is transcribed, the RNA can self hybridize to form a hairpin structure, which, for example, can mediate RNA interference (RNAi).

In one embodiment, an isolated nucleic acid molecule of the invention comprises a ZmZFP2 haplotype, including, for example, a polynucleotide encoding a ZmZFP2 polypeptide having an amino acid sequence as set forth in any of SEQ ID NOS: 2, 4, 6, 8, 10, 12, and 14. Such polynucleotides are exemplified by the coding sequence of the polynucleotide set forth in SEQ ID NOS: 1, 3, 5, 7, 9, 11, and 13, respectively, and can further include one or more non-coding nucleotides, which can be 5' and/or 3' untranslated and/or untranscribed sequences (e.g., gene regulatory elements) as set forth in SEQ ID NOS: 1, 3, 5, 7, 9, 11 and 13, including the full length disclosed sequences. ZmZFP2 haplotypes are characterized, in part, in that they encode polypeptides that share greater than about 70% (e.g., 70%, 75%, 80%, 85%, 90%, 92%, 95%, or 98%) amino acid sequence identity with SEQ ID NO:4 or SEQ ID NO:6 over its full length.

In another embodiment, the isolated nucleic acid molecule includes a polynucleotide encoding a peptide portion of a ZmZFP2 polypeptide, or a polynucleotide fully complementary thereto. In one aspect of this embodiment, the encoded peptide portion of the ZmZFP2 polypeptide is at least an octapeptide portion of a ZmZFP2 polypeptide (i.e., at least 8 contiguous amino acids; e.g., 8, 9, 10, 11, 12, or more), for example, an octapeptide portion, of a ZmZFP2 polypeptide as set forth in SEQ ID NO:4 or SEQ ID NO:6, or of a ZmZFP2 haplotype having at least 90% sequence identity to SEQ ID NO:4 or SEQ ID NO:6. In another aspect of this embodiment, the encoded octapeptide portion of the ZmZFP2 polypeptide does not consist of an amino acid sequence corresponding to amino acid residues 57 to 73 of SEQ ID NO:4, or a portion thereof, or amino acid residues 58 to 74 of SEQ ID NO:6, or a portion thereof. As such, an at least octapeptide portion of a ZmZFP2 polypeptide according to this aspect of the invention does not consist solely of a C2H2 domain.

In a further aspect of this embodiment, the polynucleotide encodes a peptide portion of the ZmZFP2 polypeptide having specific DNA binding activity. Such DNA binding domains are characterized in that they specifically bind a defined target DNA sequence, and have an amino acid sequence that is different from those of known zinc finger protein DNA binding domains. In yet another aspect, the polynucleotide encodes a peptide portion of a ZmZFP2 polypeptide that has transcription activating activity. Such polynucleotides can be useful, for example, for constructing recombinant nucleic acid molecules encoding chimeric transcription factors, e.g., a fusion protein comprising a DNA binding domain of ZmZFP2 and a transcription activation domain of a transcription factor.

In still another embodiment, the isolated nucleic acid molecule comprises a nucleotide sequence that is complementary to a polynucleotide encoding a ZmZFP2 haplotype (e.g., SEQ ID NOS: 2, 4, 6, 8, 10, 12, or 14) or a peptide portion thereof. In one aspect, the nucleotide sequence is complementary to a polynucleotide encoding the entire amino acid sequence set forth in any of SEQ ID NOS: 2, 4, 6, 8, 10, 12, or 14, for example, a nucleotide sequence complementary to nucleotides 35 to 533 of SEQ ID NO: 1, which comprises the ATG start codon through the TAA stop codon; or a nucleotide sequence complementary to the full length of SEQ ID NO: 1 (or a corresponding nucleotide sequence of any of SEQ ID NOS: 3, 5, 7, 9, 11, and 13). In another aspect, the nucleotide sequence is complementary to a polynucleotide encoding an octapeptide portion of a ZmZFP2 polypeptide as disclosed herein, or is complementary to a polynucleotide encoding peptide portion of any of SEQ ID NOS: 2, 4, 6, 8, 10, 12, or 14 having specific DNA binding activity or transcription activating activity. In still another aspect of this embodiment, nucleotide sequences of SEQ ID NO: 1, 3, 5, 7, 9, 11, and 13, or encoding SEQ ID NO: 2, 4, 6, 8, 10, 12, or 14, are contemplated for use as antisense molecules, ribozymes, and the like, provided the molecule specifically affects expression of a ZmZFP2 haplotype or ZmZFP2 ortholog without substantially affecting the expression of other genes that encode polypeptides containing a C2H2 domain.

A nucleic acid molecule of the invention (or useful in a method of the invention) can be operatively linked to one or more heterologous nucleotide sequences of interest. The heterologous nucleotide sequence(s) can be, for example, one or a plurality of regulatory elements, which can be translational regulatory elements (e.g., a ribosome recognition/binding sequence and/or an internal ribosome entry site) and/or transcriptional regulatory elements (e.g., a promoter, an enhancer, and/or a terminator). Where a heterologous nucleotide sequence is a promoter, it can be a constitutive promoter, an inducible promoter, a tissue specific promoter, or a developmental stage specific promoter, including, for example, an environmentally regulated promoter, an organelle specific promoter, a cell specific promoter, a promoter active only in male plant reproductive tissues or in female plant reproductive tissues (e.g., an anther specific promoter, pollen specific promoter, or ovary specific promoter), or a meristem specific promoter (e.g., an apical meristem specific promoter, an inflorescence meristem specific promoter, and/or a floral meristem specific promoter).

A heterologous nucleotide sequence operatively linked to a nucleic acid molecule comprising a ZmZFP2 haplotype or an ortholog thereof can encode a second (or more) polypeptide(s), in addition to the encoded ZmZFP2 polypeptide or ortholog (or peptide portion thereof). Such heterologous nucleotide sequences can be operatively linked such that the encoded polypeptides, including the ZmZFP2 polypeptide (or, in aspects of the present invention, ZFP2-like protein), can be co-expressed as a fusion protein or as separate polypeptides, as desired. Such an operatively linked heterologous nucleotide sequence can encode, for example, a cell localization domain (e.g., a signal peptide, or a nuclear localization domain), a peptide tag (e.g., a c-myc epitope) or other detectable polypeptide (e.g., a fluorescent protein such as a green fluorescent protein, or an enzyme such as luciferase), or a polypeptide that confers a selective advantage (or disadvantage) upon a cell containing the polypeptide (e.g., phosphinothricin acetyltransferase, which confers resistance to phosphinothricin).

Where the nucleic acid molecule comprises an inverted repeat of all or a portion of a nucleic acid molecule encoding the ZmZFP2 or the ZmZFP2-like protein, a heterologous nucleotide sequence operatively linked to the nucleic acid molecule can comprise a spacer nucleotide sequence, which, for example, provides sufficient spacing between the repeat units such that self-hybridization of a single stranded form of the nucleic acid molecule (e.g., RNA) is not constrained. With respect to an RNA molecule of the invention, a heterologous nucleotide sequence also can be a nucleotide sequence that confers ribozyme activity.

A heterologous nucleotide sequence operatively linked to a nucleic acid molecule encoding a ZmZFP2 haplotype or, in aspects of the invention, ZmZFP2 ortholog, also can comprise a vector, which can be a cloning vector, targeting vector, expression vector, or the like. An expression vector, or nucleotide sequences of an expression vector, can be a plant expression vector, for example, a vector based on an *Agrobacterium* Ti plasmid or Ri plasmid. Accordingly, the invention provides a vector containing a nucleic acid molecule encoding a ZFP-2 like polypeptide, or peptide portion thereof, and/or a corresponding complementary sequence, for example, a vector containing a ZmZFP2 haplotype or peptide portion or complement thereof.

The invention also provides a host cell containing a nucleic acid molecule encoding a ZmZFP2 or ZmZFP2-like polypeptide, or peptide portion thereof, wherein the nucleic acid molecule can, but need not, be contained in a vector. The host cell can be any cell, including a prokaryotic cell or eukaryotic cell, and can be a bacterial cell, an insect cell, an animal cell, or a plant cell. As such, a host cell can be useful for maintaining or expanding the nucleic acid molecule of the invention, or for expressing an encoded product of the nucleic acid molecule (either RNA or a polypeptide), including for obtaining desired amounts of the RNA or protein or for characterizing the function of the RNA or protein in the host cell.

The invention further relates to a transgenic non-human organism containing, in its genome, an exogenously introduced nucleic acid molecule encoding a ZFP2-like polypeptide, particularly a ZmZFP2 haplotype, or a peptide portion thereof, and/or a corresponding complementary sequence. In one embodiment, the transgenic organism is a transgenic plant that contains, integrated in its genome, a nucleic acid molecule encoding a ZmZFP2 polypeptide, or peptide portion thereof, or encoding a nucleotide sequence complementary thereto. The transgenic plant can be any type of plant, including, for example, a monocotyledonous plant (monocot) or a dicotyledonous plant (dicot), and a gymnosperm or angiosperm. In aspects of the invention, the transgenic plant is maize, rice, wheat, barley, soybean, or sorghum. The invention also provides cells and cuttings of such transgenic plants, isolated seed produced by the transgenic plants, and progeny plants generated from the cells, cuttings, or seed of the transgenic plants.

In one aspect, the nucleic acid molecule encoding ZmZFP2 haplotype or ortholog in a transgenic plant of the invention is ectopically expressed in cells in which it is not normally expressed, or at a time or developmental stage at which it, is not normally expressed. Ectopic expression can be effected, for example, by operatively linking the ZmZFP2 nucleic acid molecule to a promoter having the desired characteristics. For example, a ZmZFP2 nucleic acid molecule can be operatively linked to an inducible promoter, such that ZmZFP2 can be expressed upon contact of a transgenic plant with the appropriate inducing agent, or can be operatively linked to an after floral transition to tassel-type meristem promoter, such that ZmZFP2 is expressed ectopically in meristems destined to produce tassels. This would increase numbers of developing anthers and overall size of the tassel. The disclosure indicates that, by up-regulation of ZmZFP2 in meristem cells destined, for example, to give rise to male organs, it would increase the number of anthers produced in the tassels by extending meristem function to produce more spikelets (leads to anther development). It is the downregulation or inactivation of the ZmZFP2-like gene in meristem cells destined to be the male organ that would terminate the male development earlier than normal resulting in female only or 'superfemale' trait. The opposite can be said if the ZmZFP2 is downregulated or inactivation in meristem cells destined for the female development, causing early arrest in ear development and leading to male only or 'supermale' trait. There is evidence to suggest that removing the tassel/anthers from developing plants leads to significant increase in yield if separate pollinators are available.

The present invention also relates to an isolated nucleic acid molecule encoding ZmZFP2 ortholog or homolog, which is characterized, in part, in that it shares at east about 50% (e.g., 50%, 60%, 70% or greater) amino acid sequence identity with a ZmZFP2 polypeptide (e.g., SEQ ID NO: 2, 4, 6, 8, 10, 12 or 14) when the encoded polypeptides are compared over their entire lengths, and allowing for maximum sequence identity (e.g., by inserting spaces to maintain homology). An ortholog of a ZmZFP2 haplotype can be a rice, soybean, wheat, barley, or other plant ortholog, for example, a rice ortholog (see SEQ ID NOS: 15 and 16) or an *Arabidopsis* ortholog (see SEQ ID NOS: 17 and 18). A ZmZFP2 homolog can be a sequence of a related gene of a mammal or other organism. The present invention also provides an isolated ZmZFP2 ortholog or homolog, and further provides a transgenic plant containing, integrated in its genome, an exogenously introduced nucleic acid molecule encoding a ZmZFP2 ortholog or homolog.

The present invention also relates to an isolated ZmZFP2 polypeptide, which has an amino acid sequence that is at least 70% (e.g., 70%, 75%, 80%, 90%, or more) identical to SEQ ID NO: 4, and to a peptide portion of ZmZFP2 polypeptide, wherein the peptide contains at least eight contiguous amino acids of an exemplified ZmZFP2 polypeptide (e.g., SEQ ID NO: 2, 4, 6, 8, 10, 12, or 14), including at least one (e.g., 1, 2, 3, or 4) residue of amino acid residues 1 to 56 and 74 to 165 of SEQ ID NO: 4 (or SEQ ID NO: 8, 10 or 14), or at least one residue of amino acid residues 1 to 57 and 75 to 166 of SEQ ID NO: 6 (or SEQ ID NO: 12); or wherein the peptide portion includes at least eight contiguous amino acids of the sequence set forth as amino acid residues 1 to 58 and 72 to 165 of SEQ ID NO: 4, or at least eight contiguous amino acids of the sequence set forth as amino acid residues 1 to 59 and 73 to 166 of SEQ ID NO: 6; or wherein the peptide portion is at least an octapeptide portion of the ZmZFP2 polypeptide, provided the octapeptide does not consist of amino acid residues 57 to 73 of SEQ ID NO: 4, or a portion thereof, or of amino acid residues 58 to 74 of SEQ ID NO: 6, or a portion thereof. In one embodiment, the peptide portion of a ZmZFP2 polypeptide has DNA binding activity, transcription activating activity, or both.

The invention also provides a fusion protein (chimeric protein), wherein a ZmZFP2 polypeptide (or peptide portion) or, in various aspects, a ZmZFP2 ortholog (or peptide portion thereof), is operatively linked to a heterologous peptide. Such fusion proteins are exemplified by peptide portion of a ZmZFP2 haplotype comprising the zinc finger (DNA binding) domain operatively linked to a transcription activation domain of a heterologous polypeptide; and by a ZmZFP2 transcription activation domain operatively linked to a DNA binding domain of a heterologous polypeptide.

The present invention further relates to an antibody that specifically binds a ZmZFP2 polypeptide, or peptide portion thereof, as well as to antigen binding fragments of such antibodies. An antibody of the invention is characterized, in part, in that it does not bind to an epitope formed solely by the C2H2 domain of the ZmZFP2 haplotype (e.g., amino acid residues 57 to 73 of SEQ ID NO:4). An antibody of the invention can be a monoclonal antibody, or can comprise polyclonal antibodies, which can be isolated antibodies, isolated serum (antiserum) containing the antibodies, an immunoglobulin fraction of such serum, and the like. In addition, an antibody of the invention can be a humanized antibody, a chimeric antibody, a single chain antibody, or the like. An antigen binding fragment of an antibody of the invention can be an Fab fragment, an Fd fragment, an Fv fragment, an F(ab)'$_2$ fragment, or any other fragment that maintains specific ZmZFP2 binding activity.

The present invention also relates to a transgenic plant, which contains, integrated in its genome, a transgene comprising an expressible polynucleotide that encodes or is complementary to a nucleotide sequence that encodes a ZmZFP2 haplotype or, in various aspects, an ortholog thereof, or a peptide portion of the ZFP2-like polypeptide. Preferably, the expressible polynucleotide is operatively linked to a transcriptional regulatory element that is active in cells of a plant. As such, the transcriptional regulatory element can include, for example, a promoter, which can be a constitutive, inducible, tissue specific, or developmental stage specific promoter The transcriptional regulator element can also include an enhancer.

In one embodiment, the transgenic plant contains a polynucleotide encoding a ZmZFP2 polypeptide, which is, or can be, ectopically expressed in cells of the plant. For example, the ZmZFP2 polypeptide can be ectopically expressed in floral meristem cells at a time that endogenous ZmZFP2 gene expression would be down-regulated (e.g., when the meristem begins to terminate), thereby increasing the number of florets in the transgenic plant as compared to a corresponding wild type plant (i.e., a plant lacking ectopic expression of ZmZFP2). In another embodiment, the transgenic plant contains a polynucleotide encoding a ZmZFP2 ortholog that is (or can be) ectopically expressed in cells of the plant.

A transgenic plant of the invention can further include, in its genome, an exogenous polynucleotide in addition to the introduced nucleic acid molecule encoding the ZFP2-like polypeptide, including, for example, an exogenous polynucleotide encoding a selectable marker, which confers a selective advantage or detectable phenotype upon the transgenic plant. In one embodiment, the exogenous polynucleotide is operatively linked to the polynucleotide encoding a ZmZFP2 polypeptide, or to the complementary sequence. In one aspect of this embodiment, ZmZFP2 nucleotide sequences flank the polynucleotide encoding the selectable marker, thus providing a targeting vector useful for effecting homologous recombination with the endogenous plant ZmZFP2 gene.

The present invention also relates to a method of altering tissue development in a plant by modulating ZFP2 protein activity in meristem cells of the plant, wherein the ZFP2 protein regulates differentiation of the meristem cells, thereby altering tissue development in the plant. As disclosed herein, expression of a polynucleotide encoding a ZmZFP2 haplotype (see, e.g., SEQ ID NOS: 1 to 14) or a ZmZFP2 ortholog, for example, a rice ortholog (see, e.g., SEQ ID NOS: 15 and 16) or an *Arabidopsis* ortholog (see, e.g., SEQ ID NOS: 17 and 18), or a polynucleotide complementary thereto, can be used to alter tissue development by modulating ZFP2 protein activity in cells that comprise or give rise to the tissue.

ZFP2-like protein activity can be modulated, for example, by expressing an exogenous polynucleotide in the meristem cells, wherein the exogenous polynucleotide comprises an expressible nucleotide sequence. For example, the expressible nucleotide sequence encodes an exogenous ZmZFP2 polypeptide or peptide portion thereof (e.g., a peptide having the activity of a full length ZmZFP2 polypeptide), thus increasing the amount of ZmZFP2 in the cell and, therefore, ZmZFP2 activity in the meristem cells. According to this embodiment, differentiation (or termination) of the meristems is delayed or inhibited due to expression of the ZmZFP2 polypeptide. For example, where the meristem cells comprise floral (inflorescence) meristem, a plant comprising the cells can have an increased number of florets as compared to a corresponding plant lacking or having normal ZmZFP2 activity.

Expression of the expressible nucleotide sequence also can decrease the activity of the ZFP2 protein in the meristem cells of a plant, thereby increasing differentiation of the meristem cells and ablating floral development. For example, the expressible nucleotide sequence can encode a peptide portion of a ZmZFP2 haplotype or ortholog having dominant negative activity, wherein expression of the peptide decreases ZmZFP2 activity in the meristem cells. The expressible nucleotide sequence also can comprises a nucleic acid molecule complementary to a polynucleotide encoding a ZmZFP2 haplotype or ortholog, or peptide portion thereof, whereby expression of the nucleic acid molecule reduces or inhibits ZmZFP2 polypeptide activity in the cells. Such nucleic acid molecules are exemplified by an antisense molecule, a ribozyme, a small interfering RNA (RNAi), an a co-suppressor RNA.

An exogenous polynucleotide useful in a method of the invention generally includes, in operative linkage with the expressible nucleotide sequence, one or more regulatory elements that can effect transcription, translation, intracellular localization of an RNA and/or polypeptide encoded by the expressible nucleotide sequence. A transcriptional regulatory element can be selected, for example, based on its ability to direct expression of the operatively linked expressible nucleotide sequence at a specific time (e.g., at a particular stage of development), in one or a few specific tissues (e.g., male or female reproductive tissues), or based on its ability to be induced as desired using an appropriate inducing agent, or can be a constitutively active promoter.

In one embodiment, the plant, in which tissue development can be altered, is a transgenic plant, which contains, an exogenous polynucleotide integrated in its genome, wherein the exogenous polynucleotide comprises a nucleotide sequence that encodes a ZmZFP2 haplotype or ortholog; or that encodes a peptide portion of the ZFP2-like polypeptide; or that is complementary to a nucleotide sequence encoding a ZFP2-like polypeptide, or a peptide portion thereof, and wherein the nucleotide sequence is expressible in meristem progenitor cells or cells derived therefrom. For example, the nucleotide sequence of the exogenous polynucleotide can be a nucleotide sequence encoding a ZmZFP2 haplotype or ortholog as exemplified in SEQ ID NOS: 2, 4, 6, 8, 10, 12, 14, 16, or 18, or a peptide portion thereof, or can be a portion of the nucleotide sequence as exemplified in SEQ ID NOS: 1, 3, 5, 7, 9, 11, 13, 15, or 17, or a nucleotide sequence complementary thereto.

The present invention also relates to a method of generating a transgenic plant, wherein the development of tissues from meristem in the transgenic plant can be manipulated. Such a method can be performed, for example, by transforming a plant cell with a transgene that includes an expressible polynucleotide encoding a ZmZFP2 haplotype, or peptide portion thereof, or a polynucleotide complementary thereto; and producing a plant from the transformed plant cell, whereby meristem progenitor cells of the plant, or cells derived therefrom, contain the expressible polynucleotide stably integrated in its genome. Upon expression of the expressible polynucleotide at a desired time in meristem of the transgenic plant, differentiation of the meristem into a plant tissue can be induced or can be delayed or inhibited. For example, by inducing expression of an expressible polynucleotide encoding a ZmZFP2 haplotype, or an ortholog or homolog thereof, in maize ear meristem, an increased number of florets can be obtained, thus increasing the potential yield of the transgenic plant as compared to a corresponding wild type plant.

According to the present method, the plant cell transformed with the transgene can comprise of protoplast tissue, gamete producing cells, or any other plant cells from which a plant can be generated. Further, the plant cell can be a cell of any plant of interest, including crop plants and ornamental plants, for example, a wheat, maize, oat, rice, barley, sorghum, orchid, rose, or carnation plant. Accordingly, the invention provides a transgenic plant produced by the method of the invention, for example, a transgenic plant in which differentiation of meristem to ovary is inhibited (i.e., a supermale plant) or a transgenic plant in which differentiation of meristem to anther is inhibited or pollen production is inhibited (i.e., a superfemale plant).

The expressible polynucleotide of a transgene useful in a method of producing a transgenic plant generally is operatively linked to one or more regulatory elements, including, for example, one or more transcriptional regulatory elements and/or translational regulatory elements. In particular, the expressible polynucleotide can be operatively linked to a transcriptional promoter, which can be a constitutive promoter, inducible promoter, environmentally regulated promoter, developmental stage specific promoter, or a tissue specific promoter such as an anther specific promoter, a stigma specific promoter, a pollen specific promoter, an ovary specific promoter, or a meristem specific promoter. The meristem cells containing the transgene, and in which the expressible polynucleotide can be expressed, can be shoot meristem, root meristem, lateral shoot or floral meristem, inflorescence meristem, or can be cells that give rise to meristem cells or cells that are derived from meristem.

A method of producing a transgenic plant can further include crossing the (first) transgenic plant with a second plant, which can be a wild type plant or a second transgenic plant, which can be the same or different from first transgenic plant. In one embodiment, the transgenic plant produced according to a method of the invention is crossed with a plant having a genotype different from the transgenic plant, whereby hybrid plants are generated. Accordingly, the invention provides a transgenic plant produced by the method of the invention. Accordingly, the invention also provides a hybrid plant generated by such a method, as well as seed produced by such a hybrid plant.

The present invention also relates to a method of identifying an agent that modulates the activity of a ZmZFP2 haplotype. The activity that is modulated can be any activity of the ZmZFP2 haplotype, including, for example, DNA binding activity, transcription activation activity, or transcriptional activity, and particularly the ZmZFP2 activity associated with meristem differentiation. Such a method can be performed, for example, by contacting a ZmZFP2 protein (or a peptide portion having the activity) with a test agent under conditions suitable for manifestation of the activity; and detecting a difference in ZmZFP2 mediated activity in the presence of the test agent as compared to the activity in the absence of the test agent, wherein a difference in activity identifies the test agent as an agent that modulates ZmZFP2 polypeptide activity. Where the method is practiced to screen for agents that can modulate plant meristem function, the test agent can be contacted with any ZmZFP2 haplotype, including, for example, a ZmZFP2 polypeptide having an amino acid sequence as set forth in any of SEQ ID NOS: 2, 4, 6, 8, 10, 12, or 14, or encoded by a polynucleotide as set forth in any of SEQ ID NOS: 1, 3, 5, 7, 9, 11, and 13.

The test agent can be any agent as desired, including a physical, chemical or biological agent. For example, the agent can be a peptide, peptidomimetic, polynucleotide, or small organic molecule. Further, the method is amenable to being practiced in a high throughput format, for example, by contacting a plurality of ZmZFP2 polypeptides, which can be the same or different, and/or various peptide portions thereof, and can, but need not, include ZmZFP2 orthologs or homologs or other ZFP2 proteins, with one or more of agents, for example, with one or more agents of a library of agents. Accordingly, the invention also provides an agent that modulates ZmZFP2 protein activity identified by such a method.

BRIEF DESCRIPTION OF THE DRAWINGS

FIG. 1. Alignment of the amino acid sequences of ZFP2-like proteins encoded by the nucleotide sequences derived from the *Arabidopsis* ZFP cDNA clone, AAA87298, the corn ZmZFP2-like clone cep7.pk0020.c2:fis (SEQ ID NO: 2), and rice predicted amino acid sequences from Beijing Rice Genomic project (labeled as "scaffold######_#" where # is a number). The consensus sequence is the identical amino acids across the majority of entries. The red-boxed amino acids are identical over all sequences. The blue amino acids are identical across a majority of sequences. The green amino acids are functionally conserved amino acids to the consensus sequence while the grey-boxed amino acids are blocks of similar amino acids to the consensus sequence. Dashes are used by the program to maximize the alignment of the sequences.

FIG. 5. An amino acid alignment of several key CCHH-type zinc finger genes from *arabidopsis* as compared to the ZmZFP2 sequence, was performed using the CLUSTAL W multisequence alignment program (Vector NTI Software Suite version 9.1, Invitrogen, Carlsbad, Calif., USA). (SEQ ID NO: 36 depicts the amino acid sequence of the *arabidopsis* SUPERMAN gene, SEQ ID NO: 33 *arabidopsis* JAGGED gene, SEQ ID NO: 34 *arabidopsis* RABBIT EARS gene, SEQ ID NO: 35 is the amino acid sequence of the maize RAMOSA1 gene, SEQ ID 30 and SEQ ID 31 refer to *arabidopsis* ZINC FINGER PROTEIN 2 and 7, respectively (NCBI Genbank protein entries AAA87298 and AAA87303).

DETAILED DESCRIPTION OF THE INVENTION

Figure 2:
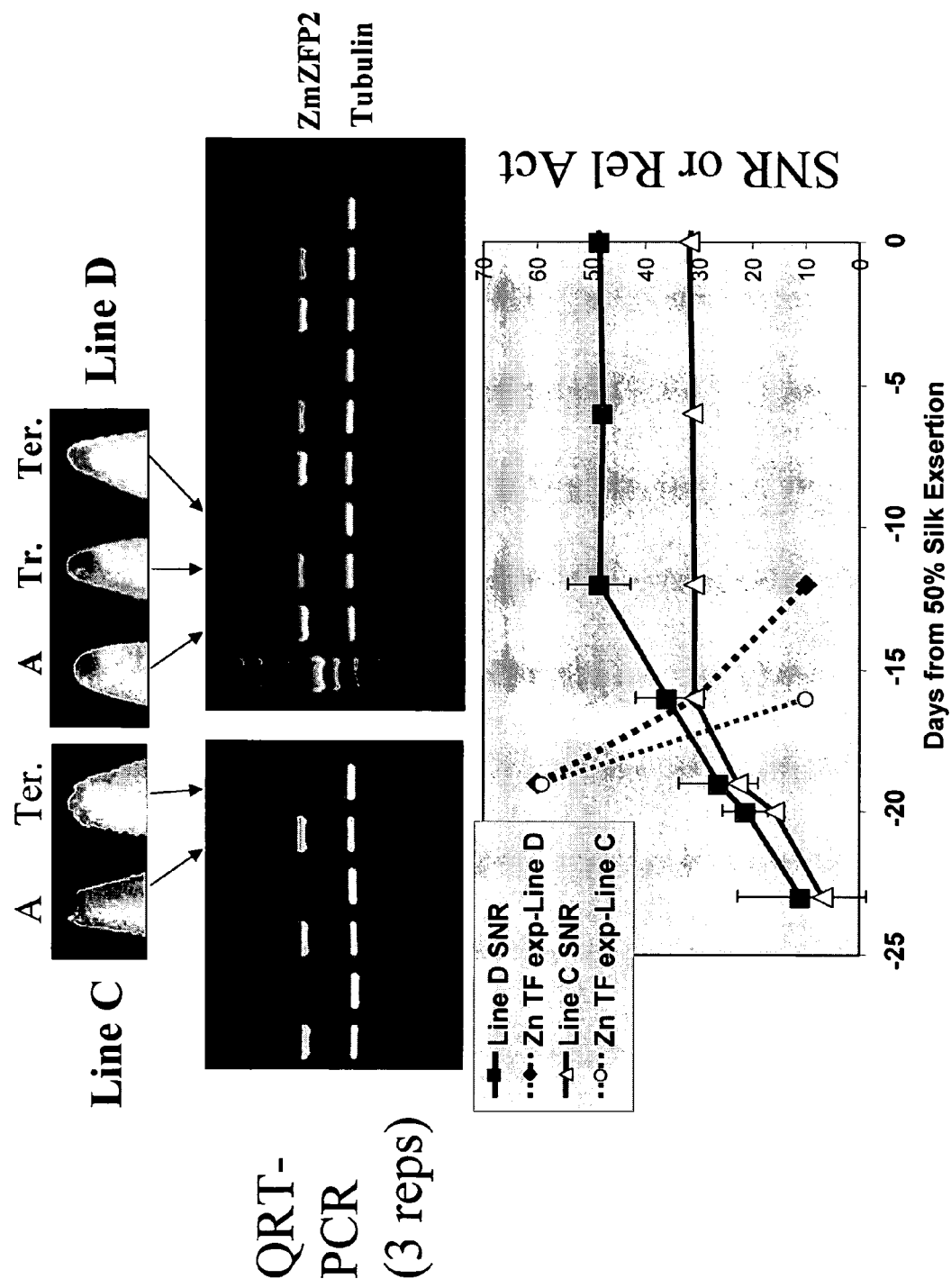
FIG. 2. Data for the quantitative reverse transcription-polymerase chain amplification (QRT-PCR)RNA expression control in immature ear tip tissues for the ZmZFP2-like and maize tubulin genes (as a control for determining the relative amounts of starting RNA from each sample). The ear tip images show the developmental state of the ear inflorescence meristem with an "A" for active, "T" or "Ter" for terminated and "Tr" for transition between active and termination. The middle panels show the QRT-PCR bands for three replicates of both an active and terminated immature ear samples from maize proprietary inbred line Line C and of all three active, transition and terminated immature ear samples of maize proprietary inbred line Line D. Both the ZmZFP2 and the control tubulin bands are shown. The lower panel shows graphically of the spikelet number per row (SNR) development for both Line C and Line D inbred immature ears prior to 50% of the plants showing silk exertion set at 0 days (solid lines) as compared to the relative expression levels of the ZmZFP2 gene for both proprietary inbred lines (dashed lines).

The present invention is based, in part, on the identification of polypeptide haplotypes, referred to herein as *Zea mays* zinc finger protein-2 ("ZmZFP2") polypeptides, that are expressed in plant meristem cells and that contain a core motif characteristic of zinc finger proteins, particularly ZFP2 proteins (see Examples 1 and 2, and FIG. 1; and, the accompanying sequence listing). ZmZFP2 proteins are expressed in meristems, including in maize ear tip meristem while florets are being produced, and are down-regulated as the meristem begins to terminate. As such, the invention provides compositions and methods for manipulating plant development, including, for example, compositions and methods for shortening plant stature for improved agronomic performance and stability under adverse conditions, increasing the number of florets in a plant, thereby increasing its yield, and for generating transgenic plants that are primarily male or are primarily female.

The term "plant" is used broadly herein to include any plant at any stage of development, or to part of a plant, including a plant cutting, a plant cell, a plant cell culture, a plant organ, a plant seed, and a plantlet. The term "meristem" is used herein to refer to the cells in plant tissue that divide by mitosis and are involved in organogenesis. Meristems give rise to various organs, and maintain a central population of undifferentiated cells that replenish the meristem as primordia are formed. In vascular plants, meristems at the apices of roots and shoots are responsible for growth in length and thickness. Shoot apical meristem, for example, forms at the apex of the plant and produces leaf primordia laterally. In conifers and woody dicots, cambium comprises meristem tissue. In flowering plants, axillary meristems arise in the axils of leaf primordia and give rise to inflorescence meristems (IMs), which, in turn, give rise to floral meristems. Inflorescence meristem makes stem tissue, as well as some lateral organs such as inflorescence branches, bracts, and flowers; floral meristem emerges on the flanks of the apical inflorescence meristem and gives rise only to flowers.

The terms "superfemale" and "supermale" are used to herein to refer to a plant which produces only female or male reproductive structures, respectively (which otherwise would produce both all or parts of the male and female structures).

Shoot apical meristem comprises a collection of undifferentiated cells that form during embryogenesis. The production of vegetative structures such as leaves or shoots, and of reproductive structures such as flowers, is temporally segregated, such that a leaf or shoot arises early in a plant life cycle, while a flower develops later. The transition from vegetative to reproductive development is the consequence of floral induction (Yanofsky, *Ann. Rev. Plant Physiol. Plant Mol. Biol.* 46:167-188, 1995). Once induced, shoot apical meristem either persists and produces floral meristem, which gives rise to flowers, and lateral meristem, which gives rise to branches, or is itself converted to floral meristem. Floral meristem differentiates into a single flower having a fixed number of floral organs in a whorled arrangement. Dicotyledonous plants (dicots), for example, contain four whorls, including sepals (first whorl) and petals (second whorl), which surround stamens (third whorl) and carpels (fourth whorl). Although shoot meristem and floral meristem consist of meristemic tissue, shoot meristem is distinguishable from the more specialized floral meristem. Shoot meristem generally is indeterminate and gives rise to an unspecified number of floral and lateral meristems, whereas floral meristem is determinate and gives rise to the fixed number of floral organs that comprise a flower.

As disclosed herein, polynucleotides encoding zinc finger proteins that are expressed in a tissue and stage specific manner in maize meristem have been identified. The zinc finger protein haplotypes are expressed in maize ear tip meristem while the meristem is producing florets, and expression is down-regulated when the meristem begins to terminate. Analysis of mRNA encoding the zinc finger proteins in whole maize plants revealed low levels of expression in roots, stems, and shoot apical/tassel meristems, and in developing kernels, thus demonstrating that the proteins are expressed in essentially all meristems (see Examples 3 to 5). Based on the presence of a domain comprising two conserved cysteine residues and two conserved histidine residues (C2H2 domain) as described for the ZFP2 family of transcription factors (Tague et al., *Plant Mol. Biol.* 28:267, 279, 1995, which is incorporated herein by reference), and its initial identification in *Zea mays* (maize) meristems, the zinc finger proteins of the invention are referred to herein as ZmZFP2 haplotypes.

The term "haplotypes" is used herein in reference to polynucleotides (and the encoded polypeptides) that are variants across inbreds or lines of the same species. As such, the ZmZFP2 haplotypes share substantially high nucleotide and amino acid sequence identity, with differences generally associated with single nucleotide polymorphisms, small insertions or deletions, and the like. For example, the ZmZFP2 polypeptides set forth as SEQ ID NOS: 4, 8, 10 and 14 are identical to each other over their entire 165 amino acid length, and differ from the ZmZFP2 haplotypes set forth as SEQ ID NOS: 6 and 12 in that the latter haplotypes contain an insertion of a glutamine residue after amino acid residue 31 (i.e., between the positions corresponding to residues 31 and 32 of SEQ ID NO: 4, for example), and also contain a substitution of proline for leucine at position 30. Similarly, comparison of the encoding polynucleotides, including the 5' flanking sequences, reveals that the ZmZFP2 haplotypes share between 95.7% and 99.9% identity (compare SEQ ID NOS: 3, 5, 7, 9, 11 and 13; see, also, Example 2).

Accordingly, the invention provides isolated ZmZFP2 polypeptides which have at least 70% sequence identity with the exemplified ZmZFP2 polypeptides (SEQ ID NOS: 2, 4, 6, 8, 10, and 12). For convenience, sequence identity is made with reference to one or two of the exemplified ZmZFP2 polypeptides (or polynucleotides), for example, to SEQ ID NO: 4 and/or SEQ ID NO: 6. However, as disclosed herein, the exemplified ZmZFP2 haplotypes (e.g., SEQ ID NOS: 4 and 6) differ only with respect to one amino acid substitution and one amino acid insertion (or deletion, depending on which sequence is the "reference" sequence). As such, it will be recognized that a polypeptide can be identified as a ZmZFP2 haplotype by detecting at least 70% identity with any of SEQ ID NOS: 2, 4, 6, 8, 10, 12, or 14. It should further be recognized that the at least 70% sequence identity is with respect to the entire ZmZFP2 sequence (e.g., the entire 165 amino acids of the ZmZFP2 polypeptide set forth as SEQ ID NO: 2). As such, where spaces are inserted when aligning a putative ZmZFP2 polypeptide with a "reference" polypeptide (e.g., SEQ ID NO: 4) to maintain maximum sequence homology, such spaces are considered as "differences".

The term "isolated" is used herein to refer to a molecule is in a form other than it exists in nature. An isolated molecule (e.g., a polypeptide or polynucleotide) can comprise, for example, at least about 1% of a sample containing the molecule (e.g., 1%, 2%, 5%, 10%, 25%, or more), or can comprise 50% or more of a sample containing the isolated molecule, or 75% or more of a sample, or 90% or more (e.g., 95%, 99%, 100%). An isolated peptide can be obtained, for example, using cell fractionation methods, an immunoaffinity based method, or chemical synthesis, and can be identified, for example, as an enriched or major (or single) band (or spot) on a gel following one dimensional (or 2D) gel electrophoresis. An isolated polynucleotide can be obtained, for example, by a cloning method. As such, it should be recognized that a cloned polynucleotide is considered "isolated" even though it may be contained in a vector, which can be contained in a host cell, because the cloned polynucleotide is in a form other than the form in which it exists in nature.

The term "polypeptide" or "peptide" is used broadly herein to refer to a polymer of two or more amino acids linked by a covalent bond. The term "peptide portion" is used herein to refer to a smaller part of a full-length polypeptide, including at least two amino acid residues linked by a covalent bond. Generally, a ZmZFP2 peptide portion of the invention contains at least eight contiguous amino acids (i.e., is at least an octapeptide) of a ZmZFP2 polypeptide as set forth in any of SEQ ID NOS: 2, 4, 6, 8, 10, 12, and 14, and can contain, for example, 10, 12, 14, 16, 18 or 20 contiguous amino acids or more (e.g., 20, 25, 30, etc.). However, since ZmZFP2 haplotypes contain a conserved C2H2 domain (see below), it should be recognized that a ZmZFP2 peptide portion of the invention does not consist only of an isolated core motif of a C2H2 domain, or peptide portion of the core motif. Such a core motif of a C2H2 domain is exemplified by amino acid residues 57 to 73 of SEQ ID NO: 4 and by amino acid residues 58 to 74 of SEQ ID NO: 6.

ZmZFP2 haplotypes contain the highly conserved C2H2 motif that is characteristic of zinc finger domain containing proteins and well known in the art (see, e.g., FIG. 1). A zinc finger domain generally includes about 25 to 30 amino acid residues, including a core motif containing 2 conserved cysteine (Cys; C) residues and 2 conserved histidine (H is; H) residues (C-X2-C-X12-H-X3-H (SEQ ID NO: 27), where is cysteine, H is histidine, X is any amino acid, and the number indicates the number of residues; e.g., X2 is X-X). The X12 sequence generally contains polar and basic residues, and is implicated in nucleic acid binding. A zinc finger motif can bind 1 atom of Zn in a tetrahedral array to yield a finger like projection, which interacts with nucleotides in the major groove of the nucleic acid; the zinc atom binds to the conserved Cys and H is residues.

The C2H2 zinc finger is a classical zinc finger domain; the two conserved Cys and H is residues co-ordinate the zinc ion. The C2H2 zinc finger is composed of two short β strands followed by an α-helix. The amino terminal part of the helix binds the major groove in DNA binding zinc fingers (Bilodeau et al., *Plant Physiol.* 17:331, 1998). Several C2H2 zinc finger protein genes have been isolated and characterized in *Arabidopsis thaliana* (Tague and Goodman, *Plant Mol. Biol.* 22:267-279, 1995; Meissner and Michael, *Plant Mol. Biol.* 33:615-624, 1997). The majority of these proteins have one or two fingers, and one, ZATI (AtZFP3.1), has three fingers (Meissner and Michael, supra, 1997). As such, subject to the requirements of a ZmZFP2 peptide as set forth above, it will be recognized that a peptide portion of a ZmZFP2 polypeptide encompassed within the invention includes peptides that are unique to the exemplified ZmZFP2 haplotypes (for example, CTYCRRKFFSSQALG-GHQNAH; SEQ ID NO:28, which comprises the C2H2 core motif of SEQ ID NO:2—conserved Cys and His residues of C2H2 motif in bold), and excludes peptides of other known C2H2 motif containing polypeptides that have the same sequence as a peptide portion of SEQ ID NO:2 (see, e.g., U.S. Pat. No. 6,297,429, which is incorporated herein by reference; see, also, FIG. 1, and the accompanying sequence listing).

Generally, the amino acid residues of a peptide are L-amino acids, and the covalent bond is a peptide bond. However, a peptide also can include one or more D-amino acids, modified amino acids, and/or amino acid analogs, and can include one or more bonds other than a peptide bond. Modified amino acid residues can be obtained commercially, or can be prepared using, for example, a chemical reagent that selectively modifies a functional group (i.e., an amino acid side chain, or an N-terminal or C-terminal reactive group of a peptide) of one or more amino acid residues, or an enzyme that can selectively modify an amino acid residue. Such modifications can be effected on a free amino acid, or can be effected following incorporation of the residue into the peptide, in which case the modifying agent is selected such that it acts under conditions that do not substantially affect the peptide (other than at the particular amino acid residue(s) to be modified). A modifying agent can modify a particular amino acid to generate the desired chemically modified amino acid, or can modify the amino acid such that a second agent or reagent can be contacted with the modified amino acid to generate the desired chemically modified amino acid. For example, a peptide modifying agent can be used to modify a thiol group, an amino group, a carboxyl group, a guanidinium group, a hydroxyl group, or a phenolic group of an amino acid, and can generate the desired unnatural amino acid, which comprises, for example, a carboxylic acid, an acid halide, a carboxylic ester, a thioester, a carbamate, a thiol group, an amino group, or a hydroxy group.

Examples of modifying agents that can react with one or more functional groups of an amino acid, particularly amino acid side chain functional groups, include N-hydroxysuccinimide, which reacts with the primary amine present in exposed lysine residues or an exposed N-terminus of the peptide; maleimide, which reacts with the thio group present in cysteine; iodoacetyl and bromoacetyl groups, which modify cysteine residues; isothiocyanates, which modify primary amines; and hydrazides, which modify aldehyde and ketone groups. Such modified amino acids can be used directly, or can be further contacted, for example, with a moiety that has a reactive group than can react with the modified group on the amino acid, thus generating a modified amino acid comprising the moiety. The moiety can be any molecule as desired, including a biologically active molecule, an affinity tag, a detectable label such as a spectroscopic probe, a selectable marker, or other small organic molecule, peptide, protein, nucleic acid molecule, or the like. Affinity tags include, for example, a polyhistidine sequence, protein A (Nilsson et al., *EMBO J.* 4:1075, 1985; Nilsson et al., *Methods Enzymol.* 198:3, 1991), glutathione S transferase (Smith and Johnson, Gene 67:31, 1988), a Glu-Glu affinity tag (Grussenmeyer et al., *Proc. Natl. Acad. Sci. USA* 82:7952, 1985), substance P, FLAG peptide (Hopp et al., *Biotechnology* 6:1204, 1988), streptavidin binding peptide, biotin, or other antigenic epitope or binding domain (see, also, Ford et al., *Protein Expression and Purification* 2:95 (1991). Examples of spectroscopic probes, include, for example, Alexa Fluor, Marina Blue, Pacific Blue, Alexa Fluor 430, fluorescein-EX, fluorescein isothiocyanate, Oregon Green 488, Oregon Green 514, tetramethylrhodamine Red, Rhodamine Red-X, Texas Red, or other such labels (see, for example, Molecular Probes; Eugene, Oreg.).

The invention also provides ZmZFP2 polypeptide homologs, including orthologs and paralogs, and particularly uses of such homologs (collectively "ZFP2-like" polypeptides) to modulate meristem differentiation in a plant. The term "homolog" is used herein to refer to a polypeptide (or polynucleotide) that has a sequence related to the exemplified ZmZFP2 polypeptides (e.g., SEQ ID NO: 4—or the polynucleotide set forth as SEQ ID NO: 3). Methods for determining that a polypeptide is a ZmZFP2 homolog are disclosed herein (see below) or otherwise known in the art. The term "ortholog" is used herein to refer to a polypeptide (or polynucleotide) that has a sequence related to SEQ ID NO: 4 or SEQ ID NO: 6, and has arisen by speculation from a common ancestor. In general, a ZmZFP2 polypeptide homolog (or ortholog) of the invention has at least about 50% (e.g., 50%, 60%, 70%, 80%) amino acid identity when aligned over the full length of the reference sequence (e.g., SEQ ID NO: 4). It should be recognized that, because the zinc finger-like domain of ZmZFP2 (e.g., SEQ ID NO: 4) contains a core C2H2 motif that is conserved among proteins, the C2H2 motif, alone, cannot be considered in determining whether a polypeptide is a ZmZFP2 ortholog encompassed within the compositions of the invention.

ZmZFP2 polypeptide orthologs and encoding polynucleotides can be identified by comparison with an exemplified sequence (e.g., SEQ ID NO: 4 or SEQ ID NO: 3, respectively) using well known procedures and algorithms based on identity (or homology). Identity (or homology) can be measured using sequence analysis software such as the Sequence Analysis Software Package of the Genetics Computer Group (University of Wisconsin Biotechnology Center, Madison, Wis. 53705). Such software matches similar sequences by assigning degrees of homology to various deletions, substitutions and other modifications. The term "identity" or "homology", when used herein in the context of two or more nucleic acids or polypeptide sequences, refer to two or more sequences or subsequences that, respectively, are the same or have a specified percentage of amino acid residues or of nucleotides that are the same when compared and aligned for maximum correspondence over a comparison window or designated region as measured using any number of sequence comparison algorithms or by manual alignment and visual inspection.

In performing a sequence comparison, one sequence (e.g., SEQ ID NO: 4) acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The term "comparison window" is used broadly herein to include reference to a segment of any one of the number of contiguous positions, for example, about 15 to 600 positions, for example, amino acid or nucleotide position, usually about 20 to about 200 positions, more usually about 50 to about 150 positions, in which a sequence may be compared to a reference sequence of the same number of contiguous positions after the two sequences are optimally aligned. Methods of alignment of sequence for comparison are well-known in the art. Optimal alignment of sequences for comparison can be conducted, for example, by the local homology algorithm of Smith and Waterman (*Adv. Appl. Math.* 2:482, 1981), by the homology alignment algorithm of Needleman and Wunsch (*J. Mol. Biol.* 48:443, 1970), by the search for similarity method of Person and Lipman (*Proc. Natl. Acad. Sci., USA* 85:2444, 1988), each of which is incorporated herein by reference; by computerized implementations of these algorithms (GAP, BESTFIT, FASTA, and TFASTA in the Wisconsin Genetics Software Package, Genetics Computer Group, Madison Wis.); or by manual alignment and visual inspection. Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-induced Multi-sequence Alignment), SAGA (Sequence Alignment by Genetic Algorithm) and WHAT-IF. Such alignment programs can also be used to screen genome databases to identify polynucleotide sequences having substantially identical sequences.

A number of genome databases are available for comparison, including, for example, a substantial portion of the human genome is available as part of the Human Genome Sequencing Project (J. Roach, using hypertext transfer protocol, "http", at URL "weber.u.Washington.edu/~roach/human_genome_progress 2.html"). In addition, numerous genomes have been sequenced in their entirety, including, for example, *E. coli*, yeast (*S. cerevisiae*), *D. melanogaster, C. elegans*, and Arabadopsis. Several databases containing genomic information annotated with some functional information are maintained by different organizations, and are accessible via the internet, for example, using "http", at URL "wwwtigr.org/tdb"; "http", on the world wide web ("www"), at URL "genetics.wisc.edu"; "http", at URL "genome-www.stanford.edu/~ball"; "http", at URL "hiv-web.lanl.gov"; and "http", on the www, at URL "genome.wi.mit.edu".

One example of a useful algorithm is BLAST and BLAST 2.0 algorithms, which are described by Altschul et al. (*Nucleic Acids Res.* 25:3389-3402, 1977; *J. Mol. Biol.* 215:403-410, 1990). Software for performing BLAST analyses is publicly available through the National Center for Biotechnology Information (at "http", on the www, at URL "ncbi.nlm.nih.gov"). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra, 1977, 1990). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=4 and a comparison of both strands. For amino acid sequences, the BLASTP program uses as defaults a wordlength of 3, and expectations (E) of 10, and the BLOSUM62 scoring matrix (see Henikoff and Henikoff, *Proc. Natl. Acad. Sci., USA* 89:10915, 1989) alignments (B) of 50, expectation (E) of 10, M=5, N=4, and a comparison of both strands.

The BLAST algorithm also performs a statistical analysis of the similarity between two sequences (see, for example, Karlin and Altschul, *Proc. Natl. Acad. Sci., USA* 90:5873, 1993, which is incorporated herein by reference). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

In one embodiment, protein and nucleic acid sequence homologies are evaluated using the Basic Local Alignment Search Tool ("BLAST"). In particular, five specific BLAST programs are used to perform the following task:
  (1) BLASTP and BLAST3 compare an amino acid query sequence against a protein sequence database;
  (2) BLASTN compares a nucleotide query sequence against a nucleotide sequence database;
  BLASTX compares the six-frame conceptual translation products of a query nucleotide sequence (both strands) against a protein sequence database;
  (4) TBLASTN compares a query protein sequence against a nucleotide sequence database translated in all six reading frames (both strands); and
  (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (Gonnet et al., *Science* 256:1443-1445, 1992; Henikoff and Henikoff, *Proteins* 17:49-61, 1993, each of which is incorporated herein by reference). Less preferably, the PAM or PAM250 matrices may also be used (Schwartz and Dayhoff, eds., "Matrices for Detecting Distance Relationships: Atlas of Protein Sequence and Structure" (Washington, National Biomedical Research Foundation 1978)). BLAST programs are accessible through the U.S., National Library of Medicine, for example, on the www, at URL "ncbi.nlm.nih.gov". The parameters used with the above algorithms may be adapted depending on the sequence length and degree of homology studied. In some embodiments, the parameters may be the default parameters used by the algorithms in the absence of instructions from the user.

The present invention also provides fusion proteins, which include a ZFP2-like polypeptide, particularly a ZmZFP2 polypeptide or peptide portion thereof operatively linked to a heterologous peptide (or polypeptide). The term "operatively linked" or "operatively associated" is used herein to refer to two or more molecules that, when joined together, generate a chimeric molecule that shares features characteristic of each of the individual molecules. For example, when used in reference to a fusion protein comprising a ZmZFP2 polypeptide and one or more additional polypeptides, the term "operatively linked" means that each polypeptide component of the fusion (chimeric) protein exhibits some or all of a function that is characteristic of the ZmZFP2 polypeptide (or peptide portion thereof) and of the additional polypeptide(s). A fusion protein can be expressed from operatively linked encoding polynucleotides, can be chemically synthesized, or can be joined, either directly or via a spacer molecule, using a chemical reaction.

When used in reference to a transcriptional and/or translational regulatory element (e.g., a promoter) and a second nucleotide sequence, which can encode a gene product such as a ZmZFP2 haplotype, the term "operatively linked" means that the regulatory element is positioned with respect to the second nucleotide sequence such that the regulatory element effects its function with respect to the second nucleotide sequence in substantially the same manner as it does when the regulatory element is present in its natural position in a genome (e.g., a promoter effects transcription of an operatively linked coding sequence). In another example, two operatively linked nucleotide sequences, each of which encodes a polypeptide (e.g., a polynucleotide encoding a peptide portion of ZmZFP2 and a polynucleotide encoding a heterologous peptide) can be operatively linked such that the coding sequences are in frame and, therefore, upon transcription and translation, result in production of two polypeptides, which can be two separate polypeptides or can be a fusion protein comprising the ZmZFP2 peptide portion.

A heterologous peptide that is operatively linked to a ZmZFP2 polypeptide (or peptide portion thereof) can be any peptide (or polypeptide) of interest, including, for example, a peptide tag, which can be useful for detecting and/or isolating a fusion protein comprising the tag. As such, the heterologous peptide can comprise a DNA binding domain of a transcription factor, which is operatively linked to a peptide portion of ZmZFP2 that excludes the C2H2 motif (SEQ ID NO: 27). Such a fusion protein can be useful, for example, for delineating a transcription activation domain of the ZmZFP2 polypeptide.

The present invention further provides an antibody that specifically binds a ZmZFP2 polypeptide, or peptide portion thereof, as well as antigen binding fragments of such antibodies. The term "antibody" is used in its broadest sense to include polyclonal and monoclonal antibodies, as well as antigen binding fragments of such antibodies. An antibody of the invention, or an antigen binding fragment thereof, is characterized, in part, in having specific binding activity for an epitope of a ZmZFP2 polypeptide. The term "binds specifically" or "specific binding activity" or the like, when used in reference to an antibody, means that an interaction of the antibody and a particular epitope has a dissociation constant of at least about $1 \times 10^{-6}$, generally at least about $1 \times 10^{-7}$, usually at least about $1 \times 10^{-8}$, and particularly at least about $1 \times 10^{-9}$ or $1 \times 10^{-10}$ or less. As such, Fab, F(ab')$_2$, Fd and Fv fragments of an antibody that retain specific binding activity for an epitope of a ZmZFP2 haplotype, are included within the definition of an antibody. Antibodies that specifically bind a ZmZFP2 polypeptide or epitopic fragment thereof also is characterized in that it does not substantially crossreact with known zinc finger proteins, some of which are exemplified in FIG. 1 and The accompanying sequence listing. Such crossreacting antibodies can be removed from a polyclonal antibody composition, for example, by passing the polyclonal antibodies over a column having one or more zinc finger proteins (other than a ZmZFP2 haplotype) and/or a peptide comprising a C2H2 domain bound thereto.

The term "antibody", as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (see Huse et al., *Science* 246:1275-1281, 1989, which is incorporated herein by reference). These and other methods of making, for example, chimeric, humanized, CDR-grafted, single chain, and bifunctional antibodies are well known to those skilled in the art (Winter and Harris, *Immunol. Today* 14:243-246, 1993; Ward et al., *Nature* 341:544-546, 1989; Harlow and Lane, *Antibodies: A laboratory manual* (Cold Spring Harbor Laboratory Press, 1988); Hilyard et al., *Protein Engineering: A practical approach* (IRL Press 1992); Borrabeck, *Antibody Engineering*, 2d ed. (Oxford University Press 1995); each of which is incorporated herein by reference).

Antibodies that bind specifically with a ZmZFP2 polypeptide (or peptide portion thereof) can be raised using an exemplified polypeptide (see, e.g., SEQ ID NOS: 2, 4, 6, 8, 10, 12 and 14), or peptide portion of the ZmZFP2 polypeptide as defined herein, as an immunogen and removing antibodies that crossreact, for example, with other zinc finger containing proteins (see Massague, supra, 1998). An antibody of the invention conveniently can be raised using a peptide portion of SEQ ID NO: 4 or SEQ ID NO: 6 that is unique to ZmZFP2 polypeptides (i.e., that is not present in the polypeptides exemplified in The accompanying sequence listing, or encoded by the polynucleotides of The accompanying sequence listing; see, also, FIG. 1). Where such a peptide portion of ZmZFP2 is non-immunogenic, it can be made immunogenic by coupling the hapten to a carrier molecule such as bovine serum albumin (BSA) or keyhole limpet hemocyanin (KLH), or by expressing the hapten as a fusion protein. Carrier molecules and methods for coupling a hapten to a carrier molecule are well known and routine in the art (see, for example, Harlow and Lane, supra, 1988).

Methods for raising polyclonal antibodies, for example, in a rabbit, goat, or mouse, are well known in the art (see, for example, Green et al., "Production of Polyclonal Antisera," in *Immunochemical Protocols* (Manson, ed., Humana Press 1992), pages 1-5; Coligan et al., "Production of Polyclonal Antisera in Rabbits, Rats, Mice and Hamsters," in *Curr. Protocols Immunol* (1992), section 2.4.1; each or which is incorporated herein by reference). Monoclonal antibodies also can be obtained using well known and routine methods (Harlow and Lane, supra, 1988). For example, spleen cells from a mouse immunized with a ZmZFP2 polypeptide, or an epitopic fragment thereof, can be fused to an appropriate myeloma cell line such as SP/02 myeloma cells to produce hybridoma cells. Cloned hybridoma cell lines can be screened using labeled antigen to identify clones that secrete monoclonal antibodies having the appropriate specificity, and hybridomas expressing antibodies having a desirable specificity and affinity can be isolated, thus providing a continuous source of the antibodies (see, e.g., Kohler and Milstein, *Nature* 256:495, 1975; Coligan et al., supra, 1992, see sections 2.5.1-2.6.7; Harlow and Lane, supra, 1988). Such antibodies are useful, for example, for preparing standardized kits for commercial or research use.

Monoclonal antibodies can be isolated and purified from hybridoma cultures by a variety of well established techniques, including, for example, affinity chromatography with Protein-A SEPHAROSE gel, size exclusion chromatography, and ion exchange chromatography (Coligan et al., supra, 1992, see sections 2.7.1-2.7.12 and sections 2.9.1-2.9.3; see, also, Barnes et al., "Purification of Immunoglobulin G (IgG)," in *Meth. Molec. Biol.* 10:79-104 (Humana Press 1992), which is incorporated herein by reference). Methods of in vitro and in vivo multiplication of monoclonal antibodies is well known to those skilled in the art. Multiplication in vitro can be carried out in suitable culture media such as Dulbecco's Modified Eagle Medium or RPMI 1640 medium, optionally replenished by a mammalian serum such as fetal calf serum or trace elements and growth sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo can be carried out by injecting cell clones into mammals histocompatible with the parent cells, for example, syngeneic mice, to cause growth of antibody producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Antibody fragments having ZmZFP2 specific binding activity can be prepared by proteolytic hydrolysis of a ZmZFP2 specific antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see, for example, Goldenberg, U.S. Pat. No. 4,036,945 and U.S. Pat. No. 4,331,647; Nisonhoff et al., *Arch. Biochem. Biophys.* 89:230. 1960; Porter, *Biochem. J.* 73:119, 1959; Edelman et al., Meth. Enzymol., 1:422 (Academic Press 1967); Coligan et al., supra, 1992, see sections 2.8.1-2.8.10 and 2.10.1-2.10.4).

Other methods of cleaving antibodies, such as separation of heavy chains to form monovalent light/heavy chain fragments, further cleavage of fragments, or other enzymatic, chemical, or genetic techniques can also be used, provided the fragments specifically bind to the antigen that is recognized by the intact antibody. For example, Fv fragments comprise an association of $V_H$ and $V_L$ chains. This association can be noncovalent (Inbar et al., *Proc. Natl. Acad. Sci., USA* 69:2659, 1972). Alternatively, the variable chains can be linked by an intermolecular disulfide bond or cross-linked by chemicals such as glutaraldehyde (Sandhu, supra, 1992). Preferably, the Fv fragments comprise $V_H$ and $V_L$ chains connected by a peptide linker. The single-chain antigen binding proteins (sFv) can be prepared by constructing a structural gene comprising DNA sequences encoding the $V_H$ and $V_L$ domains connected by an oligonucleotide (see, for example, by Whitlow et al., *Methods: A Companion to Methods in Enzymology* 2:97, 1991; Bird et al., *Science* 242:423-426, 1988; Ladner et al., U.S. Pat. No. 4,946,778; Pack et al., *BioTechnology* 11:1271-1277, 1993; each of which is incorporated herein by reference). Another form of an antibody fragment is a peptide coding for a single complementarity-determining region (CDR). CDR peptides ("minimal recognition units") can be obtained by constructing nucleic acid molecules encoding the CDR of an antibody of interest. Such nucleic acid molecules can be prepared, for example, using the polymerase chain reaction (PCR) to synthesize the variable region from RNA of antibody-producing cells (see, for example, Larrick et al., *Methods: A Companion to Methods in Enzymology* 2:106, 1991, which is incorporated herein by reference).

The invention also provides isolated nucleic acid molecules encoding a ZmZFP2 polypeptide, or a peptide portion of a ZmZFP2 polypeptide, which can be a peptide portion having DNA binding activity, transcription activating activity, or both, and also provides nucleic acid molecules complementary to such coding sequences. Polynucleotides of the invention are exemplified by SEQ ID NOS: 1, 3, 5, 7, 9, 11, and 13 (and their complements), and by polynucleotides that encode SEQ ID NOS: 2, 4, 6, 8, 10, 12, and 14 (and their complements). Also provided are isolated nucleic acid molecules encoding homologs, including orthologs and/or paralogs, of a ZmZFP2 polypeptide having an amino acid sequence that is at least 50% identical to an amino acid sequence as set forth in SEQ ID NO: 4 or SEQ ID NO: 6, for example, an ortholog obtained from rice, soybean, wheat, barley, or the like, provided that, except for the ZmZFP2 polynucleotides and polypeptides, the polynucleotide is not a polynucleotide as shown in The accompanying sequence listing and does not encode a polypeptide as shown in The accompanying sequence listing and FIG. 1.

As used herein, the term "nucleic acid molecule" or "polynucleotide" or "nucleotide sequence" refers broadly to a sequence of two or more deoxyribonucleotides or ribonucleotides that are linked together by a phosphodiester bond. As such, the terms include RNA and DNA, which can be a gene or a portion thereof, a cDNA, a synthetic polydeoxyribonucleic acid sequence, or the like, and can be single stranded or double stranded, as well as a DNA/RNA hybrid. The terms are used herein to include naturally occurring nucleic acid molecules, which can be isolated from a cell, as well as synthetic molecules, which can be prepared, for example, by methods of chemical synthesis or by enzymatic methods such as by PCR. The term "recombinant" is used herein to refer to a nucleic acid molecule that is manipulated outside of a cell, including, for example, two or more linked heterologous nucleotide sequences. The term "heterologous" is used herein to refer to nucleotide sequences that are not normally linked in nature or, if linked, are linked in a different manner than that disclosed herein. For example, reference to a transgene comprising a coding sequence operatively linked to a heterologous promoter means that the promoter is one that does not normally direct expression of the nucleotide sequence in a specified cell in nature.

In general, the nucleotides comprising a nucleic acid molecule (e.g., a transgene) are naturally occurring deoxyribonucleotides, such as adenine, cytosine, guanine or thymine linked to 2'-deoxyribose, or ribonucleotides such as adenine, cytosine, guanine or uracil linked to ribose. However, a nucleic acid molecule or nucleotide sequence also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22:5220-5234, 1994; Jellinek et al., *Biochemistry* 34:11363-11372, 1995; Pagratis et al., *Nature Biotechnol.* 15:68-73, 1997, each of which is incorporated herein by reference). Similarly, the covalent bond linking the nucleotides of a nucleotide sequence generally is a phosphodiester bond, but also can be, for example, a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22:977-986, 1994; Ecker and Crooke, *BioTechnology* 13:351360, 1995, each of which is incorporated herein by reference). The incorporation of non-naturally occurring nucleotide analogs or bonds linking the nucleotides or analogs can be particularly useful where the nucleic acid molecule is to be exposed to an environment that can contain a nucleolytic activity, including, for example, a plant tissue culture medium or in a plant cell, since the modified molecules can be less susceptible to degradation.

A nucleotide sequence containing naturally occurring nucleotides and phosphodiester bonds, can be chemically synthesized or can be produced using recombinant DNA methods, using an appropriate polynucleotide as a template. In comparison, a nucleotide sequence containing nucleotide analogs or covalent bonds other than phosphodiester bonds generally are chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995).

A nucleic acid molecule of the invention can be single stranded or double stranded, and can be DNA or RNA or a hybrid thereof. As such, the nucleic acid molecules of the invention include, for example, a nucleotide sequence that, when expressed, can encode a ZmZFP2 polypeptide, or can comprise the sequence complementary to the coding strand (e.g., an antisense molecule). The nucleic acid molecules of the invention also can contain two or more nucleotide sequences comprising all or a portion of a nucleic acid molecule encoding a ZmZFP2 polypeptide, for example, a portion of the coding sequence and, in reverse orientation, the corresponding complementary sequence, such that the unit comprises an inverted repeat. Where such a nucleic acid molecule comprises a single stranded RNA molecule, or where the nucleic acid molecule is a DNA molecule from which a single stranded RNA molecule is transcribed, the RNA molecule can self hybridize to form a hairpin structure, which, for example, can mediate RNA interference (RNAi) or can act as a co-suppressor RNA.

A polynucleotide encoding ZmZFP2 (or a peptide portion thereof) can be operatively linked to one or more heterologous nucleotide sequences of interest. The heterologous nucleotide sequence(s) can be, for example, one or a plurality of regulatory elements, which can be translational regulatory elements (e.g., a ribosome recognition/binding sequence and/or an internal ribosome entry site) and/or transcriptional regulatory elements (e.g., a promoter, an enhancer, and/or a terminator). Where a heterologous nucleotide sequence is a promoter, it can be a constitutive promoter, an inducible promoter, a tissue specific promoter, or a developmental stage specific promoter, including, for example, an environmentally regulated promoter, an organelle specific promoter, a cell specific promoter, a promoter active only in male plant reproductive tissues or in female plant reproductive tissues (e.g., an anther specific promoter, pollen specific promoter, or ovary specific promoter), or a meristem specific promoter (e.g., an apical meristem specific promoter, an inflorescence meristem specific promoter, and/or a floral meristem specific promoter).

A heterologous nucleotide sequence operatively linked to a nucleic acid molecule of the invention also can encode a second (or more) polypeptide(s), in addition to the encoded ZmZFP2 polypeptide (or homolog) or peptide portion thereof. Such heterologous nucleotide sequences can be operatively linked such that the encoded polypeptides, including the ZmZFP2 polypeptide, can be co-expressed as a fusion protein or as separate polypeptides, as desired. Such an operatively linked heterologous nucleotide sequence can encode, for example, a cell localization domain (e.g., a signal peptide, or a nuclear localization domain), a peptide tag (e.g., a c-myc epitope) or other detectable polypeptide (e.g., a fluorescent protein such as a green fluorescent protein, or an enzyme such as luciferase), or a polypeptide that confers a selective advantage (or disadvantage) upon a cell containing the polypeptide (e.g., phosphinothricin acetyltransferase, which confers resistance to phosphinothricin).

Where the nucleic acid molecule comprises an inverted repeat of all or a portion of a nucleic acid molecule encoding ZmZFP2, a heterologous nucleotide sequence operatively linked to the nucleic acid molecule can comprise a spacer nucleotide sequence, which, for example, provides sufficient spacing between the repeat units such that self-hybridization of a single stranded form of the nucleic acid molecule (e.g., RNA) is not constrained. With respect to an RNA molecule of the invention, a heterologous nucleotide sequence also can be a nucleotide sequence that confers ribozyme activity. An antisense polynucleotide, ribozyme or triplexing agent is complementary to a target sequence, which can be a DNA or RNA sequence, for example, mRNA, and can be a coding sequence, a nucleotide sequence comprising an intron-exon junction, a regulatory sequence such as a Shine-Delgarno sequence, or the like. The degree of complementarity is such that the polynucleotide, for example, an antisense polynucleotide, can interact specifically with the target sequence in a cell. Depending on the total length of the antisense or other polynucleotide, one or a few mismatches with respect to the target sequence can be tolerated without losing the specificity of the polynucleotide for its target sequence. Thus, few if any mismatches would be tolerated in an antisense molecule consisting, for example, of 20 nucleotides, whereas several mismatches will not affect the hybridization efficiency of an antisense molecule that is complementary, for example, to the full length of a target mRNA encoding a cellular polypeptide. The number of mismatches that can be tolerated can be estimated, for example, using well known formulas for determining hybridization kinetics (see Sambrook et al., "Molecular Cloning: A laboratory manual" (Cold Spring Harbor Laboratory Press 1989)) or can be determined empirically using methods known in the art, including, for example, by determining that the presence of the antisense polynucleotide, ribozyme, or triplexing agent in a cell decreases the level of the target ZmZFP2 sequence (or expression of the encoded polypeptide) in a cell.

A polynucleotide useful as an antisense molecule, a ribozyme or a triplexing agent can inhibit translation of or cleave a target nucleic acid molecule. An antisense molecule, for example, can bind to a ZmZFP2 mRNA to form a double stranded molecule that cannot be translated in a cell. Antisense oligonucleotides of at least about 15 to 25 nucleotides are preferred since they are easily synthesized and can hybridize specifically with a target sequence, although longer antisense molecules can be expressed from a polynucleotide introduced into the target cell. Specific nucleotide sequences useful as antisense molecules can be identified using well known methods, for example, gene walking methods (see, for example, Seimiya et al., *J. Biol. Chem.* 272:4631-4636, 1997, which is incorporated herein by reference). Where the antisense molecule is contacted directly with a target cell, it can be operatively associated with a chemically reactive group such as iron-linked EDTA, which cleaves a target RNA at the site of hybridization. A triplexing agent, in comparison, can stall transcription (Maher et al., *Antisense Res. Devel.* 1:227, 1991; Helene, *Anticancer Drug Design* 6:569, 1991).

A heterologous nucleotide sequence operatively linked to a polynucleotide encoding ZmZFP2, or a nucleotide sequence complementary thereto, also can be a transcriptional and/or translational regulatory element such that the ZmZFP2 polynucleotide is an expressible polynucleotide. As used herein, the term "expressible" refers to a polynucleotide that can be expressed, but that may not necessarily be expressed at a particular point in time. For example, where a promoter of an expressible transgene in a cell is an inducible promoter lacking basal activity, an operatively linked expressible polynucleotide is expressed only upon exposure to an appropriate inducing agent.

Transcriptional promoters generally act in a position and orientation dependent manner, and usually are positioned at or within about five nucleotides to about fifty nucleotides 5' (upstream) of the start site of transcription of a gene in nature. In comparison, enhancers can act in a relatively position or orientation independent manner, and can be positioned several hundred or thousand nucleotides upstream or downstream from a transcription start site, or in an intron within the coding region of a gene, yet still be operatively linked to the coding region so as to enhance transcription. The relative positions and orientations of various regulatory elements in addition to a promoter, including the positioning of a transcribed regulatory sequence such as an internal ribosome entry site, or a translated regulatory element such as a cell compartmentalization domain in an appropriate reading frame, are well known and methods for operatively linking such elements are routine in the art (see, for example, Sambrook et al., supra, 1989; Ausubel et al., "Current Protocols in Molecular Biology" (John Wiley and Sons, Baltimore Md. 1987, and supplements)).

Promoters useful for expressing a nucleic acid molecule of interest can be any of a range of naturally-occurring promoters known to be operative in plants and/or animals, as desired. Promoters that direct expression in meristem cells or in cells derived from meristem cells can be useful for expressing ZmZFP2 ectopically. As used herein, the term "ectopically expressed" or "ectopic expression" or the like refers to a ZmZFP2 polynucleotide that is or can be expressed in a tissue other than a tissue in which it normally is expressed (i.e., meristem) or at a time other than the time at which it normally is expressed. Ectopic expression of ZmZFP2 can be effected by directing expression of a ZmZFP2 coding sequence from a heterologous promoter.

Promoters useful for purposes of the present invention include, for example, constitutive promoters, which generally are active in most or all tissues of a plant; inducible promoters, which generally are inactive or exhibit a low basal level of expression, and can be induced to a relatively higher activity upon contact of cells with an appropriate inducing agent; tissue specific promoters and tissue preferred promoters, which generally are expressed in only one or a few particular cell types (e.g., plant anther cells); and developmental or stage specific promoters, which are active only during a defined period during the growth and/or development of a plant. Exemplary promoters include the constitutive 35S cauliflower mosaic virus (CaMV) promoter, the ripening-enhanced tomato polygalacturonase promoter, the E8 promoter, and the fruit specific 2A1 promoter, U2 and U5 snRNA promoters from maize, the promoter of the alcohol dehydrogenase gene, the Z4 promoter from a gene encoding the Z4 22 kD zein protein, the Z10 promoter from a gene encoding a 10 kD zein protein, a Z27 promoter from a gene encoding a 27 kD zein protein, the A20 promoter from the gene encoding a 19 kD zein protein, the light inducible promoter derived from the pea rbcS gene, the TB1 promoter, which directs expression, for example, in maize axillary meristems and in stamens of ear primordia, the CVL3 promoter, the meristem-specific Mzec promoter, and the actin promoter from rice (U.S. Pat. No. 5,641,876; WO 00/70067).

Tissue specific or stage specific regulatory elements further include, for example, the AGL8/FRUITFULL regulatory element, which is activated upon floral induction (Hempel et al., *Development* 124:3845-3853, 1997, which is incorporated herein by reference); root specific regulatory elements such as the regulatory elements from the RCP1 gene and the LRP1 gene (Tsugeki and Fedoroff, *Proc. Natl. Acad., USA* 96:12941-12946, 1999; Smith and Fedoroff, *Plant Cell* 7:735-745, 1995, each of which is incorporated herein by reference); flower specific regulatory elements such as the regulatory elements from the LEAFY gene and the APETELA1 gene (Blazquez et al., *Development* 124:3835-3844, 1997, which is incorporated herein by reference; Hempel et al., supra, 1997); seed specific regulatory elements such as the regulatory element from the oleosin gene (Plant et al., *Plant Mol. Biol.* 25:193-205, 1994, which is incorporated herein by reference), and dehiscence zone specific regulatory elements. Additional tissue specific or stage specific regulatory elements include the Znl3 promoter, which is a pollen specific promoter (Hamilton et al., *Plant Mol. Biol.* 18:211-218, 1992, which is incorporated herein by reference); the UNUSUAL FLORAL ORGANS (UFO) promoter, which is active in apical shoot meristem; the promoter active in shoot meristems (Atanassova et al., *Plant J.* 2:291, 1992, which is incorporated herein by reference), the cdc2a promoter and cyc07 promoter (see, for example, Ito et al., *Plant Mol. Biol.* 24:863, 1994; Martinez et al., *Proc. Natl. Acad. Sci., USA* 89:7360, 1992; Medford et al., *Plant Cell* 3:359, 1991; Terada et al., *PlantJ.* 3:241, 1993; Wissenbach et al., *Plant J.* 4:411, 1993, each of which is incorporated herein by reference); the promoter of the APETELA3 gene, which is active in floral meristems (Jack et al., *Cell* 76:703, 1994, which is incorporated herein by reference; Hempel et al., supra, 1997); a promoter of an agamous-like (AGL) family member, for example, AGL8, which is active in shoot meristem upon the transition to flowering (Hempel et al., supra, 1997); floral abscission zone promoters; Li-specific promoters; and the like. Additional tissue-specific promoters can be isolated using well known methods (see, e.g., U.S. Pat. No. 5,589,379).

Inducible promoters demonstrate increased transcriptional activity upon contact with an inducing agent. Inducing agents can be chemical, biological or physical agents or environmental conditions that effects transcription from an inducible regulatory element. In response to exposure to an inducing agent, transcription from the inducible regulatory element generally is initiated de novo or is increased above a basal or constitutive level of expression. An inducing agent useful for inducing expression from an inducible promoter is selected based on the particular inducible regulatory element. Examples of inducible regulatory elements include a metallothionein regulatory element, a copper inducible regulatory element, or a tetracycline inducible regulatory element, the transcription from which can be effected in response to divalent metal ions, copper or tetracycline, respectively (Furst et al., *Cell* 55:705-717, 1988; Melt et al., *Proc. Natl. Acad. Sci., USA* 90:45674571,1993; Gatz et al., *Plant J.* 2:397404, 1992; Roder et al., *Mol. Gen. Genet.* 243:32-38, 1994, each of which is incorporated herein by reference). Inducible regulatory elements also include an ecdysone regulatory element or a glucocorticoid regulatory element, the transcription from which can be effected in response to ecdysone or other steroid (Christopherson et al., *Proc. Natl. Acad. Sci., USA* 89:6314-6318, 1992; Schena et al., *Proc. Natl. Acad. Sci., USA* 88:10421-10425, 1991, each of which is incorporated herein by reference); or a cold responsive regulatory element or a heat shock regulatory element, the transcription of which can be effected in response to exposure to cold or heat, respectively (Takahashi et al., *Plant Physiol.* 99:383-390, 1992, which is incorporated herein by reference).

Additional regulatory elements useful in the methods or compositions of the invention include, for example, the spinach nitrite reductase gene regulatory element (Back et al., *Plant Mol. Biol.* 17:9, 1991, which is incorporated herein by reference); a light inducible regulatory element (Feinbaum et al., *Mol. Gen. Genet.* 226:449, 1991; Lam and Chua, *Science* 248:471, 1990, each of which is incorporated herein by reference), a plant hormone inducible regulatory element (Yamaguchi-Shinozaki et al., *Plant Mol. Biol.* 15:905, 1990; Kares et al., *Plant Mol. Biol.* 15:225, 1990, each of which is incorporated herein by reference), and the like. An inducible regulatory element also can be a plant stress-regulated regulatory element, the copper responsive promoter from the ACEI system (Mett et al., *Proc. Natl. Acad. Sci., USA* 90:4567-4571, 1993, which is incorporated herein by reference); the promoter of the maize In2 gene, which responds to benzenesulfonamide herbicide safeners (Hershey et al., *Mol. Gen. Gene.* 227:229-237, 1991; Gatz et al., *Mol. Gen. Genet.* 243:32-38, 1994, each of which is incorporated herein by reference), and the Tet repressor of transposon Tn10 (Gatz et al., *Mol. Gen. Genet.* 227:229-237, 1991, which is incorporated herein by reference). Other promoters active in plant cells include a gamma zein promoter, an oleosin ole16 promoter, a globulin I promoter, an actin I promoter, an actin cl promoter, a sucrose synthetase promoter, an INOPS promoter, an EXM5 promoter, a globulin2 promoter, a b-32, ADPG-pyrophosphorylase promoter, an Ltp1 promoter, an Ltp2 promoter, an oleosin ole17 promoter, an oleosin ole18 promoter, an actin 2 promoter, a pollen-specific protein promoter, a pollen-specific pectate lyase promoter, an anther specific gene RTS2 promoter, a pollen-specific gene promoter, a tapetum specific gene RAB24 promoter, a anthranilate synthase alpha subunit promoter, an alpha zein promoter, an anthranilate synthase beta subunit promoter, a dihydrodipicolinate synthase promoter, a Thi I promoter, an alcohol dehydrogenase promoter, a cab binding protein promoter, an H3C4 promoter, a RUBISCO SS starch branching enzyme promoter, an actin3 promoter, an actin7 promoter, a regulatory protein GF14-12 promoter, a ribosomal protein L9 promoter, a cellulose biosynthetic enzyme promoter, an S-adenosyl-L-homocysteine hydrolase promoter, a superoxide dismutase promoter, a C-kinase receptor promoter, a phosphoglycerate mutase promoter, a root-specific RCc3 mRNA promoter, a glucose-6 phosphate isomerase promoter, a pyrophosphate-fructose 6-phosphate-I-phosphotransferase promoter, an ubiquitin promoter, a beta-ketoacyl-ACP synthase promoter, a 33 kDa photosystem 11 promoter, an oxygen evolving protein promoter, a 69 kDa vacuolar ATPase subunit promoter, a glyceraldehyde-3-phosphate dehydrogenase promoter, an ABA- and ripening-inducible-like protein promoter, a phenylalanine ammonia lyase promoter, an adenosine triphosphatase S-adenosyl-L-homocysteine hydrolase promoter, a chalcone synthase promoter, a zein promoter, a globulin-1 promoter, an auxin-binding protein promoter, a UDP glucose flavonoid glycosyl-transferase gene promoter, an NTI promoter, an actin promoter, and an opaque 2 promoter.

A tissue-specific promoter that is active in cells of male or female reproductive organs can be particularly useful for ectopically expressing a ZnC2H2 polypeptide. Exemplary stamen specific promoters include, but are not limited to, anther-specific promoters such as the LAT52 gene promoter (Twell et al., *Mol. Gen. Genet.* 217:240-245, 1989, which is incorporated herein by reference); pollen specific promoters such as the Zm13 gene promoter (Guerrero et al., *Mol. Gen. Genet.* 224:161-168, 1993, which is incorporated herein by reference), microspore specific promoters such as the apg gene promoter (Twell et al., *Sex. Plant Reprod.* 6: 217-224 (1993, which is incorporated herein by reference), and tapetum specific promoters such as the TA29 gene promoter (Mariani et al., *Nature* 347:737, 1990; U.S. Pat. No. 6,372,967, each of which is incorporated herein by reference), and other stamen specific promoters such as the MS45 gene promoter, 5126 gene promoter, BS7 gene promoter, or SB200 gene promoter.

A heterologous nucleotide sequence operatively linked to a polynucleotide encoding a ZmZFP2 polypeptide, or a polynucleotide complementary thereto, also can comprise a vector, which can be a cloning vector, targeting vector, expression vector, or the like. An expression vector, or nucleotide sequences of an expression vector, can be a plant expression vector, for example, a vector based on an *Agrobacterium* Ti plasmid or Ri plasmid. A vector can be useful for introducing an exogenous nucleic acid molecule into a cell. The term "exogenous" is used herein to refer to any material that is introduced into a cell. The term "exogenous nucleic acid molecule" or "transgene" refers to any nucleic acid molecule that either is not normally present in a cell genome or is introduced into a cell. Such exogenous nucleic acid molecules generally are recombinant nucleic acid molecules, which are generated using recombinant DNA methods as disclosed herein or otherwise known in the art. A ZmZFP2 haplotype (e.g., a LINE A ZmZFP2 haplotype), for example, can be considered an exogenous nucleic acid molecule when introduced into a different maize line (e.g., Line B). The term "endogenous", when used in reference to a gene, means a gene that is normally present in the genome of cells of a specified organism, and is present in its normal state in the cells (i.e., present in the genome in the state in which it normally is present in nature).

An exogenous nucleic acid molecule can be introduced into a cell as a naked DNA molecule, can be incorporated in a matrix such as a liposome or a particle such as a viral particle, or can be incorporated into a vector. Incorporation of the polynucleotide into a vector can facilitate manipulation of the polynucleotide, or introduction of the polynucleotide into a plant cell. Accordingly, the vector can be derived from a plasmid or can be a viral vector such as a T-DNA vector (Horsch et al., *Science* 227:1229-1231 (1985), which is incorporated herein by reference). If desired, the vector can include components of a plant transposable element, for example, a Ds transposon (Bancroft and Dean, *Genetics* 134:1221-1229, 1993, which is incorporated herein by reference) or an Spm transposon (Aarts et al., *Mol. Gen. Genet.* 247:555-564, 1995, which is incorporated herein by reference).

In addition to containing a transgene of interest, a vector also can contain various nucleotide sequences that facilitate, for example, rescue of the vector from a transformed plant cell; passage of the vector in a host cell, which can be a plant, animal, bacterial, or insect host cell; or expression of an encoding nucleotide sequence in the vector, including all or a portion of a rescued coding region. As such, a vector can contain any of a number of additional transcription and translation regulatory elements, including constitutive and inducible promoters, enhancers, terminators, and the like (see, for example, Bitter et al., *Meth. Enzymol.* 153:516-544, 1987). For example, a vector can contain elements useful for passage, growth or expression in a bacterial system, including a bacterial origin of replication; a promoter, which can be an inducible promoter; and the like. A vector also can contain one or more restriction endonuclease recognition and cleavage sites, including, for example, a polylinker sequence, to facilitate insertion or removal of a transgene.

Further, a polynucleotide encoding a ZmZFP2 polypeptide, or peptide portion thereof, can be operatively linked to a heterologous polynucleotide encoding a polypeptide of interest (or the "heterologous polynucleotide" can be a component of a vector containing the ZmZFP2 polynucleotide). For example, the heterologous polynucleotide can encode an enzyme such as β-galactosidase, β-glucuronidase, green fluorescent protein, coral red fluorescent protein and their derivatives, glucocorticoid or steroid receptor and the like to create an inducible fusion protein form to induce the ZFP2 function, also luciferase, alkaline phosphatase, glutathione S-transferase, chloramphenicol acetyltransferase, guanine xanthine phosphoribosyltransferase, and neomycin phosphotransferase; a viral polypeptide or a peptide portion thereof; or a plant growth factor or hormone. Expression of such a heterologous nucleotide sequence can provide a means for selecting for a cell containing the construct, for example, by conferring a desirable phenotype to a plant cell containing the nucleotide sequence. For example, the heterologous nucleotide sequence can be, or encode, a selectable marker, which, when present or expressed in a plant cell, provides a means to identify the plant cell containing the marker.

A selectable marker provides a means for screening a population of organism or cells of an organism (e.g., plants or plant cells) to identify those having the marker and, therefore, the transgene of interest. A selectable marker generally confers a selective advantage to the cell, or an organism (e.g., a plant) containing the cell, for example, the ability to grow in the presence of a negative selective agent such as an antibiotic or, for a plant, an herbicide. A selective advantage also can be due, for example, to an enhanced or novel capacity to utilize an added compound as a nutrient, growth factor or energy source. A selective advantage can be conferred by a single polynucleotide, or its expression product, or by a combination of polynucleotides whose expression in a plant cell gives the cell a positive selective advantage, a negative selective advantage, or both. It should be recognized that expression of the transgene of interest also provides a means to select cells containing the encoding nucleotide sequence. However, the use of an additional selectable marker, which, for example, allows a plant cell to survive under otherwise toxic-conditions, provides a means to enrich for transformed plant cells containing the desired transgene.

Examples of selectable markers include those described above, as well as those that confer antimetabolite resistance, for example, dihydrofolate reductase, which confers resistance to methotrexate (Reiss, *Plant Physiol.* (Life Sci. Adv.) 13:143-149, 1994); neomycin phosphotransferase, which confers resistance to the aminoglycosides neomycin, kanamycin and paromycin (Herrera-Estrella, *EMBO J.* 2:987-995, 1983) and hygro, which confers resistance to hygromycin (Marsh, *Gene* 32:481-485, 1984), trpB, which allows cells to utilize indole in place of tryptophan; hisD, which allows cells to utilize histinol in place of histidine (Hartman, *Proc. Natl. Acad. Sci., USA* 85:8047, 1988); mannose-6-phosphate isomerase which allows cells to utilize mannose (WO 94/20627); ornithine decarboxylase, which confers resistance to the ornithine decarboxylase inhibitor, 2-(difluoromethyl)-DL-ornithine (DFMO; McConlogue, 1987, In: "Current Communications in Molecular Biology", Cold Spring Harbor Laboratory Press); and deaminase from *Aspergillus terreus*, which confers resistance to Blasticidin S (Tamura, *Biosci. Biotechnol. Biochem.* 59:2336-2338, 1995).

Additional selectable markers include those that confer herbicide resistance, for example, phosphinothricin acetyltransferase gene, which confers resistance to phosphinothricin (White et al., *Nucl. Acids Res.* 18:1062, 1990; Spencer et al., *Theor. Appl. Genet.* 79:625-631, 1990), a mutant EPSPV-synthase, which confers glyphosate resistance (Hinchee et al., *BioTechnology* 91:915-922, 1998), a mutant acetolactate synthase, which confers imidazolione or sulfonylurea resistance (Lee et al., *EMBO J.* 7:1241-1248, 1988), a mutant psbA, which confers resistance to atrazine (Smeda et al., *Plant Physiol.* 103:911-917, 1993), or a mutant protoporphyrinogen oxidase (see U.S. Pat. No. 5,767,373), or other markers conferring resistance to an herbicide such as glufosinate. In addition, markers that facilitate identification of a plant cell containing the polynucleotide encoding the marker include, for example, luciferase (Giacomin, *Plant Sci.* 116:59-72, 1996; Scikantha, *J. Bacterol.* 178:121, 1996), green fluorescent protein (Gerdes, *FEBS Lett.* 389:

44-47, 1996) or fl-glucuronidase (Jefferson, *EMBO J.* 6:3901-3907, 1997), and numerous others as disclosed herein or otherwise known in the art. Such markers also can be used as reporter molecules.

The invention also provides a host cell containing a nucleic acid molecule encoding a ZmZFP2 polypeptide, or peptide portion thereof (and/or complement thereof, e.g., a double stranded DNA), wherein the nucleic acid molecule can, but need not, be contained in a vector. The host cell can be a prokaryotic cell or eukaryotic cell, and can be a bacterial cell, an insect cell, an animal cell, or a plant cell. A host cell can provide a means for maintaining or expanding the nucleic acid molecule of the invention, or for expressing an encoded product of the nucleic acid molecule (e.g., ZmZFP2 polypeptide), including for obtaining desired amounts of the RNA or protein or for characterizing the function of the RNA or protein in the host cell.

In one embodiment, the host cell containing an exogenous ZmZFP2 polynucleotide is a plant cell. A plant cell is the structural and physiological unit of the plant, comprising a protoplast and a cell wall. The plant cell can be in the form of an isolated single cell or aggregate of cells such as a friable callus, or a cultured cell, or can be part of higher organized unit, for example, a plant tissue, plant organ, or plant. As such, a plant cell can be a protoplast, a gamete producing cell, or a cell or collection of cells that can regenerate into a whole plant. A seed, which comprises multiple plant cells and is capable of regenerating into a whole plant, is considered plant cell for purposes of this disclosure. Thus, a plant tissue or plant organ can be a seed, protoplast, callus, or any other groups of plant cells that is organized into a structural or functional unit. Particularly useful parts of a plant include harvestable parts and parts useful for propagation of progeny plants. A harvestable part of a plant can be any useful part of a plant, for example, flowers, pollen, seedlings, tubers, leaves, stems, fruit, seeds, roots, and the like. A part of a plant useful for propagation includes, for example, seeds, fruits, cuttings, seedlings, tubers, rootstocks, and the like.

The agriculture industry produces crops that are used to feed humans and animals, and that are further used in other industries to prepare products as diverse as adhesives and explosives. Maize (corn), for example, is used as human food, livestock feed (e.g., beef cattle, dairy cattle, hogs, and poultry feed), and a raw material in industry. Food uses of maize include consumption of maize kernels as well as products of dry-milling and wet-milling industries (e.g., grits, meal, flour, maize starch, maize syrups, and dextrose). Maize oil is recovered from maize germ, which is a by-product of the dry-milling and wet-milling industries. Industrial uses of maize include production of ethanol, maize starch in the wet-milling industry and maize flour in the dry-milling industry. The industrial applications of maize starch and flour are based on their functional properties, including, for example, viscosity, film formation, adhesive properties, and ability to suspend particles. Maize starch and flour have application in the paper and textile industries, and also are used in adhesives, building materials, foundry binders, laundry starches, explosives, oil-well muds, and other mining applications.

Many crop plants, including wheat, maize, tomatoes, and melons are grown as hybrids, which exhibit greater vigor and improved qualities as compared to the parental plants. The development of hybrids in a plant breeding program requires, in general, the development of homozygous inbred lines, the crossing of these lines, and the evaluation of the crosses. Pedigree breeding and recurrent selection breeding methods are used to develop inbred lines from breeding populations. For example, maize plant breeding programs combine the genetic backgrounds from two or more inbred lines (or various other germplasm sources) into breeding pools, from which new inbred lines are developed by self-pollinating (selfing) and selection of desired phenotypes. The selected inbreds then are crossed with other inbred lines and the hybrids from these crosses are evaluated to determine which of those have commercial potential. As such, plant breeding and hybrid development are expensive and time consuming processes.

Pedigree breeding starts with the crossing of two genotypes, each of which may have one or more desirable characteristics that is lacking in the other or which complements the other. If the two original parents do not provide all the desired characteristics, other sources can be included in the breeding population. Using this method, superior plants are selected and selfed in successive generations until homogeneous plant lines are obtained. Recurrent selection breeding such as backcrossing can be used to improve an inbred line and a hybrid made using the inbreds. Backcrossing can be used to transfer a specific desirable trait from one inbred or source to a second inbred that lacks that trait, for example, by first crossing a superior inbred (recurrent parent) to a donor inbred (non-recurrent parent) that carries the appropriate gene (or genes) for the trait in question, crossing the progeny of the first cross back to the superior recurrent parent, and selecting in the resultant progeny for the desired trait to be transferred from the non-recurrent parent. After five or more backcross generations with selection for the desired trait, the progeny are homozygous for loci controlling the characteristic being transferred, and are like the superior parent for essentially all other genes. The last backcross generation is selfed to give pure breeding progeny for the gene being transferred. A hybrid developed from such inbreds containing the transferred gene is essentially the same as a hybrid developed from the same inbreds without the transferred gene.

A single cross hybrid (F1) results from the cross of two inbred lines (P1 and P2), each of which has a genotype that complements the genotype of the other. In the development of commercial hybrids in a maize plant breeding program, for example, only F1 hybrid plants are sought, as they are more vigorous than their inbred parents. This hybrid vigor (heterosis) can be manifest in many polygenic traits such as increased vegetative growth and increased yield. The development of a hybrid in a maize plant breeding program, for example, involves the selection of plants from various germplasm pools for initial breeding crosses; the selfing of the selected plants from the breeding crosses for several generations to produce a series of inbred lines, which, although different from each other, breed true and are highly uniform; and crossing the selected inbred lines with different inbred lines to produce the hybrid F1 progeny. During the inbreeding process in maize, the vigor of the lines decreases, but is restored when two different inbred lines are crossed to produce the hybrid plants. An important consequence of the homozygosity and homogeneity of the inbred lines is that the F1 hybrid between a defined pair of inbred parental plants always is the same. As such, once the inbreds that provide a superior hybrid are identified, the hybrid seed can be reproduced indefinitely as long as the homogeneity of the inbred parents is maintained.

Hybrid seed production requires elimination or inactivation of pollen produced by the female parent. Incomplete removal or inactivation of the pollen provides the potential for selfing, raising the risk that inadvertently self pollinated seed will unintentionally be harvested and packaged with hybrid seed. Once the seed is planted, the selfed plants can be identified and selected; the selfed plants are genetically equivalent to the female inbred line used to produce the hybrid. Typically, the selfed plants are identified and selected based on their decreased vigor. For example, female selfed plants are identified by their less vigorous appearance for vegetative and/or reproductive characteristics, including shorter plant height, small ear size, ear and kernel shape, cob color, or other characteristics. Selfed lines also can be identified using molecular marker analyses (see, e.g., Smith and Wych, *Seed Sci. Technol.* 14:1-8, 1995, which is incorporated herein by reference). Using such methods, the homozygosity of the self pollinated line can be verified by analyzing allelic composition at various loci in the genome.

Because hybrid plants are important and valuable field crops, plant breeders are continually working to develop high-yielding hybrids that are agronomically sound based on stable inbred lines. The availability of such hybrids allows a maximum amount of crop to be produced with the inputs used, while minimizing susceptibility to pests and environmental stresses. To accomplish this goal, the plant breeder must develop superior inbred parental lines for producing hybrids by identifying and selecting genetically unique individuals that occur in a segregating population. In one aspect, the invention contributes to this goal by providing transgenic plants that are substantially male ("supermales") or are substantially females ("superfemales"), such plant being useful as parental plants to generate hybrids.

Accordingly, the invention provides a transgenic non-human organism containing, in its genome, an exogenously introduced nucleic acid molecule encoding a ZmZFP2 polypeptide, or a peptide portion thereof, and/or a corresponding complementary sequence. In one embodiment, the transgenic organism is a transgenic plant that contains, integrated in its genome, an exogenous nucleic acid molecule encoding a ZmZFP2 polypeptide or peptide portion thereof, or encoding a nucleotide sequence complementary thereto. The transgenic plant can be any type of plant, including, for example, a monocotyledonous plant (monocot) or a dicotyledonous plant (dicot), and a gymnosperm or angiosperm. In aspects of the invention, the transgenic plant is a maize, rice, wheat, barley, soybean, or sorghum plant. The invention also provides cells and cuttings of such transgenic plants, isolated seed produced by the transgenic plants, and progeny plants generated from the cells, cuttings, or seed of the transgenic plants.

A ZmZFP2 nucleic acid molecule in a transgenic plant of the invention can be ectopically expressed (i.e., expressed in cells in which it is not normally expressed, or at a time or developmental stage at which it is not normally expressed), thereby modulating development of the transgenic plant. Ectopic expression can be effected, for example, by operatively linking the ZmZFP2 nucleic acid molecule to a promoter having the desired characteristics. A ZmZFP2 nucleic acid molecule can be operatively linked, for example, to an inducible promoter, such that the encoded product (e.g., ZmZFP2 polypeptide or ZmZFP2 co-suppressor RNA) can be expressed upon contact of a transgenic plant with the appropriate inducing agent, or can be operatively linked, for example, to a TB1 promoter such that the ZmZFP2 polynucleotide is expressed ectopically in axillary meristems and stamens. Ectopic expression of a ZmZFP2 polypeptide in meristem cells that are destined to become ovary cells, for example, can prevent the formation of ovary cells, thereby generating a supermale plant, which can be useful for hybrid production. Also ectopic expression of a ZmZFP2-like—gene, for example, in maize ear inflorescence meristem can delay termination, thereby increasing the number of florets and, therefore, yield. In comparison, ectopic expression of a ZmZFP2-like suppressor RNA or antisense, for example, in maize ear inflorescence meristem can accelerate termination of the meristem and reduce or eliminate the whole ear leading to supermale plant or some percentage of ear florets when desired. Accordingly, in various aspects, transgenic plants containing an ectopically expressible nucleic acid molecule encoding a ZmZFP2 polypeptide are provided, including, for example, transgenic crop plants that exhibit increased yield as compared to corresponding wild type crop plants, transgenic supermale plants that have only male structures, and transgenic superfemale plants that have only female structures. Further, it should be recognized that, prior to the present disclosure, it was not known that the expression of ZFP2-like polypeptides regulated meristem differentiation in plants. Accordingly, in a more general aspect, the present invention provides methods of altering meristem differentiation by modulating ZFP2 gene expression in meristem cells, or progenitors or progeny thereof. As disclosed herein, such methods can utilize a ZmZFP2 haplotype, or any other ZFP2-like polynucleotide or polypeptide (see, e.g., SEQ ID NOS: 15 to 18; see, also, FIG. 1).

A transgenic plant of the invention can be regenerated from a genetically modified plant cell (i.e., a whole plant can be regenerated from a plant cell); a group of plant cells; a protoplast; a seed; or a piece of a plant such as a leaf, a cotyledon or a cutting. Regeneration from protoplasts varies from species to species of plants. For example, a suspension of protoplasts can be made and, in certain species, embryo formation can be induced from the protoplast suspension, to the stage of ripening and germination. The culture media generally contains various components necessary for growth and regeneration, including, for example, hormones such as auxins and cytokinins; and amino acids such as glutamic acid and proline, depending on the particular plant species. Efficient regeneration will depend, in part, on the medium, the genotype, and the history of the culture, and is reproducible if these variables are controlled.

Regeneration can occur from plant callus, explants, organs or plant parts. Transformation can be performed in the context of organ or plant part regeneration. (see *Meth. Enzymol. Vol.* 118; Klee et al. *Ann. Rev. Plant Physiol.* 38:467 (1987), which is incorporated herein by reference). Utilizing the leaf disk-transformation-regeneration method, for example, disks are cultured on selective media, followed by shoot formation in about two to four weeks (see Horsch et al., supra, 1985). Shoots that develop are excised from calli and transplanted to appropriate root-inducing selective medium. Rooted plantlets are transplanted to soil as soon as possible after roots appear. The plantlets can be repotted as required, until reaching maturity.

In seed propagated crops, mature transgenic plants can be self-pollinated to produce a homozygous inbred plant. The resulting inbred plant produces seeds that contain the introduced transgene, which can comprise a heterologous nucleotide sequence encoding a bioluminescent polypeptide, and can be grown to produce plants that express the polypeptide. Methods for breeding plants and selecting for crossbred plants having desirable characteristics or other characteristics of interest are disclosed herein or otherwise known to plant breeders.

In various aspects, one or more transgenes is introduced into plant cells. When used in reference to a transgene, the term "introducing" means transferring the exogenous nucleic acid molecule into a cell. A nucleic acid molecule can be introduced into a plant cell by a variety of methods. For example, the transgene can be contained in a vector, can be introduced into a plant cell using a direct gene transfer method such as electroporation or microprojectile mediated transformation, or using *Agrobacterium* mediated transformation. As used herein, the term "transformed" refers to a plant cell containing an exogenously introduced nucleic acid molecule. One or more exogenous nucleic acid molecules can be introduced into plant cells using any of numerous well known and routine methods for plant transformation, including biological and physical plant transformation protocols (see, e.g., Miki et al., "Procedures for Introducing Foreign DNA into Plants"; In Methods in Plant Molecular Biology and Biotechnology, Glick and Thompson, Eds. (CRC Press, Inc., Boca Raton, 1993) pages 67-88, which is incorporated herein by reference). In addition, expression vectors and in vitro culture methods for plant cell or tissue transformation and regeneration of plants are routine and well known (see, e.g., Gruber et al., "Vectors for Plant Transformation"; Id. at pages 89-119, which is incorporated herein by reference).

*Agrobacterium* mediated transformation provides a useful method for introducing a transgene into plants (Horsch et al., *Science* 227:1229 1985, which is incorporated herein by reference). *A. tumefaciens* and *A. rhizogenes* are plant pathogenic soil bacteria that genetically transform plant cells. The Ti and Ri plasmids of *A. tumefaciens* and *A. rhizogenes*, respectively, carry genes responsible for genetic transformation of the plant (see, e.g., Kado, *Crit. Rev. Plant Sci.* 10:1, 1991; see, also, Moloney et al., *Plant Cell Reports* 8:238, 1989; U.S. Pat. No. 5,591,616; WO 99/47552; Weissbach and Weissbach, "Methods for Plant Molecular Biology" (Academic Press, NY 1988), section VIII, pages 421-463; Grierson and Corey, "Plant Molecular Biology" 2d Ed. (Blackie, London 1988), Chapters 7-9, each of which is incorporated herein by reference; see, also, Horsch et al., supra, 1985).

With respect to *A. tumefaciens*, the wild type form contains a Ti plasmid, which directs production of tumorigenic crown gall growth on host plants. Transfer of the tumor inducing T-DNA region of the Ti plasmid to a plant genome requires the Ti plasmid-encoded virulence genes as well as T-DNA borders, which are a set of direct DNA repeats that delineate the region to be transferred. An *Agrobacterium* based vector is a modified form of a Ti plasmid, in which the tumor inducing functions are replaced by a nucleotide sequence of interest that is to be introduced into the plant host. Methods of using *Agrobacterium* mediated transformation include cocultivation of *Agrobacterium* with cultured isolated protoplasts; transformation of plant cells or tissues with *Agrobacterium*; and transformation of seeds, apices or meristems with *Agrobacterium*. In addition, in planta transformation by *Agrobacterium* can be performed using vacuum infiltration of a suspension of *Agrobacterium* cells (Bechtold et al., *C. R. Acad. Sci. Pads* 316:1194, 1993, which is incorporated herein by reference).

*Agrobacterium* mediated transformation can employ cointegrate vectors or binary vector systems, in which the components of the Ti plasmid are divided between a helper vector, which resides permanently in the *Agrobacterium* host and carries the virulence genes, and a shuttle vector, which contains the gene of interest bounded by T-DNA sequences. Binary vectors are well known in the art (see, for example, De Framond, *BioTechnology* 1:262, 1983; Hoekema et al., *Nature* 303:179, 1983, each of which is incorporated herein by reference) and are commercially available (Clontech; Palo Alto Calif.). For transformation, *Agrobacterium* can be cocultured, for example, with plant cells or wounded tissue such as leaf tissue, root explants, hypocotyls, cotyledons, stem pieces or tubers (see, for example, Glick and Thompson, "Methods in Plant Molecular Biology and Biotechnology" (Boca Raton Fla., CRC Press 1993), which is incorporated herein by reference). Wounded cells within the plant tissue that have been infected by *Agrobacterium* can develop organs de novo when cultured under the appropriate conditions; the resulting transgenic shoots eventually give rise to transgenic plants, which contain an exogenously introduced ZmZFP2 polynucleotide, or an oligonucleotide portion thereof.

*Agrobacterium* mediated transformation has been used to produce a variety of transgenic plants, including, for example, transgenic cruciferous plants such as *Arabidopsis*, mustard, rapeseed and flax; transgenic leguminous plants such as alfalfa, pea, soybean, trefoil and white clover; and transgenic solanaceous plants such as eggplant, petunia, potato, tobacco and tomato (see, for example, Wang et al., "Transformation of Plants and Soil Microorganisms" (Cambridge, University Press 1995), which is incorporated herein by reference). In addition, *Agrobacterium* mediated transformation can be used to introduce an exogenous nucleic acid molecule into apple, aspen, belladonna, black currant, carrot, celery, cotton, cucumber, grape, horseradish, lettuce, morning glory, muskmelon, neem, poplar, strawberry, sugar beet, sunflower, walnut, asparagus, rice and other plants (see, for example, Glick and Thompson, supra, 1993; Hiei et al., *Plant J.* 6:271-282, 1994; Shimamoto, Science 270: 1772-1773, 1995). Suitable strains of *A. tumefaciens* and vectors as well as transformation of *Agrobacteria* and appropriate growth and selection media are well known in the art (GV3101, pMK90RK), Koncz, *Mol. Gen. Genet.* 204:383-396, 1986; (C58C1, pGV3850kan), Deblaere, *Nucl. Acid Res.* 13:4777, 1985; Bevan, *Nucleic Acid Res.* 12:8711, 1984; Koncz, *Proc. Natl. Acad. Sci. USA* 86:8467-8471, 1986; Koncz, *Plant Mol. Biol.* 20:963-976, 1992; Koncz, Specialized vectors for gene tagging and expression studies. In: Plant Molecular Biology Manual Vol. 2, Gelvin and Schilperoort (Eds.), Dordrecht, The Netherlands: Kluwer Academic Publ. (1994), 1-22; European Patent A-1 20 516; Hoekema: The Binary Plant Vector System, Offsetdrukkerij Kanters B. V., Alblasserdam (1985), Chapter V; Fraley, *Crit. Rev. Plant Sci.,* 4:1-46; An, *EMBO J.* 4:277-287, 1985).

Where the exogenous nucleic acid molecule is contained in a vector, the vector can contain functional elements, for example "left border" and "right border" sequences of the T-DNA of *Agrobacterium*, which allow for stable integration into a plant genome. Furthermore, methods and vectors that permit the generation of marker-free transgenic plants, for example, where a selectable marker gene is lost at a certain stage of plant development or plant breeding, are known, and include, for example, methods of co-transformation (Lyznik, *Plant Mol. Biol.* 13:151-161, 1989; Peng, *Plant Mol. Biol.* 27:91-104, 1995), or methods that utilize enzymes capable of promoting homologous recombination in plants (see, e.g., WO97/08331; Bayley, *Plant Mol. Biol.* 18:353-361, 1992; Lloyd, *Mol. Gen. Genet.* 242:653-657, 1994; Maeser, *Mol. Gen. Genet.* 230:170-176, 1991; Onouchi, *Nucl. Acids Res.* 19:6373-6378, 1991; see, also, Sambrook et al., supra, 1989).

Direct gene transfer methods also can be used to introduce the desired transgene (or transgenes) into cells, including plant cells that are refractory to *Agrobacterium*-mediated transformation (see, e.g., Hiei et al., *Plant J.* 6:271-282, 1994; U.S. Pat. No. 5,591,616, each of which is incorporated herein by reference). Such methods include direct gene transfer (see European Patent A 164 575), injection, electroporation, biolistic methods such as particle bombardment, pollen-mediated transformation, plant RNA virus-mediated transformation, liposome-mediated transformation, transformation using wounded or enzyme-degraded immature embryos, or wounded or enzyme-degraded embryogenic callus, and the like. Direct gene transfer methods include microprojectile-mediated (biolistic) transformation methods, wherein the transgene is carried on the surface of microprojectiles measuring 1 to 4 Tm. A vector, particularly an expression vector containing the transgene(s) of interest is introduced into plant tissues with a biolistic device that accelerates the microprojectiles to speeds of 300 to 600 m/s, sufficient to penetrate plant cell walls and membranes (see, e.g., Sanford et al., *Part. Sci. Technol.* 5:27, 1987; Sanford, Trends Biotech. 6:299, 1988, Klein et al., *BioTechnology* 6:559-563, 1988; Klein et al., *BioTechnology* 10:268, 1992, each of which is incorporated herein by reference). In maize, for example, several target tissues can be bombarded with DNA-coated microprojectiles in order to produce transgenic plants, including, for example, callus (Type I or Type II), immature embryos, and meristem tissue.

Other methods for physical delivery of a transgene into plants utilize sonication of the target cells (Zhang et al., *BioTechnology* 9:996, 1991, which is incorporated herein by reference); liposomes or spheroplast fusion (Deshayes et al., *EMBO J.* 4:2731, 1985; Christou et al., *Proc Natl. Acad. Sci., USA* 84:3962, 1987, each of which is incorporated herein by reference); CaCl$_2$ precipitation or incubation with polyvinyl alcohol or poly-L-ornithine (Hain et al., *Mol. Gen. Genet.* 199: 61, 1985; Draper et al., *Plant Cell Physiol* 23:451, 1982, each of which is incorporated herein by reference); and electroporation of protoplasts and whole cells and tissues (Donn et al., In "Abstracts of VIIIth International Congress on Plant Cell and Tissue Culture" IAPTC, A2-38, pg. 53, 1990; D'Halluin et al., *Plant Cell* 4:1495-1505, 1992; Spencer et al., *Plant Mol. Biol.* 24:51-61, 1994, each of which is incorporated herein by reference).

A direct gene transfer method such as electroporation can be particularly useful for introducing exogenous nucleic acid molecules into a cell such as a plant cell. For example, plant protoplasts can be electroporated in the presence of a recombinant nucleic acid molecule comprising a nucleotide sequence encoding a bioluminescent polypeptide, which can be in a vector (Fromm et al., *Proc. Natl. Acad. Sci., USA* 82:5824, 1985, which is incorporated herein by reference). Electrical impulses of high field strength reversibly permeabilize membranes allowing the introduction of the nucleic acid. Electroporated plant protoplasts reform the cell wall, divide and form a plant callus. Microinjection can be performed as described in Potrykus and Spangenberg (eds.), Gene Transfer To Plants. Springer Verlag, Berlin, N.Y. (1995). A transformed plant cell containing the introduced recombinant nucleic acid molecule can be identified due to the presence of a selectable marker included in the construct, or simply by looking at the plant cells and observing visible bioluminescence.

As mentioned above, microprojectile mediated transformation also provides a useful method for introducing exogenous nucleic acid molecules into a plant cell (Klein et al., *Nature* 327:70-73, 1987, which is incorporated herein by reference). This method utilizes microprojectiles such as gold or tungsten, which are coated with the desired nucleic acid molecule by precipitation with calcium chloride, spermidine or polyethylene glycol. The microprojectile particles are accelerated at high speed into a plant tissue using a device such as the BIOLISTIC PD-1000 particle gun (Bio-Rad; Hercules Calif.). Microprojectile mediated delivery ("particle bombardment") is especially useful to transform plant cells that are difficult to transform or regenerate using other methods. Methods for the transformation using biolistic methods are well known (Wan, *Plant Physiol.* 104:37-48, 1984; Vasil, *BioTechnology* 11:1553-1558, 1993; Christou, *Trends in Plant Science* 1:423-431, 1996). Microprojectile mediated transformation has been used, for example, to generate a variety of transgenic plant species, including cotton, tobacco, corn, hybrid poplar and papaya (see Glick and Thompson, supra, 1993). Important cereal crops such as wheat, oat, barley, sorghum and rice also have been transformed using microprojectile mediated delivery (Duan et al., *Nature Biotech.* 14:494-498, 1996; Shimamoto, Curr. Opin. Biotech. 5:158-162, 1994).

A rapid, transformation regeneration system for the production of transgenic plants such as a system that produces transgenic wheat in two to three months (see Eur. Pat. No. EP 0709462A2, which is incorporated herein by reference) also can be useful for producing a transgenic plant according to a method of the invention, thus allowing more rapid identification of gene functions. The transformation of most dicotyledonous plants is possible with the methods described above. Transformation of monocotyledonous plants also can be transformed using, for example, biolistic methods as described above, protoplast transformation, electroporation of partially permeabilized cells, introduction of DNA using glass fibers, *Agrobacterium* mediated transformation, and the like.

Plastid transformation also can be used to introduce a nucleic acid molecule into a plant cell (U.S. Pat. Nos. 5,451,513, 5,545,817, and 5,545,818; WO 95/16783; McBride et al., *Proc. Natl. Acad. Sci., USA* 91:7301-7305, 1994). Chloroplast transformation involves introducing regions of cloned plastid DNA flanking a desired nucleotide sequence, for example, a selectable marker operatively linked to a ZmZFP2 polynucleotide, into a suitable target tissue, using, for example, a biolistic or protoplast transformation method (e.g., calcium chloride or PEG mediated transformation). One to 1.5 kb flanking regions ("targeting sequences") facilitate homologous recombination with the plastid genome, and allow the replacement or modification of specific regions of the plastome. Using this method, point mutations in the chloroplast 16S rRNA and rps12 genes, which confer resistance to spectinomycin and streptomycin, can be utilized as selectable markers for transformation (Svab et al., *Proc. Natl. Acad. Sci., USA* 87:8526-8530, 1990; Staub and Maliga, *Plant Cell* 4:39-45, 1992) and can result in stable homopiasmic transformants at a frequency of approximately one per 100 bombardments of target leaves. The presence of cloning sites between these markers allowed creation of a plastid targeting vector for introduction of foreign genes (Staub and Maliga, *EMBO J.* 12:601-606, 1993). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab and Maliga, *Proc. Natl. Acad. Sci., USA* 90:913-917, 1993). Approximately 15 to 20 cell division cycles following transformation are generally required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein.

Plants suitable for purposes of the present invention can be monocots or dicots and include, but are not limited to, maize, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugar beet, sunflower, rapeseed, clover, tobacco, carrot, cotton, alfalfa, rice, potato, eggplant, cucumber, *Arabidopsis thaliana*, and woody plants such as coniferous and deciduous trees. Thus, a transgenic plant or genetically modified plant cell of the invention can be an angiosperm or gymnosperm.

Angiosperms are divided into two broad classes based on the number of cotyledons, which are seed leaves that generally store or absorb food; a monocotyledonous angiosperm has a single cotyledon, and a dicotyledonous angiosperm has two cotyledons. Angiosperms produce a variety of useful products including materials such as lumber, rubber, and paper; fibers such as cotton and linen; herbs and medicines such as quinine and vinblastine; ornamental flowers such as roses and, where included within the scope of the present invention, orchids; and foodstuffs such as grains, oils, fruits and vegetables. Angiosperms encompass a variety of flowering plants, including, for example, cereal plants, leguminous plants, oilseed plants, hardwood trees, fruit-bearing plants and ornamental flowers, which general classes are not necessarily exclusive. Cereal plants, which produce an edible grain cereal, include, for example, corn, rice, wheat, barley, oat, rye, orchardgrass, guinea grass, sorghum and turfgrass. Leguminous plants include members of the pea family (Fabaceae) and produce a characteristic fruit known as a legume. Examples of leguminous plants include, for example, soybean, pea, chickpea, moth bean, broad bean, kidney bean, lima bean, lentil, cowpea, dry bean, and peanut, as well as alfalfa, birdsfoot trefoil, clover and sainfoin. Oilseed plants, which have seeds that are useful as a source of oil, include soybean, sunflower, rapeseed (canola) and cottonseed. Angiosperms also include hardwood trees, which are perennial woody plants that generally have a single stem (trunk). Examples of such trees include alder, ash, aspen, basswood (linden), beech, birch, cherry, cottonwood, elm, eucalyptus, hickory, locust, maple, oak, persimmon, poplar, sycamore, walnut, *sequoia*, and willow. Trees are useful, for example, as a source of pulp, paper, structural material and fuel.

Angiosperms are fruit-bearing plants that produce a mature, ripened ovary, which generally contains seeds. A fruit can be suitable for human or animal consumption or for collection of seeds to propagate the species. For example, hops are a member of the mulberry family that are prized for their flavoring in malt liquor. Fruit-bearing angiosperms also include grape, orange, lemon, grapefruit, avocado, date, peach, cherry, olive, plum, coconut, apple and pear trees and blackberry, blueberry, raspberry, strawberry, pineapple, tomato, cucumber and eggplant plants. An ornamental flower is an angiosperm cultivated for its decorative flower. Examples of commercially important ornamental flowers include rose, lily, tulip and chrysanthemum, snapdragon, camellia, carnation and petunia plants, and can include orchids. It will be recognized that the present invention also can be practiced using gymnosperms, which do not produce seeds in a fruit.

The invention also provides a method of altering tissue development in a plant by modulating ZmZFP2 polypeptide activity in meristem cells of the plant, wherein the ZmZFP2 polypeptide regulates differentiation of the meristem cells. As disclosed herein, ZmZFP2 expression is elevated in meristem, and is down regulated as the meristem tissue differentiates into a specific tissue type. As such, tissue development can be altered in a plant by modulating ZmZFP2 levels in cells of the plant, particularly in meristem cells, in cells that give rise to meristem cells, or in cells that arise from meristem cells. Such a method can be performed, for example, by ectopically expressing a nucleotide sequence encoding an exogenous ZmZFP2 polypeptide in plant meristem cells, thus increasing the amount of ZmZFP2 in the cell and delaying or inhibiting differentiation or termination of the meristem cells into a specific cell type. For example, ectopic expression of ZmZFP2 in maize ear meristem can result in generation of an increased number of florets, thus increasing yield as compared to a corresponding plant lacking the increased ZmZFP2 activity.

Methods of producing a transgenic plant by introducing an exogenous ZmZFP2 polynucleotide into a plant cell and growing a plant having the exogenous polynucleotide stably integrated in its genome also are provided, as are methods of generating progeny of such a transgenic plant. A progeny plant can be generated by crossing the (first) transgenic plant with a second plant, which can be a wild type plant or can be a second transgenic plant that can be the same as or different from first transgenic plant. For example, a transgenic superfemale plant, which ectopically expresses a ZmZFP2 polypeptide in meristem cells that would be destined to become stamen, can be crossed with a plant having a desirable genotype to generate hybrid plants. Accordingly, the invention provides progeny of a transgenic plant of the invention, including, for example, a hybrid plant generated using such a transgenic plant. Also provided is seed produced by such a hybrid plant.

The invention also provides methods of identifying molecules that interact specifically with a ZmZFP2 polypeptide. Such a specifically interacting molecule can be a nucleic acid molecule (e.g., a DNA binding site) such as a promoter nucleotide sequence, or can be a second polypeptide that regulates ZmZFP2 transcriptional activity or that is upstream or downstream of ZmZFP2 in a signal transduction pathway. For example, proteins or nucleic acid molecules that can interact specifically with a ZmZFP2 polypeptide can be detected by preparing a radiolabeled ZmZFP2 polypeptide, incubating the labeled ZmZFP2 with an extract prepared from plant meristem cells, and using a gel mobility shift assay to identify the presence of a specifically bound protein. Where a shift in migration of the ZmZFP2 polypeptide is detected, the region of the gel containing the shifted proteins can be isolated, and, for an interacting protein, microsequencing can be used to determine at least a portion of the sequence of the bound protein or, for an interacting nucleic acid molecule, sequencing, with or without PCR, can be used to determine the sequence. The specifically interacting protein or nucleic acid then can be identified based on the sequence information, or oligonucleotide probes can be designed based on the sequence information and used to identify and isolate a polynucleotide comprising the nucleic acid binding site (e.g., a gene containing a ZmZFP2 regulatory element) or encoding the interacting protein.

In addition, the invention provides methods of identifying an agent that modulates ZmZFP2 polypeptide activity. The ZmZFP2 polypeptide activity can be any activity, including, for example, meristem differentiating activity, DNA binding activity and/or transcription activation activity. Transcription activation activity can be determined, for example, by generating a fusion protein comprising a known DNA binding domain of a transcription factor (e.g., a LexA or Gal4 DNA binding domain) operatively linked to a peptide portion of a ZmZFP2 polypeptide lacking the zinc finger-like domain, and examining transcription from a reporter gene containing the DNA binding site specific for the known DNA binding domain. Upon determining a level of transcriptional activity, the system can be perturbed by adding a test agent, which is suspected of being able to modulate transcription due to the ZmZFP2 peptide portion of the fusion protein, wherein a change in transcription activity due to the presence of the test agent identifies the test agent as an agent that modulates ZmZFP2 activity. That the modulation is due to the agent affecting the ZmZFP2 domain and not, for example, to an effect on DNA binding activity can be confirmed by performing a control experiment using a fusion protein comprising the DNA binding domain operatively linked to a different (i.e., not the ZmZFP2) transcription activation domain (e.g., a B42 transactivation domain; see, e.g., Fields and Song, *Nature* 340:245-247, 1989; Chien et al., *Proc. Natl. Acad. Sci., USA* 88:9578-9582, 1991). Accordingly, an agent that modulates ZmZFP2 activity identified by a method of the invention also is provided.

The term "test agent" is used herein to refer to any agent that is being examined for the ability to modulate an activity of a ZmZFP2 polypeptide, or peptide portion thereof. As used herein, the term "modulate" means alter, including increasing and reducing or inhibiting. Generally, a test agent is identified as an agent that modulates ZmZFP2 polypeptide activity when the activity is increased (or reduced) by at least about a two-fold greater amount than is the activity in the absence of the test agent. A test agent can be any type of molecule, including, for example, a polynucleotide, a peptide, a peptidomimetic, a peptoid such as vinylogous peptoid, or a small organic molecule, that one wishes to examine for the ability to modulate ZmZFP2 activity. It will be recognized that a method of the invention is readily adaptable to a high throughput format and, therefore, the method is convenient for screening a plurality of test agents either serially or in parallel. As such, a test agent can be one of a plurality of test agents, for example, a library of test agents produced by a combinatorial method. Methods for preparing a combinatorial library of molecules that can be tested for ZmZFP2 modulating activity include, for example, methods of making a phage display library of peptides, which can be constrained peptides (see, for example, U.S. Pat. No. 5,622, 699; U.S. Pat. No. 5,206,347; Scott and Smith, *Science* 249:386-390, 1992; Markland et al., *Gene* 109:13-19, 1991; each of which is incorporated herein by reference); a peptide library (U.S. Pat. No. 5,264,563, which is incorporated herein by reference); a peptidomimetic library (Blondelle et al., *Trends Anal. Chem.* 14:83-92, 1995; a nucleic acid library (O'Connell et al., supra, 1996; Tuerk and Gold, supra, 1990; Gold et al., supra, 1995; each of which is incorporated herein by reference); an oligosaccharide library (York et al., *Carb. Res.*, 285:99-128, 1996; Liang et al., *Science*, 274:1520-1522, 1996; Ding et al., *Adv. Expt Med. Biol.*, 376:261-269, 1995; each of which is incorporated herein by reference); a lipoprotein library (de Kruif et al., *FEBS Lett.*, 399:232-236, 1996, which is incorporated herein by reference); a glycoprotein or glycolipid library (Karaoglu et al., *J. Cell Biol.*, 130:567-577, 1995, which is incorporated herein by reference); or a chemical library containing, for example, drugs or other pharmaceutical agents (Gordon et al., *J. Med. Chem.*, 37:1385-1401, 1994; Ecker and Crooke, *BioTechnology*, 13:351-360, 1995; each of which is incorporated herein by reference).

In adapting the methods of the invention to a high throughput format, test cells, or extracts of test cells, can be arranged in an array, which can be an addressable array, on a solid support such as a microchip, a glass slide, or a bead, and the cells (or extracts) can be contacted serially or in parallel with one or more test agents, as well as reagents for examining the effect of the agent. Samples arranged in an array or other reproducible pattern can be assigned an address (i.e., a position on the array), thus facilitating identification of the source of the sample. An additional advantage of arranging the samples in an array, particularly an addressable array, is that an automated system can be used for adding or removing reagents from one or more of the samples at various times, or for adding different reagents to particular samples. In addition to the convenience of examining multiple samples at the same time, such high throughput assays provide a means for examining duplicate, triplicate, or more aliquots of a single sample, thus increasing the validity of the results obtained, and for examining control samples under the same conditions as the test samples, thus providing an internal standard for comparing results from different assays. Conveniently, cells or extracts at a position in the array can be examined using differentially labeled reagents such that distinguishable products are generated, thus providing a means for performing a multiplex assay. Such assays can allow the examination of one or more (e.g., 2, 3, 4, 5, 10, 15, 20, or more) test agents and/or targets in a sample.

The following examples are intended to illustrate but not limit the invention.

EXAMPLE 1

Identification ZmZFP2 Zinc Finger Protein Haplotypes From Inbred Plant Cell Lines This example describes the identification of *Zea mays* zinc finger haplotypes that are differentially expressed in active as compared to terminated meristem.

Five mm ear tips were isolated from maize developing ears. One hundred µg total RNA was isolated from 50 mg of tissue, then mRNA was isolated and fluorescent probes were prepared. Genes that were differentially expressed in active inflorescence meristem (IM) but were down-regulated in terminated IM were identified. One sequence, cep7.pk0020.c2 (SEQ ID NO: 1) was identified that contained a C2H2 zinc finger motif and had an amino acid sequence (SEQ ID NO: 2) characteristic of the *Arabidopsis thaliana* ZFP2 (zinc finger-like protein-2) family of proteins (see FIG. 1).

Following identification of cep7.pk0020.c2 (SEQ ID NO: 1), plant genomic DNA was isolated from six different maize inbred lines, Lines A-F, using a standard CTAB extraction protocol (Saghai-Maroof et al., *Proc. Natl. Acad. Sci., USA* 1984). One gram of frozen immature leaf tissue was ground in liquid nitrogen using a pre-chilled mortar and pestle. The powdered tissue was transferred to a 50 ml centrifuge tube (Beckman) along with 25 ml of a pre-heated 60° C. CTAB isolation buffer (1% (w/v) cetyltrimethylammonium bromide; 700 mM NaCl; 0.5% (v/v) 2-mercaptoethanol; 50 mM EDTA, pH 8.0; 50 mM Tris-HCl, pH 8.0, 1 mM 1,10 phenanthroline). The samples were incubated for 1 hr at 60° C. with gently swirling every 10 min, then extracted once with 24:1 (v/v) chloroform:isoamyl alcohol. In order to concentrate the phases, the samples were centrifuged 10 min at 3750 rpm (2800×g) at room temperature. The aqueous phase was removed with a wide bore pipette and transferred to a sterile 50 ml centrifuge tube (Beckman). Nucleic acids were precipitated by the addition of a ⅔ volume of ice cold 2-propanol. The resultant pellet was hooked out, transferred to a clean 50 ml tube and rinsed in 20 ml of a wash solution (80% (v/v) ethanol, 15 mM ammonium acetate) for 30 min before being centrifuged for 10 min at 2200 rpm (1600×g). Following centrifugation, the supernatant was removed and the DNA pellet was air dried overnight on the bench top. The following day, the DNA was resuspended in 0.75 mL TE (10 mM Tris-HCl, 1 mM EDTA, pH 8.0), 5 μl RNase A (10 mg/ml) was added and incubated at 37° C. for 1 hr.

Following genomic DNA isolation, gene specific primers were designed to amplify ZmZFP2 (cep7.pk0020.c2) genomic fragments from maize inbred lines (Lines A-F) using a polymerase chain reaction (PCR) technique. The ZmZFP2 gene specific primer pair included forward and reverse primers, as follows: 72429 (5'-GGMTAAATAATGGGATCCAGTAGTCTC-3'; SEQ ID NO: 19), and 72439 (5'-GCACGAGCTCCGATCCTATA-GAGA-3'; SEQ ID NO: 20), which spanned the entire ZmZFP2 coding sequence, and amplified genomic DNA fragments that were approximately 633 base pairs (bp) for Lines A, C, D and F, and 636 bp for Line B and E. Amplified lengths should be considered approximate lengths because some variation in the ZmZFP2 sequences was detected between inbred lines due to polymorphisms.

PCR was performed using a three-step protocol that was preceded by an initial hot start at 95° C. for 15 min, followed by 35 cycles of denaturation, 94° C. for 45 sec; annealing, 56° C. for 45 sec; extension, 72° C. for 1.5 min, and a final extension at 72° C. for 10 min. Amplicons were separated on a 1% ethidium bromide stained agarose gel. Agarose gels were analyzed on a short wave (310 nm) UV transilluminator and captured using CCD imaging with the QUANTITY ONE image analysis/quantitation software (Bio-Rad; Hercules Calif.). PCR products were gel purified, cloned using the TA method into the pCR4.0 vector (Invitrogen; Carlsbad Calif., and submitted for sequencing. Consensus sequences for each inbred were generated using the SEQUENCHER program, version 4.1.4b7 (Gene Codes Corp.; Ann Arbor Mich.). The ZmZFP2 sequences from each inbred line were compared with one another, and any deviations between sequences in the various inbred lines (e.g., insertion/deletions (indels) and/or single nucleotide polymorphisms (SNPs)) were noted.

Sequence identifiers for genomic DNA sequences that encompassed the full length ZmZFP2 coding sequences, with the nucleotide sequences of the coding region indicated, are as follows:

1) Line A ZmZFP2 nucleotide sequences, SEQ ID NO: 3 (coding sequence at nucleotides 802 to 1296; excluding STOP codon), and corresponding amino acid sequences, SEQ ID NO: 4;
2) Line B ZmZFP2 nucleotide sequences, SEQ ID NO: 5 (nucleotides 804 to 1301), and corresponding amino acid sequences, SEQ ID NO: 6;
3) Line C ZmZFP2 nucleotide sequences, SEQ ID NO: 7 (nucleotides 799 to 1302), and corresponding amino acid sequences, SEQ ID NO: 8;
4) Line D ZmZFP2 nucleotide sequences, SEQ ID NO: 9 (nucleotides 802 to 1296), and corresponding amino acid sequences, SEQ ID NO: 10;
5) Line E ZmZFP2 nucleotide sequences, SEQ ID NO: 11 (nucleotides 804 to 1301), and corresponding amino acid sequences, SEQ ID NO: 12; and
6) Line F ZmZFP2 nucleotide sequences, SEQ ID NO: 13 (nucleotides 802 to 1296), and corresponding amino acid sequences, SEQ ID NO: 14;

EXAMPLE 2

Identification of ZmZFP2 Gene 5' Flanking Sequences

The 5' flanking sequence of the Z. *mays* LINE A ZmZFP2 haplotype was identified in the GSS database of NCBI GenBank, assembled, and analyzed using SEQUENCER program, version 4.1.4b7. The LINE A ZmZFP2 genomic sequence is set forth as SEQ ID NO: 3. PCR primers 74149 (5'-TATTACCTCTCAAG GGAG ACCAAAC-3'; SEQ ID NO: 21) and 74150 (5'-CCATGAGCTCTCTATC TCTATA GGA-3'; SEQ ID NO: 22) were used to screen genomic DNA of six inbred lines. ZFP2-like 5'-flanking genomic sequences were approximately 771 bp for Line C, 774 bp for Line A, Line D and Line F, and 776 bp for Line B and Line E.

PCR was performed using a three-step protocol that was preceded by an initial hot start at 94° C. for 2 min, followed by 35 cycles of denaturation, 94° C. for 20 sec; annealing, 56° C. for 35 sec; extension, 68° C. for 1 min, and a final extension at 68° C. for 10 min. Amplicons were separated on a 1% ethidium bromide stained agarose gel. Agarose gels were analyzed on a short wave (310 nm) UV transilluminator and captured using CCD imaging with the QUANTITY ONE image analysis/quantitation software. PCR products were gel purified, cloned using the TA method into the pCR4.0 vector, and submitted for sequencing. Consensus sequences for each inbred were generated using the SEQUENCER program, version 4.1.4b7.

The 5'-flanking genomic DNA sequences are as follows:

1) Line A ZmZFP2 5' flanking genomic sequence (nucleotides 1 to 801 of SEQ ID NO: 3);
2) Line B ZmZFP2 5' flanking genomic sequence (nucleotides 1 to 803 of SEQ ID NO: 5);
3) Line C ZmZFP2 5' flanking genomic sequence (nucleotides 1 to 799 of SEQ ID NO: 7);
4) Line D ZmZFP2 5' flanking genomic sequence (nucleotides 1 to 801 of SEQ ID NO: 9);
5) Line E ZmZFP2 5' flanking genomic sequence (nucleotides 1 to 803 of SEQ ID NO: 11); and
6) Line F ZmZFP2 5' flanking genomic sequence (nucleotides 1 to 801 of SEQ ID NO: 13).

A comparison of the ZmZFP2 haplotype gene sequences (SEQ ID NOS: 3, 5, 7, 9, 11 and 13) revealed substantial sequence identity (Table 1). Further, the Line C, Line D and Line F ZmZFP2 haplotypes are nearly identical to each other, and the Line B and Line E haplotypes are nearly identical to each other.

TABLE 1

Comparison of ZmZFP2 Coding and 5'-flanking Sequences

| Genotypes | Line A | Line B | Line C | Line D | Line E | Line F |
|---|---|---|---|---|---|---|
| Line A | 100 | 95.6 | 96.7 | 97.1 | 95.7 | 97.2 |
| Line B |  | 100 | 97.9 | 98.3 | 99.8 | 98.4 |
| Line C |  |  | 100 | 99.5 | 98 | 99.6 |
| Line D |  |  |  | 100 | 98.4 | 99.9 |
| Line E |  |  |  |  | 100 | 98.4 |
| Line F |  |  |  |  |  | 100 |

Listed as % identical match.

EXAMPLE 3

Identification of ZFP-2 Like Sequences in Maize Immature Ear Tips Using Oligo Microarray Analysis Immature ear tips from Z. *mays* elite inbreds Line C and Line D were collected from two locations separated by 15 miles. At V11 and V12 stage, approximately 0.5-1.0 mm immature ear tips from primary ears of 80-100 plants were collected and pooled per stage and location, resulting in four samples. The "V" stage refers to the leaf number (counted from the first leaf formed) that shows an exposed ligule (Ritchie, Hanway, and Bensen, 1997 Iowa State University of Science and Technology Cooperative Extension Service, Ames, Iowa, Special Report 48:1-21 {reprinted}), which occurs approximately 6-8 weeks after planting.

The pooled ear tips were immediately frozen in liquid nitrogen. For both Line D and Line C, the inflorescence meristems were active or still producing new spikelet pair meristems. However Line C inflorescence meristems terminated production of new meristems at the V12 stage whereas Line D was still actively producing new spikelet pair meristems. Total RNA was isolated from the tissue using TRIZOL reagent (Invitrogen Corp.) in conjunction with the Phase Lock Gel System (Eppendorf; Westbury N.Y. mRNA was isolated from the total RNA using an mRNA purification kit (Amersham Pharmacia Biotech; Piscataway N.J.).

Microarray profiling was performed using either cDNA protocol as previously described (Zhao and Bruce, *Meth. Mol. Biol.* 236:365-380, 2003; Wang et al., *Plant Mol. Biol.* 52, 873-891, 2003, each of which is incorporated herein by reference) or using an oligo microarray approach (Lipshutz et al., *Nat. Genet.* 21:20-24, 1999; Hughes et al., *Nat. Biotechnol.* 19, 342-347, 2001; Maathuis et al. 2003. Plant J. 35:675-692, 2003; and Casu et al., *Plant Mol. Biol.* 52:371-386, 2003, each of which is incorporated herein by reference). Profiling intensity values across samples were normalized using mean of global dataset and the values from each sample compared with each other to generate ratios (Zhao and Bruce, supra, 2003). Microarray entries were noted that corresponded to high ratio values and a low probability of occurring by chance (p<0.001) when comparing the V11 with V12 stage of Line C. The same entries showed little change in the Line D V11/V12-stage samples, as the meristem remained active in both Line D samples. The ZmFP2 entry exhibited the highest ratio of V11/V12 from Line C immature ears with a range from nearly 3-fold to 10-fold difference depending on exactly when and where the samples were harvested.

EXAMPLE 4

Confirmation of ZmZFP2 Expression Patterns in Maize Immature Ear Tips

Semi-quantitative reverse transcriptase-mediated PCR (RT-PCR) was used to confirm the expression pattern of ZmZFP2 in maize immature ear tips. Immature ear tips (0.5-1 mm) from Pioneer inbred lines, Line C and Line D were harvested at the V11 and V12 stages of development. Total RNA was isolated from the tissue using TRIZOL reagent in conjunction with the Phase Lock Gel System. Twenty µg of total RNA was pretreated with RNase Free™ DNase I enzyme (Ambion; Austin Tex.); 3 µg was used for first strand cDNA synthesis (SUPERSCRIPT II Kit; Invitrogen Corp.). Multiplex PCR was performed using 1 µl of first strand cDNA as template in a 50 µl RT reaction along with HotStar™ Taq DNA polymerase (Qiagen; Valencia Calif.) according to the recommendations of the manufacturer.

Thirty-one cycles were used for the simultaneous amplification of ZmZFP2 cDNA using 0.4 µM each the following primer pairs: 68279 ZmZFP2-F (5'-GCTCCGATCCTATA-GAGATAGAGAGC-3'; SEQ ID NO:23), and 68280 ZmZFP2-R (5'-TTAGCTAGCTTACAGCCTGAGCGAC-3'; SEQ ID NO:24), and of tubulin using 0.13 µM of the following primer pairs: 47208 ZmTub-F (5'-AGCCCGATG-GCACCATGCCCAGTGATACCT-3'; SEQ ID NO:25), and 47209 ZmTub-R (5'-AACACCAAGMTCCCTGCAGC-CCAGTGC-3'; SEQ ID NO:26).

PCR was performed using a three step protocol that was preceded by an initial hot start at 95° C. for 15 min, followed by 31 cycles of denaturation, 94° C. for 45 sec; annealing, 64° C. for 45 sec; extension, 72° C. for 1 min, and a final extension 72° C. for 10 min. In a separate experiment, the number of PCR cycles and primer and template concentrations was shown to be in the linear range of amplification for both genes within the PCR reaction. Amplicons were separated on a 2% ethidium bromide stained agarose gel. Agarose gels were analyzed on a short wave (310 nm) UV transilluminator and captured using CCD imaging with the QUANTITY ONE image analysis/quantitation software. This same software was also used for florescence quantification and normalization of the amplicons.

In FIG. 2, the immature ear tips are shown at top for the two inbred lines, Line C and Line D. The QRT-PCR results clearly show that ZmZFP2 expression is easily detected in ear tips with an active meristem that is still producing new spikelets while expression is below detection in ear tips whose meristems have been 'consumed' or 'terminated' and are not producing any more spikelets. In the longer eared inbred, Line D, the down-regulation of the ZmZFP2 is extended over four- to five-day period as compared to the short ear inbred Line C. At a rate of approximately three spikelets/row per day, Line D was able to produce another 12-15 spikelets/row to a total of approximately 45-47 spikelets/row. 12-15 spikelets/row times the average number of rows for Line D and Line C, which is approximately sixteen rows, the final numbers of potential kernels for Line D over the Line C are 192 to 240. Assuming 50% of all ears are producing this difference in potential kernels and there are no limitations to nutritional and water inputs, this difference can amount to an increase of 50 bushels/acre.

Figure 3:
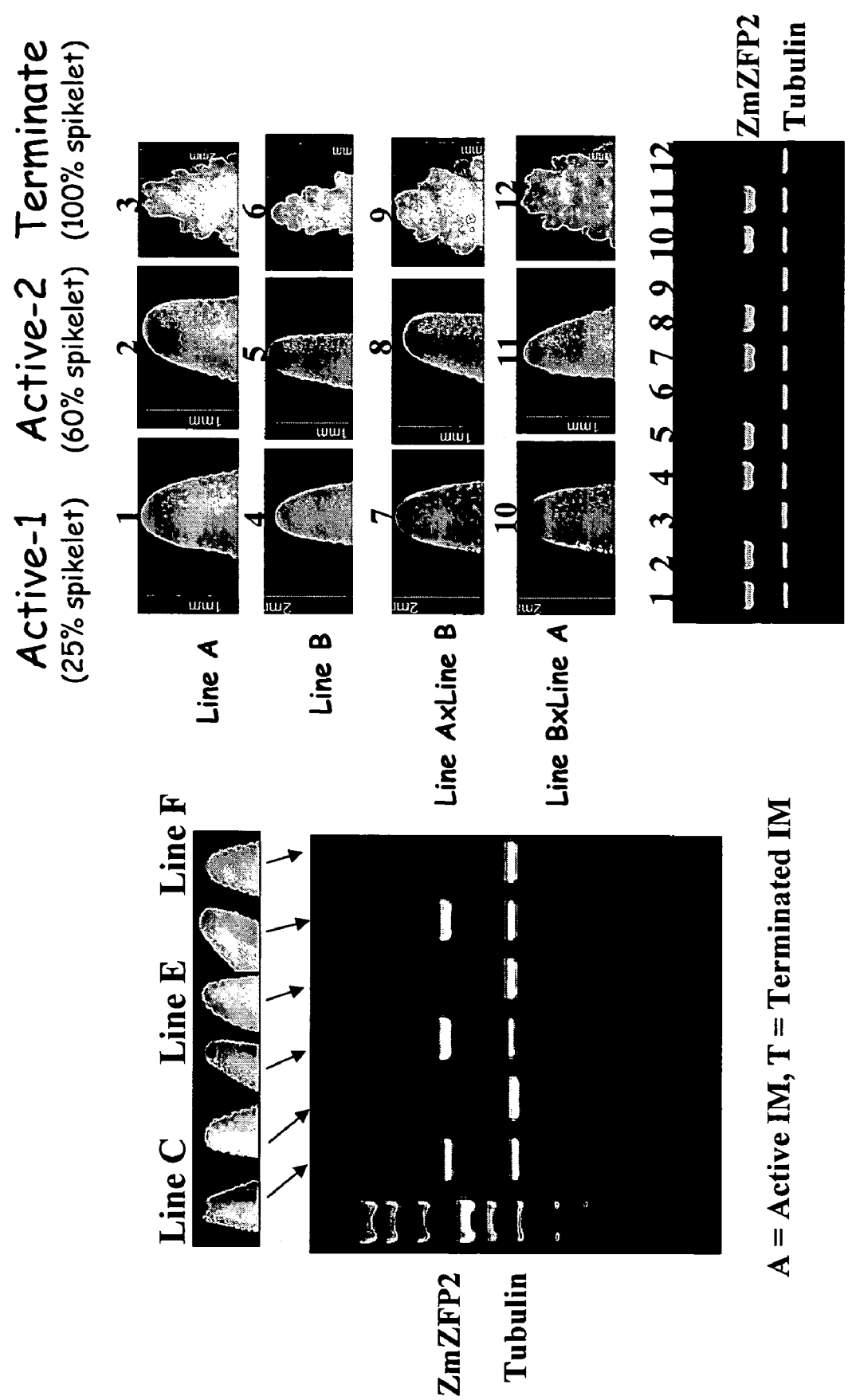
FIG. 3. QRT-PCR data for several other proprietary and public inbred and hybrid immature ear samples. The panels at top left show the images of immature ear tips from three proprietary inbred lines with corresponding QRT-PCR bands for both the ZmZFP2-like gene and tubulin control. The right upper panels show images of the immature ear tips for two public inbreds, resultant hybrid and reciprocal hybrid from these two public inbreds at three developmental stages prior to silk exsertion. The corresponding QRT-PCR bands for the public lines are shown below.

In FIG. 3, the ZmZFP2 gene is shown to be expressed in the active ear meristems from three short-eared inbreds, Line C, Line E, and Line F and down-regulated in terminated ear meristems. The gene is also expressed in ear meristems from LINE A and Line B inbreds and the resultant hybrids suggesting a common regulation for the ZmZFP2 gene expression in ear meristem function.

EXAMPLE 5

Expression of ZFP2-Like Gene in Various Maize Tissues

Young shoots and young roots (V2 stage), ear leaves, flag leaves, stems, tassels and ears (V14-V15 stage), and kernels (10 DAP) from Pioneer inbred lines Line C and Line D were harvested. Total RNA was isolated from the tissue using TRIZOL reagent. Twenty µg of total RNA was pretreated with RNase Free™ DNase I; 3 µg was used for first strand cDNA synthesis using the SUPERSCRIPT II kit. PCR was performed using 2 µl of first strand cDNA as template in a 50 µl RT reaction along with HotStar™ Taq DNA polymerase according to the recommendations of the manufacturer.

Thirty-five cycles were used for the amplification of a Zm-ZFP2-like cDNA using 0.5 µM of each primer of the following primer pair: 68279 Zm-ZFP2-F (5' GCTC-CGATCCTATAGAGATAGAGAGC-3'; SEQ ID NO: 23), and 68280 Zm-ZFP2-R (5'-TTAGCTAGCTTACAGCCT-GAGCGAC-3'; SEQ ID NO: 24).

Figure 4:
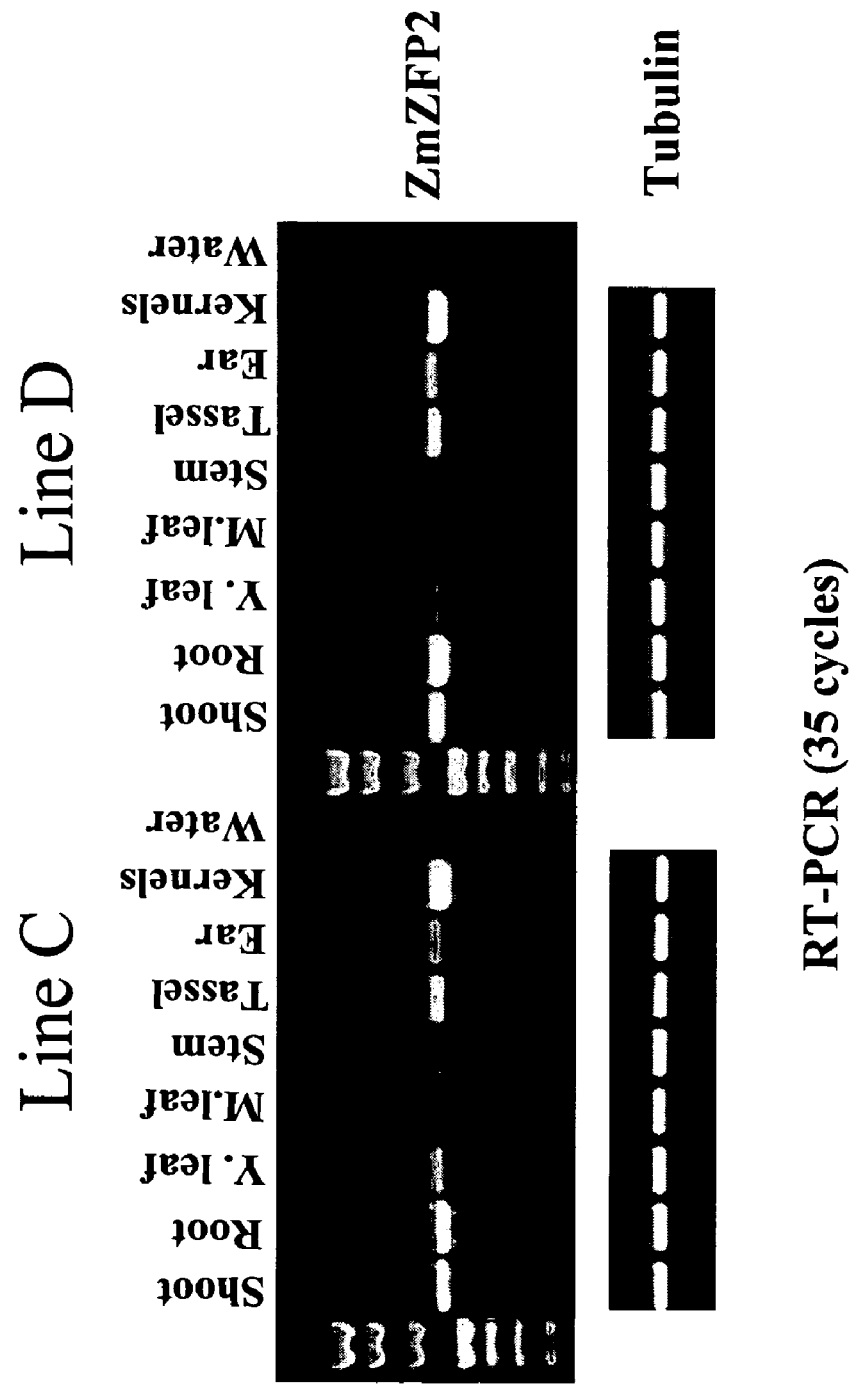
FIG. 4. Illustration of the extent of tissues the ZmZFP2-like gene is active in the two proprietary inbreds. The RT-PCR was conducted to 35 cycles, which amplifies a nearly saturated signal even from a relatively weak gene expression levels. Therefore, these data should only be compared qualitatively not quantitatively. The RT-PCR bands from the tubulin control gene are shown below.

PCR was performed using a three step protocol that was preceded by an initial hot start at 95° C. for 15 min, followed by 35 cycles of denaturation, 94° C. for 45 sec; annealing, 64° C. for 45 sec; extension, 72° C. for 1 min, and a final extension 72° C. for 10 min. Amplicons were separated on a 1.5% ethidium bromide stained agarose gel. Agarose gels were analyzed on a short wave (310 nm) UV transilluminator and captured using CCD imaging with the QUANTITY ONE image analysis/quantitation software. This same software was also used for florescence quantification and normalization of the amplicons. As shown in FIG. 4, ZmZFP2 was expressed at various levels in all of the tissues examined.

A polymorphic PstI cleavable PCR band from the ZmZFP2 gene was genetically linked to two single-sequence-repeat markers, bcd98a and umc1358 on chromosome 1 using genomic DNA from recombinant LINE A X Line B population previously described (see references within the website www.maizegdb.org). The chromosomal linkage group was confirmed by specifically amplifying the ZmZFP2 gene from maize-oat addition line genomic DNA (Kynast, R. G. et al. *PNAS* 101, 9921-6 [2004]).

EXAMPLE 6

Ectopic Expression of ZmZFP2 Can Affect Floral Numbers

Expression of the ZmZFP2 gene is associated with meristem function. By maintaining expression in the ear tip meristem in transgenics, and preventing down-regulation as normally occurs, the number of florets are increased, resulting in increased grain yield under optimal growing conditions. Conversely, ablating the expression in either the ears or tassel can reduce or ablate the respective floral structure. Such impact on floral organs is useful in generating "supermale" and "superfemale" lines, which produce only male or only female structures, respectively. Such lines can provide increased yield gains in customer and production fields if used, for example, as 10% to 90% ratio, respectively. Manipulating expression of the ZmZFP2 gene in other plant species similarly can be used to impact organ development in various species, including crop species.

A plant promoter TB1 (Hubbard, *Genetics* 162:1927-1935, 2002; Cubas, *Plant J.* 18:215-222, 1999, each of which is incorporated herein by reference) controls expression of target genes in maize axillary meristems and in stamens of ear primordia. Fusing TB1 to the ZmZFP2 gene and introducing this construct into maize transgenics can produce plants with continual expression of ZmZFP2-like in axillary meristems such as the ear shoot, leading to increased number of spikelets formed in the long axis of the ear. Similar results can occur using other specific promoters such as the CLV3 promoter (e.g., a CLV3:ZmZFP2:CLV3 terminator construct), which directs expression in meristems, and the meristem-specific Mzec promoter (P450; e.g., a Mzec: ZmZFP2:PinII terminator construct). A chemically inducible promoter (e.g., IN2-2 promoter; De Veylder et al., *Plant Cell Physiol.* 38:568-577, 1997), ecdysone-receptor promoter system (Padidam et al., *Transgenic Res.* 12:101-109. 2003) or TET de-repressable promoter system (Love, J., et al., J Exp Bot, 2002. 53:1871-7) and PinII terminator can be used to more effectively regulate the timing of the ZmZFP2-like gene expression.

EXAMPLE 7

Transformation and Regeneration of Transgenic Plants

Immature maize embryos from greenhouse donor plants are bombarded with a plasmid containing the ZmZFP2-like-like sequence operably linked to the ear meristem-specific promoter (TB1) and the selectable marker gene PAT, which confers resistance to the herbicide Bialaphos. Alternatively, the selectable marker gene is provided on a separate plasmid. Transformation is performed as follows. Media recipes follow below.

Preparation of Target Tissue:

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2,5-cm target zone in preparation for bombardment.

Preparation of DNA:

A plasmid vector comprising the ZFP2-like sequence operably linked to an ubiquitin promoter is made. This plasmid DNA plus plasmid DNA containing a PAT selectable marker is precipitated onto 1.1 µm (average diameter) tungsten pellets using a $CaCl_2$ precipitation procedure as follows:

100 µl prepared tungsten particles in water
  10 µl (1 µg) DNA in Tris EDTA buffer (1 µg total DNA)
  100 µl 2.5 M $CaCl_2$
  10 µl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 µl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment.

Particle Gun Treatment:

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment:

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored for phenotypic changes associated with the expression of zinc-finger proteins in meristem tissue, for instance: plants having later flowering, or delay in maturity, plants showing an increase in spikelet number in both ear and tassels, an increase in the number of ears per plant, changes in leaf or stem size, volume or integrity or changes in overall plant stature/height. Plants having no zinc-finger protein demonstrate phenotypic changes associated with the lack of said proteins. Examples of the lack of zinc-finger protein in ears or tassels include supermale and superfemale plants, respectively.

Bombardment and Culture Media:

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-1 $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-1 $H_2O$ following adjustment to pH 5.8 with KOH); 3.0 g/l Gelrite (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) Physiol. Plant 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/1 myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

EXAMPLE 8

Agrobacterium-Mediated Transformation

For *Agrobacterium*-mediated transformation of maize with an antisense sequence of the ZFP-like sequence of the present invention, preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the antisense ZFP2-like sequences to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants. Plants are monitored for phenotypic changes associated with the expression of zinc-finger proteins in meristem tissue, for instance: plants having later flowering, or delay in maturity, plants showing an increase in spikelet number in both ear and tassels, an increase in the number of ears per plant, changes in leaf or stem size, volume or integrity or changes in overall plant stature/height. Plants having no zinc-finger protein demonstrate phenotypic changes associated with the lack of said proteins. Examples of the lack of zinc-finger protein in ears or tassels include supermale and superfemale plants, respectively.

EXAMPLE 9

Constitutive Expression of ZMZFP2 Leads to Shorter Stature Plants

Two sets of transgenic plants were generated as described in Example 8 using two different constitutive promoters leading to various plant statures. The expression levels of the ZmZFP2 transgene were measured by RT-PCR analysis using the expression of tubulin as an internal control as described in Example 4. The resultant transgenic events expressed the ZmZFP2 transgene product constitutively at various levels. Out of a total of 10 events involving one constitutive promoter, three showed the highest constitutive levels of ZmZFP2 and displayed extremely short plants without noticeable effects on leaf length and width. The shortened plant phenotype is similar to a class of mutants known as brachytic (Multani, D. S., et al., Loss of an MDR Transporter in Compact Stalks of Maize br2 and *Sorghum* dw3 Mutants. Science, 2003. 302:81-84). Four events showed an intermediate level of constitutive ZmZFP2 expression and likewise intermediate plant heights and shortened tassel branch lengths. And three events showed little or no detectable constitutive expression of ZmZFP2 and were of similar plant heights and stature as events harboring no transgene or nulls. Plants from the three events with high ZmZFP2 expression were 15-25% of the plant height of events with no detectable constitutive expression of the ZmZFP2 gene or of the nulls whereas the intermediates ranged in height from 60-80% of the null plants. Nearly identical results were obtained using the second constitutive promoter as that described above. Overexpression of the ZmZFP2 gene leads to a shortened plant stature that has proven to be useful for improved agronomics (U.S. Pat. No. 6,307,126; U.S. Pat. No. 6,762,348; U.S. Pat. No. 6,830,930; U.S. Pat. No. 6,794,560; Multani, D. S., et al., Loss of an MDR Transporter in Compact Stalks of Maize br2 and *Sorghum* dw3 Mutants. Science, 2003. 302:81-84).

EXAMPLE 10

Overexpression of ZMZFP2 Represses the Biosynthesis of the Gibberellic Acid Pathway Leading to Shortened Plant Stature The RNA from transgenic events with highest and intermediate levels of constitutive ZmZFP2 expression along with plants with no detectable levels of transgenic ZmZFP2 expression was isolated using the methods described in Example 4 and assayed for expression levels of a key GA biosynthetic enzyme, GA-20-oxidase (Oikawa, T., et al., A role of OsGA20ox1, encoding an isoform of gibberellin 20-oxidase, for regulation of plant stature in rice. Plant Mol Biol, 2004. 55:687-700.

The levels of GA-20-oxidase were reduced by ~25% in the intermediate and ~50% in the high ZmZFP2-expressing events relative to the null events. The decrease of the GA-20-oxidase mRNA levels was significantly different from the nulls at 95% confidence interval. This suggests that overexpression of ZmZFP2 represses at least one of the key GA biosynthetic enzymes necessary to produce the biologically active form of GA. This reduction in GA-20-oxidase reduces the level of biologically active GA leading to shorten plant stature similar to what was reported elsewhere (Multani, D. S., et al., Loss of an MDR Transporter in Compact Stalks of Maize br2 and *Sorghum* dw3 Mutants. Science, 2003. 302:81-84; Xu, et al. Co-regulation of ear growth and internode elongation in corn. Plant Growth Regulation, 2004, 44:231-241.)

EXAMPLE 11

Repression of ZMZFP2 leads to an Increase in Plant Stature

Transgenic (TG) plants harboring an RNA: version of ZmZFP2 operably linked to a maize ubiquitin promoter and nontransgenic (NTG) plants were planted at the same time in the summer nursery. The expression levels of the ubiquitin driven ZFP2-RNAi transgene were measured to be at approximately the same level in all transgenic events by RT-PCR analysis (see Example 4) whereas one event (#9) showed a marked reduction in the endogenous ZFP2 RNA that was targeted for repression in seedlings to less than 10% of NTG plants ZFP2 expression levels. Two events showed moderate reduction (#8 & 10) and several other events such as #6 showed little reduction in the endogenous ZFP2 gene. Although the ZFP2—RNAi transgene was expressed at high levels in nearly all events tested, not all events resulted in a complete reduction in the targeted endogenous ZFP2 gene as observed in other systems (e.g. Gupta, R., et al., A chloroplast FKBP interacts with and affects the accumulation of Rieske subunit of cytochrome bf complex. PNAS, 2002. 99:15806-11). Indeed, this variation in repressive control allows the RNAi lines as a knock-down tool to be useful for observing intermediate expression levels of the endogenous gene (Kusaba, M., RNA interference in crop plants. Curr Opin Biotechnol, 2004. 15: 39-43) as opposed to complete knock-out methods such as some transposable element insertions or direct mutagenesis which may lead to infertility or lethality.

Transgenic plants with a highly repressed endogenous ZFP2 gene showed more vigorous growth than its NTG siblings. To further detect the differences in plant growth effects, we measured from 25 to 33 plants per event the plant height of TG vs NTG at flowering. Plant heights were measured in inches from soil line to the tip of the tassel and converted to cm by multiplying the values by 2.54. Three events were measured that included events #6, 9 and 10. For both events #6 and 10, the average heights for TG and NTG plants were essentially the same (approximately 180 cm with no significant difference between TG and NTG). However, for event #9 which showed the strongest reduction in the endogenous ZFP2 gene, the TG average height showed greater than 10% increase over the NTG plants (P<0.01). These data suggest that there may be a threshold in ZFP2 expression levels where the effects on plant height are statistically detectable.

EXAMPLE 12

Sequence Domains

An amino acid alignment of several key CCHH-type zinc finger genes from *arabidopsis* as compared to the ZmZFP2 sequence, was performed using CLUSTAL W (Vector NTI Software Suite version 9.1, Invitrogen, Carlsbad, Calif., USA). In the amino acid alignment the SEQ ID NO: 36 depicts the amino acid sequence of the *arabidopsis* SUPERMAN gene (Sakai, H., et al., Regulation of SUP expression identifies multiple regulators involved in *arabidopsis* floral meristem development. Plant Cell, 2000. 12:1607-18). SEQ ID NO: 33 depicts the amino acid sequence of the *arabidopsis* JAGGED gene (Ohno, C. K., et al., The *Arabidopsis* JAGGED gene encodes a zinc finger protein that promotes leaf tissue development. Development, 2004. 131:1111-1122). The SEQ ID NO: 34 depicts the amino acid sequence of the *arabidopsis* RABBIT EARS gene (Takeda, S., N. Matsumoto, and K. Okada, RABBIT EARS, encoding a SUPERMAN-like zinc finger protein, regulates petal development in *Arabidopsis thaliana*. Development, 2004. 131: 425-34). SEQ ID NO: 35 is the amino acid sequence of the maize RAMOSA1 gene (Vollbrecht, E., et al., Architecture of floral branch systems in maize and related grasses. Nature, 2005. advanced online publication). SEQ ID NO: 30 and SEQ ID NO: 31 refer to *arabidopsis* ZINC FINGER PROTEIN 2 and 7, respectively (NCBI Genbank protein entries AAA87298 and AAA87303). Results are shown in FIG. 5.

The ZmZFP2 gene encodes a 166 amino acid polypeptide that contains a single CCHH-type zinc-finger domain and a C-terminal repressor-like domain. The zinc-finger domain consists of the amino acid sequence C̲XY C̲XRXFXSSQALGGH̲QNAH̲ (SEQ ID NO: 29), where the underlined residues represent the CCHH amino acid residues that form the coordinate binding with a zinc atom. Upon binding of zinc, the folded portion between the coordinate binding shown in bold forms the peptide "finger" that binds to specific DNA sequences (Dathan, N., et al., The *Arabidopsis* SUPERMAN protein is able to specifically bind DNA through its single CCHH zinc finger motif. Nucleic Acids Res, 2002. 30:4945-51). The repression domain, (L/I)DLSL(K/R)L, sometimes referred to as the EAR domain at the C-terminal end of ZmZFP2 is very similar to that described by Hiratsu et al. (Hiratsu, K., et al., The SUPERMAN protein is an active repressor whose carboxy-terminal repression domain is required for the development of normal flowers. FEBS Lett, 2002. 514:351-4). The ZmZP2 contains the DNA binding zinc-finger domain and the transcriptional repressor EAR-domain suggesting that ZmZFP2 acts as a transcriptional repressor. This is consistent with the evidence that overexpression of the ZmZFP2 leads to repression of GA-20-oxidase gene transcript levels, reducing endogenous GA-levels and leading to short-stature plants.

Although the invention has been described with reference to the above examples, it will be understood that modifications and variations are encompassed within the spirit and scope of the invention. Accordingly, the invention is limited only by the following claims.

What is claimed is:

1. An isolated polynucleotide selected from the group consisting of:
   a. a polynucleotide having at least 95% sequence identity, as determined by the GAP algorithm under default parameters, to the full length sequence of a polynucleotide of SEQ ID NO: 1; wherein the polynucleotide encodes a polypeptide which functions as a transcription factor in plant meristem to decrease plant growth;
   b. a polynucleotide encoding a polypeptide of SEQ ID NO: 2; and
   c. a polynucleotide of SEQ ID NO: 1; and
   d. a polynucleotide which is fully complementary to the polynucleotide of (a), (b), or (c).

2. A recombinant expression cassette, comprising the polynucleotide of claim 1, wherein the polynucleotide is operably linked, in sense orientation, to a promoter.

3. A host cell comprising the expression cassette of claim 2.

4. A transgenic plant comprising the recombinant expression cassette of claim 2.

5. The transgenic plant of claim 4, wherein said plant is a monocot.

6. The transgenic plant of claim 4, wherein said plant is a dicot.

7. The transgenic plant of claim 4, wherein said plant is selected from the group consisting of: maize, soybean, sunflower, sorghum, canola, wheat, alfalfa, cotton, rice, barley, millet, peanut and cocoa.

8. A transgenic seed from the transgenic plant of claim 4.

* * * * *